(12) United States Patent
Green et al.

(10) Patent No.: US 7,678,762 B2
(45) Date of Patent: *Mar. 16, 2010

(54) METHODS FOR REDUCING THE RISK OF HYPOGLYCEMIA

(75) Inventors: Daniel T. Green, San Francisco, CA (US); Robert R. Henry, Del Mar, CA (US)

(73) Assignee: DiObex, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/927,535

(22) Filed: Oct. 29, 2007

(65) Prior Publication Data

US 2008/0166399 A1    Jul. 10, 2008

Related U.S. Application Data

(63) Continuation of application No. 11/169,825, filed on Jun. 28, 2005, which is a continuation-in-part of application No. 10/540,803, filed as application No. PCT/US2003/041103 on Dec. 23, 2003, now Pat. No. 7,314,859.

(60) Provisional application No. 60/436,735, filed on Dec. 27, 2002, provisional application No. 60/454,972, filed on Mar. 14, 2003, provisional application No. 60/470,346, filed on May 13, 2003, provisional application No. 60/584,449, filed on Jun. 29, 2004.

(51) Int. Cl.
*A61K 38/00* (2006.01)
*A61K 51/00* (2006.01)

(52) U.S. Cl. ........................................ 514/2; 424/1.69
(58) Field of Classification Search ........................ None
See application file for complete search history.

(56) References Cited

U.S. PATENT DOCUMENTS

| | | | |
|---|---|---|---|
| 2,902,408 A | 9/1959 | Bouman et al. | |
| 3,897,551 A | 7/1975 | Bromer | |
| 4,003,379 A | 1/1977 | Ellinwood, Jr. | |
| 4,492,684 A | 1/1985 | Goosen et al. | |
| 4,498,843 A | 2/1985 | Schneider et al. | |
| 4,538,616 A | 9/1985 | Rogoff | |
| 4,633,878 A | 1/1987 | Bombardieri | |
| 4,826,763 A | 5/1989 | Norris et al. | |
| 4,839,174 A | 6/1989 | Baker et al. | |
| 4,943,435 A | 7/1990 | Baker et al. | |
| 5,101,814 A | 4/1992 | Palti | |
| 5,190,041 A | 3/1993 | Palti | |
| 5,234,903 A | 8/1993 | Nho et al. | |
| 5,234,906 A | 8/1993 | Young et al. | |
| 5,237,993 A | 8/1993 | Skrabal | |
| 5,321,008 A * | 6/1994 | Beaumont et al. | 514/4 |
| 5,359,030 A | 10/1994 | Ekwuribe | |
| 5,445,832 A | 8/1995 | Orsolini et al. | |
| 5,474,552 A | 12/1995 | Palti | |
| 5,508,260 A | 4/1996 | Beaumont et al. | |
| 5,527,771 A | 6/1996 | Beaumont et al. | |
| 5,542,935 A * | 8/1996 | Unger et al. | 604/190 |
| 5,637,568 A | 6/1997 | Orsolini et al. | |
| 5,643,604 A | 7/1997 | Angeles Uribe et al. | |
| 5,643,607 A | 7/1997 | Okada et al. | |
| 5,656,590 A | 8/1997 | Rink et al. | |
| 5,707,641 A | 1/1998 | Gertner et al. | |
| 5,741,211 A | 4/1998 | Renirie et al. | |
| 5,814,600 A | 9/1998 | Rink et al. | |
| 5,849,322 A | 12/1998 | Ebert et al. | |
| 5,869,602 A | 2/1999 | Jonassen et al. | |
| 5,919,216 A | 7/1999 | Houben et al. | |
| 6,093,167 A | 7/2000 | Houben et al. | |
| 6,103,233 A | 8/2000 | Pouletty et al. | |
| 6,107,489 A | 8/2000 | Krantz et al. | |
| 6,114,304 A | 9/2000 | Kolterman et al. | |
| 6,135,978 A | 10/2000 | Houben et al. | |
| 6,191,105 B1 | 2/2001 | Ekwuribe et al. | |
| 6,197,333 B1 | 3/2001 | Onyuksel et al. | |
| 6,217,893 B1 | 4/2001 | Pellet et al. | |
| 6,239,107 B1 | 5/2001 | Gozes et al. | |
| 6,261,280 B1 | 7/2001 | Houben et al. | |
| 6,277,863 B1 | 8/2001 | Krantz et al. | |
| 6,284,727 B1 | 9/2001 | Kim et al. | |
| 6,319,510 B1 | 11/2001 | Yates | |
| 6,329,336 B1 | 12/2001 | Bridon et al. | |

(Continued)

FOREIGN PATENT DOCUMENTS

EP        0300552        1/1989

(Continued)

OTHER PUBLICATIONS

Muhlhauser et al. "Pharmacokinetics and bioavailibilty of injected glucagon: differences between intramuscula, subcutaneous, and intravenous administration," Diabetes Care., 8(1):39-41 Jan.-Feb. 1985 (In IDS of Apr. 20, 2006).*

(Continued)

*Primary Examiner*—Maury Audet
(74) *Attorney, Agent, or Firm*—Knobbe Martens Olson & Bear LLP

(57) ABSTRACT

Pharmaceutical compositions comprising glucagon can be administered to control and treat diabetes while reducing or eliminating the risk of insulin-induced hypoglycemia. Also provided are methods of administering glucagon so as to reduce the risk of hypoglycemia.

20 Claims, 13 Drawing Sheets

U.S. PATENT DOCUMENTS

| | | | |
|---|---|---|---|
| 6,348,214 | B1 | 2/2002 | Onyuksel et al. |
| 6,461,331 | B1 | 10/2002 | Van Antwerp |
| 6,500,918 | B2 | 12/2002 | Ezrin et al. |
| 6,520,326 | B2 | 2/2003 | McIvor et al. |
| 6,540,982 | B1 | 4/2003 | Adjei et al. |
| 6,559,122 | B1 | 5/2003 | Oeswein et al. |
| 6,566,490 | B1 | 5/2003 | Mahiqub et al. |
| 6,572,542 | B1 * | 6/2003 | Houben et al. .............. 600/300 |
| 6,573,238 | B2 | 6/2003 | Shirley et al. |
| 6,589,548 | B1 | 7/2003 | Oh et al. |
| 6,593,295 | B2 | 7/2003 | Bridon et al. |
| 6,645,468 | B2 | 11/2003 | Cutie et al. |
| 6,703,365 | B2 | 3/2004 | Galloway et al. |
| 7,314,859 | B2 | 1/2008 | Green et al. |
| 2001/0016643 | A1 | 8/2001 | Jonassen et al. |
| 2001/0033858 | A1 | 10/2001 | Zhang |
| 2002/0026141 | A1 | 2/2002 | Houben et al. |
| 2002/0114829 | A1 | 8/2002 | Onyuksel et al. |
| 2002/0115592 | A1 | 8/2002 | New et al. |
| 2002/0119146 | A1 | 8/2002 | Dupre |
| 2003/0108568 | A1 | 6/2003 | Bridon et al. |
| 2004/0110817 | A1 * | 6/2004 | Hulin ........................ 514/408 |
| 2006/0014670 | A1 | 1/2006 | Green et al. |
| 2008/0208113 | A1 | 8/2008 | Damiano et al. |

FOREIGN PATENT DOCUMENTS

| | | |
|---|---|---|
| EP | 0442724 | 8/1991 |
| EP | 0684044 | 11/1995 |
| EP | 0816381 | 1/1998 |
| EP | 1264837 | 12/2002 |
| GB | 748857 | 5/1956 |
| GB | 766994 | 1/1957 |
| GB | 766995 | 1/1957 |
| GB | 831907 | 4/1960 |
| GB | 844434 | 8/1960 |
| NZ | 541365 | 8/2005 |
| WO | WO 88/09341 | 12/1988 |
| WO | WO 97/03688 | 2/1997 |
| WO | WO 97/24440 | 7/1997 |
| WO | WO 98/08871 | 3/1998 |
| WO | WO 98/31383 | 7/1998 |
| WO | WO 99/43708 | 9/1999 |
| WO | WO 01/54742 * | 8/2001 |
| WO | WO 01/82874 | 11/2001 |
| WO | WO 01/82981 | 11/2001 |
| WO | WO 02/22154 | 3/2002 |
| WO | WO 02/32957 | 4/2002 |
| WO | WO 02/43566 | 6/2002 |
| WO | WO 02/46227 | 6/2002 |
| WO | WO 2004/060387 | 7/2004 |

OTHER PUBLICATIONS

Trading et al., "Biological and Chemical Properties of Two Glucagon Preparations with Prolonged Action," Eur. J. Pharmacology, 7:206-210 (1969) (IN IDS of Apr. 20, 2006).*
Bremer et al., "Protein delivery with infusion pumps," Pharm. Biotechnol., 10:239-254 (1997) (p. 248-249, In IDS of Apr. 20, 2006).*
Paolisso et al. Pulsatile rather than continuous glucagon infusion leads to greater metabolic derangements in insulin-dependent diabetic subjects. Diabete Metabl., Jan.-Feb. 1990; 16(1): 42-7 (abstract).*
Houlbert et al., "Continuous subcutaneous infusion of glucagon by portable pump in non beta cell tumor hypoglycemia," Diabete Metab. 11 (2): 125-7, Apr. 1985 (Abstract, In IDS of Apr. 20, 2006).*
"Glucagon", Physician's Desk Reference, (c) 2004, p. 1817-1820.
Glucagon for Injection (rDNA origin) FDA label, Instructions for Physicians, Eli Lilly & Co. (2003) pp. 1-7.
"Glucagon (Systemic)" Professional Drug Information, Drugs.com. downloaded from http://drugs.com/MMX/Glucagon.html on Oct. 31, 2008. pp. 1-18.
Office Action dated Aug. 8, 2008, received in U.S. Appl. No. 11/169,825.
El-Khatib, Ph.D., et al., "A feasibility study of bihormonal closed-loop blood glucose control using dual subcutaneous infusion of insulin and glucagon in ambulatory diabetic swine," Journal of Diabetes Science and Technology, Jul. 2009, pp. 1-15, vol. 3, Issue 4.
El-Khatib, Ph.D., et al., "Adaptive closed-loop control provides blooc-glucose regulation using dual subcutaneous insulin and glucagon infusion in diabetic swine," Journal of Diabetes Science and Technology, Mar. 2007, pp. 181-192, vol. 1, Issue 2.
El-Khatib, Ph.D., et al., "Pharmacodynamics and stability of subcutaneously infused glucagon in a type 1 diabetic swine model in vivo," Dabetes Technology & Therapeutics, 2007, pp. 134-144, vol. 9, No. 2.
Liljenquist et al., "Effects of glucagon on lipolysis and ketogenesis in normal and diabetic men," The Journal of Clinical Investigation, Jan. 1974, pp. 190-197, vol. 53.
Marliss, M.D., et al., "Normalization of glycemia in diabetics during meals with insulin and glucagon delivery by the artificial pancreas," Diabetes, Jul. 1977, pp. 663-672, vol. 26, No. 7, New York, NY.
Shichiri et al., "Closed-loop glycemic control with a wearable artificial endocrine pancreas," Diabetes, Dec. 1984, pp. 1200-1202, vol. 33, New York, NY.
De Galan et al. "Pathophysiology and management of recurrent hypoglycaemia and hypoglycaemia unawareness in diabetes." Netherlands Journal of Medicine, Sep. 2006, 64(8): 269-279.
Edelman et al. "Subcutaneous infusion of very low dose-glucagon averts insulin induced hypoglycaemia in patients with type 1 diabetes mellitus." Diabetologia, Sep. 2006, 49 (Suppl. 1): 506.
Fanelli et al. "Glucagon: the effects of its excess and deficiency on insulin action." Nutrition, Metabolism, and Cardiovascular Disease: NMCD, Mar. 2006, vol. 16, suppl. 1, p. S28-S34.
Isley et al. "Very low dose glucagon averts insulin induced hypoglycemia in patients with type 1 diabetes." Diabetes, Jun. 2006, 55 (Suppl. 1): A117.
Supplementary European Search Report dated Aug. 6, 2009, received in European Application No. 05787795.
U.S. Office Action dated Dec. 26, 2008, U.S. Appl. No. 11/963,584, Filing Date Dec. 21, 2007, 9 pages.
U.S. Appl. No. 10/540,803, filed Jun. 23, 2005, Green et al.
U.S. Appl. No. 11/927,513, filed Oct. 29, 2007, Green et al.
U.S. Appl. No. 11/927,587, filed Oct. 29, 2007, Green et al.
U.S. Appl. No. 11/927,621, filed Oct. 29, 2007, Green et al.
U.S. Appl. No. 11/963,584, Dec. 21, 2007, Green et al.
"Defining and Reporting Hypoglycemia in Diabetes" Diabetes Care, 28:1245-1249 (2005).
Abs et al., "Hypoglycemia owing to inappropriate glucagons secretion treated with a continuous subcutaneous glucagons infusion system," Acta Endocrinol (Copenh), 122(3):319-322 (1990).
Attvall et al., "Insulin-antagonistic effects of pulsatile and continuous glucagons infusions in man00a comparison with the effect of adrenaline," J. Clin Endocrinol. Meab., 74(5):1110-1115 (1992).
Aynsley-Green et al., "Nesidioblastosis of the pancreas: definition of the syndrome and the manage of the severe neonatal hyperinsulinaemic hypoglycaemia," Arch. Dis. Child., 56 (7):496-508 (1981).
Banarer et al., "Intraislet Hyperinsulinemia Prevents the Glucagon Response to Hypoglycemia Despite an Intact Autonomic Response," Diabetes 41:958-965, Apr. 2002.
Beaven et al., European J. Biochem., 11:37-42 (1969).
Bergman et al., "Central role of the adipocyte in the metabolic syndrome," J. Investig. Med., 49(1):119-126 (2001).
Bolli et al., "Abnormal Glucose Counterregulation in Insulin-dependent Diabetes Mellitus, Interaction of Anti-Insulin Antibodies and Impaired Glucagon and Epinephrine Secretion," Diabetes 32:134-141 (1983).
Bolli et al., "Nocturnal blood glucose control in type I diabetes mellitus," Diabetes Care, 16 (suppl. 3):71-89 (1993).
Bratusch-Marrain et al., "The role of 'diabetogenic' hormones on carbohydrate and lipid metabolism following oral glucose loading in insulin dependent diabetes: effect of acute hormone administration," Diabetologia, 21(4):387-393 (1981).
Bray, G.A., "The Zucker-fatty rat: a review," Fed. Proc., 36(2):148-153 (1977).
Bremer et al., "Protein delivery with infusion pumps," Pharm. Biotehcnol., 10:239-254 (1997).
Cederblad et al., "Effect of glucagons on glucose production, lipolysis, and gluconeogenesis in familiar hyperinsulinism," Horm. Res., 50(2):94-98 (1998).
Chiou et al., "Adjustment of blood sugar levels with insulin and glucagon eyedrops in normal and diabetic rabbits," J Ocul Pharmacol., 6(3):233-41, fall 1990.
Chiou et al., "Treatment of hypoglycemia with glucagon eye drops," J Ocul Pharmacol., 4(2):179-86, summer 1988.
Christiansen et al. "Zinc-protamine-glucagon in the treatment of Paget's diseases of bone. Preliminary Report," Acta Med. Scand., 196(6):495-496 (1974).
Chuang et al., "Increase of blood glucose concentrations in diabetic patients with glucagon eyedrops," Zhongguo Yao Li Xue Bao, 13(3):193-7, May 1992.
Clarke et al., "The effect of hyperglucagonemia on blood glucose concentrations and on insulin requiremetns in insulin-requiring diabetes mellitus," Diabetes, 27(6):649-652 (1978).
Cryer et al., "Hypoglycemia in Diabetes," Diabetes Care, 26(6):1902-1912 (2003).
Day et al., "Depot-glucagon in the treatment of McArdle's disease," Aust N.Z. J. Med., 15(6):748-750 (1985).
Edelman, "Nocturnal Administration of Very Low Dose Glucagon in Patientls with Type 1 Diabetes Reduces Episodes of Nocturnal Hypoglycemia," PowerPoint Presentation at ADA 67th Scientific Sessions, Jun. 22, 2007.
Fabris et al., "Nasal administration of glucagon in the treatment of neonatal hypoglycemia," Minerva Pediatr. 36:(0):525-8, May 31, 1984.
Gamba et al., Minerva Med. Nov. 3, 1977; 68(53):3613-26.
Gerich et al., "Hormonal Mechanisms of Recovery from Insulin-Induced Hypoglycemia in Man," Am. J. Physiol. 236(4):E380-E385 (1979).
Haymond et al., "Mini-Dose Glucagon Rescue for Hypoglycemia in children with Type 1 Diabetes," Diabetes Care, 24(4):643-645 (2001).
Houlbert et al., "Continuous subcutaneous infusion of glucagon by portable pump in non beta cell tumor hypoglycemia," Diabete Metab. 11(2):125-7, Apr. 1985.
Interview Summary dated Sep. 7, 2007, received un U.S. Appl. No. 10/540,803, 4 pgs.
Ivkovic-Lazar, T., "Development and differentiation of adipose tissue," Med. Pregl., 56(3-4):142-145 (2003), abstract, article in Croatian.
Joseph et al., "Oral delivery of glucagon-like peptide-1 in a modified polymer preparation normalizes basal glycaemia in diabetic db/db mice," Diabetologia., 43(10):1319-28, Oct. 2000.
Kaindl et al., Inn Med. Dec. 15, 1972; 27(24):1097-8.
Kaindl et al., Verh Dtsch Ges Inn Med. 1972; 78:1099-101.
Kalima et al., "The effect of zinc-protamine-glucagon in acute pancreatitis," Ann. Chir. Gynaecol., 69(6):293-295 (1980).
Kollee et al., "Persistent neonatal hypoglycaemia due to glucagons deficiency," Arch Dis. Child, 53(5):422-424 (1978).
Lund et al., Proc. Natl. Acad. Sci. USA 79:345-349 (1982).
Miralles et al., "Experience with intravenous glucagon infusions as a treatment for resistant neonatal hypoglycemia," Arch Pediatr Adolesc Med., 156(1):999-1004, Oct. 2002.
Muhlhauser et al. "Pharmacokinetics and bioavailability of injected glucagon: differences between intramuscula, subcutaneous, and intravenous administration," Diabetes Care., 8(1):39-41 Jan.-Feb. 1985.
Nicolaidis, S., "Physiology of food intake and regulation of body weight," Ann. Endocrinol., 49(2):89-97 (1988).
Paolisso et al. "Effects of pulsatile delivery of insulin and glucagon in humans." Am J Physiol, 1989. p. E686-E696.

Paolisso et al. Pulsatile rather than continuous glucagon infusion leads to greater metabolic derangements in insulin-dependent diabetic subjects. Diabete Metabl., Jan.-Feb. 1990; 16(1):42-7 (abstract).
Patzelt et al., Nature, 282:260-266 (1979).
Pichler et al., "Haemodynamic effects of depot zinc protamine glucagons in heart failure," Wein Klin Wochenschr., 91(2):49-51 (1979).
Pillion et al., "Glucagon administration to the rat via eye drops," J Ocul Pharmacol., 8(4):349-58, Winter 1992.
Pillion et al., "Systemic absorption of insulin and glucagon applied topically to the eyes of rats and a diabetic dog," J Ocul Pharmacol Ther., 11(3):283-95, fall 1995.
Pontirolo et al., "Metabolic effects of intranasally administered glucagon: comparison with intramuscular and intravenous injection," Acta Diabetol Lat. 22(2):103-10, Apr.-Jun. 1985.
Rosenfalck et al. "Nasal Glucagon in the treatment of hypoglycaemia in type 1 (insulin-dependent) diabetic patients," Diabetes Res Clin Pract. 17(1):43-50 Jul. 1992.
Schmid et al., "McArdle's disease: therapeutic use of depot-glucagon," Dtsch Med. Wochenschr., 107(47):1809-1811 (1982).
Stenninger et al., "Intranasal glucagon treatment relieves hypoglycaemia in children with type 1 (insulin-dependent) diabetes mellitus," Diabetologia. 36(10):931-5, Oct. 1993.
Sturm et al., J. Med. Chem. 41:2693-2700 (1998).
Trading et al., "Biological and Chemical Properties of Two Glucagon Preparations with Prolonged Action," Eur. J. Pharmacology, 7:206-210 (1969).
Vella et al., "Effect of Glucagon-Like Peptide 1(7-36) Amide on Glucose Effectiveness and Insulin Action in People with Type 2 Diabetes," Diabetes 49:611-617 (2000).
Webb et al., "Glucagen replacement via micro-osmotic pump corrects hypoglycemia and alpha-cell hyperplasia in prohormone convertase 2 knockout mice," Diabetes 51(2):398-405, Feb. 2002.
File History of U.S. Appl. No. 11/169,825, filed Jun. 28, 2005.
File History of U.S. Appl. No. 10/540,803, filed Dec. 14, 2005.
International Search Report and Written Opinion received in International Application No. PCT/US2005/022812, mailing date Sep. 1, 2006.
International Preliminary Report on Patentability received in International Application No. PCT/US2005/022812, mailing date Jan. 18, 2007.
Office Action dated Mar. 9, 2009, received in U.S. Appl. No. 11/169,825.
Official Communication dated Jun. 10, 2009, received in European Patent Application No. 03814932.
Jouhaneau et al. Glucagon and Insulin Oscillatory Self-Administration in Rats. Physiology & Behavior, 1979, 23: 31-33.
Office Action dated Mar. 6, 2009, received in Chinese patent application No. 200580027047.6 (no translation available).
Examination Report dated Apr. 17, 2009, received in New Zealand Application No. 552860.
File History of U.S. Appl. No. 11/169,825, filed Jun. 28, 2005.
File History of U.S. Appl. No. 11/927,513, filed Oct. 29, 2007.
File History of U.S. Appl. No. 11/927,587, filed Oct. 29, 2007.
File History of U.S. Appl. No. 11/927,621, filed Oct. 29, 2007.
File History of U.S. Appl. No. 11/963,584, filed Dec. 21, 2007.
Office Action dated Dec. 31, 2008, received in U.S. Appl. No. 11/927,513.
Office Action dated Dec. 31, 2008, received in U.S. Appl. No. 11/927,587.
Office Action dated Dec. 29, 2008, received in U.S. Appl. No. 11/927,621.
"Greater Efficiency of Pulsatile Insulin in Type I Diabetics Critically Depends on Plasma Glucagon Levels", *Journal of the American Diabetes Association*, vol. 36, No. 5, pp. 566-570, May 1987.
English translation of Israeli Office Action received in corresponding Israeli Patent Appl. No. 180361, mailed Sep. 13, 2009.

* cited by examiner

METHODS FOR REDUCING THE RISK OF HYPOGLYCEMIA

CROSS-REFERENCE TO RELATED APPLICATIONS

This application is a continuation of U.S. patent application Ser. No. 11/169,825, filed Jun. 28, 2005, which is a continuation-in-part of U.S. non-provisional patent application Ser. No. 10/540,803 filed on Dec. 14, 2005, issued Jan. 1, 2008 as U.S. Pat. No. 7,314,859, entitled "Compositions and Methods for the Prevention and Control of Insulin-Induced Hypoglycemia," which is the U.S. National Phase entry of PCT patent application PCT/US2003/041103 (filed Dec. 23, 2003) and which claims priority to U.S. provisional patent application Nos. 60/436,735 (filed Dec. 27, 2002), 60/454,972 (filed Mar. 14, 2003) and 60/470,346 (filed May 13, 2003). U.S. patent application Ser. No. 11/169,825 further claims the benefit of U.S. provisional patent application 60/584,449 (filed Jun. 29, 2004). The entirety of each of the applications is incorporated herein by reference.

FIELD OF THE INVENTION

The present invention relates to the fields of biology, pharmacology, and medicine. In particular, the invention relates to compositions and methods of using compositions for the control of blood glucose levels.

BACKGROUND OF THE INVENTION

Insulin is produced by the beta cells and glucagon by the alpha cells of the Pancreatic Islets of Langerhans. One of insulin's major effects is to lower blood glucose by suppressing hepatic glucose output and stimulating peripheral glucose uptake. Endogenous insulin levels may be low or undetectable in some patients with diabetes mellitus. Exogenous insulin is usually administered to reduce hyperglycemia in situations where circulating insulin levels are either low or ineffective. Glucagon generally has effects opposite to those of insulin, including, primarily, increasing hepatic glucose output and thereby increasing blood glucose levels. Glucagon levels tend to increase when blood glucose levels fall to abnormally low levels, particularly in patients who utilize exogenous insulin.

Current goals for diabetes management include near normal blood glucose levels to delay or prevent microvascular complications; achievement of this goal usually requires intensive insulin therapy. In striving to achieve this goal, physicians have encountered a substantial increase in the frequency and severity of hypoglycemia in their diabetic patients.

Hypoglycemia, characterized by low blood glucose levels, results in autonomic and adrenergic, as well as neuroglycopenic, symptoms; these symptoms typically are encountered as a result of inadvertent excessive insulin administration. Currently, hypoglycemia is defined as a blood glucose of <70 mg/dl, e.g. greater than 50 or 60 mg/dl. Frequent recurrent bouts of hypoglycemia can be associated with hypoglycemic unawareness which can further contribute to development of hypoglycemia which is sometimes severe. Thus, efforts to achieve normal glucose levels with insulin can result in the development of hypoglycemia of varying frequency and severity in patients. Hypoglycemia and the lack of awareness of its presence are serious complications of insulin therapy that occur with greater frequency and severity when impaired counter-regulatory (anti-insulin) responses are present in diabetic patients. One of the major counter-regulatory hormones that normally responds to hypoglycemia is glucagon. Not infrequently, the glucagon response to acute hypoglycemia is impaired or lost in patients with advanced Type 1 and Type 2 diabetes.

SUMMARY OF THE INVENTION

There remains a need for new methods for treating diabetes and new preparations of insulin and glucagon that reduce the risk of hypoglycemia induced by insulin therapy. The present invention meets this and other needs.

One aspect of the invention provides pharmaceutical compositions comprising both insulin and glucagon in amounts that can be administered to a diabetic patient not only to achieve therapeutically effective control of diabetes but also to prevent hypoglycemia. The formulations can include, for example, formulations suitable for injection, including by subcutaneous (s.c.) administration, formulations suitable for administration orally, formulations suitable for transdermal administration, formulations suitable for ocular administration, and formulations suitable for inhalation. In one embodiment, the compositions comprises between about 0.1 to 5 percent glucagon to insulin by weight for I.V. administration, or a dose equivalent amount for other methods of administration. In another embodiment, the compositions comprise about 0.5 to 2 percent glucagon to insulin by weight when the composition is for I.V. administration, or a dose equivalent amount for other methods of administration. For example, in some embodiments, the glucagon is administered subcutaneously ("s.c.") and 0.1% to 20% glucagon to insulin by weight is administered. In some embodiments, the composition is configured for s.c. administration and comprises 0.1-20 ng/kg/min. of glucagon to 2-20 units of insulin. In some embodiments, the composition is configured for s.c. administration and comprises sufficient glucagon for the administration of 5 to about 20 ng/kg/min. (e.g. more than 5 to 20 ng of glucagon for each kg of a person for each minute of effectiveness) of glucagon. In one embodiment, 5 to about 20 ng/kg/min. of glucagon is administered to 1-20 units of insulin. Administered ratios can be, for example, administered once an hour. In a preferred embodiment, the composition is suitable for administration of more 5 to about 20 ng/kg/min of glucagon for each 1-2 units of insulin administered. As will be appreciated, in some embodiments, the glucagon and insulin can be kept in separate containers and are not administered at the same time, but the appropriate ratios between the two are maintained. In one embodiment, the separate containers are contained in a single device suitable for administration of the glucagon and insulin, for example for administration subcutaneously; in another, two devices are used, one for each agent.

In another aspect, methods to treat diabetes in a human or other mammal without inducing or with a substantially reduced risk of inducing hypoglycemia are provided. In one embodiment, the composition comprising insulin and glucagon is administered to a patient before the symptoms of mild, moderate or severe hypoglycemia are present. In some embodiments, the methods of the invention are practiced to prevent nocturnal hypoglycemia in a Type I diabetic patient being treated with insulin therapy, including intensive insulin therapy. The methods comprise co-administration of insulin and glucagon, wherein said insulin is administered in amounts therapeutically effective for the control of diabetes, and said glucagon is administered in amounts therapeutically effective for the prevention of hypoglycemia, and wherein both insulin and glucagon are preferably administered simultaneously with one another or contemporaneously with one another, i.e., within about four hours of each other (as when regular, LISPRO, and ASPART insulins are used) or within about six to twelve hours of each other (as when longer acting insulins are used), and in any event prior to the onset of clinically observable hypoglycemia. In one embodiment, glucagon is administered before the insulin is administered. In another embodiment, insulin is administered before glucagon is administered. In one embodiment, the method involves maintaining the level of blood sugar above 70 mg/dL and below 180 mg/dL by the co-administration of insulin and glucagon to a diabetic patient. In another embodiment, the method involves administering glucagon s.c. in an amount between about 6 and 18 ng/kg per minute of glucagon. In one embodiment, 1-20 or 2-20 units of insulin are administered to a diabetic patient receiving glucagon in an amount between 6 and 18 ng/kg/min s.c. In another embodiment, the method involves administering between about 8 and 12 ng/kg per minute of glucagon s.c. In one embodiment, 0.1 to 2 or 2-20 units of insulin are administered to a diabetic patient receiving glucagon in an amount between 8 and 12 ng/kg/min. s.c. In another embodiment, the glucagon is administered by a means other than intravenously or subcutaneously, and a dose equivalent to the s.c. dosing provided above is administered.

In another aspect, methods to maintain blood glucose levels in a range that is neither hyperglycemic nor hypoglycemic are provided. These methods comprise the co-administration of insulin and glucagon.

In another aspect, glucagon formulations and modified glucagon suitable for co-administration with insulin in accordance with the present methods are provided.

In another aspect, kits are provided for preventing hypoglycemia. In one embodiment, the kits preferably include insulin, glucagon, and instructions for simultaneously administering the appropriate combination thereof.

In another aspect, the kits include insulin, a long acting form of glucagon, and instructions for use.

In some aspects, methods for restoring or preventing loss of hypoglycemic awareness or sensitivity is provided. The methods comprise administering an amount of glucagon to a patient over a period of time that is sufficient to prevent or restore hypoglycemic awareness to the patient. In one embodiment, the patient is administered insulin concurrently with the administration of glucagon.

In one aspect, a pharmaceutical formulation is provided that comprises insulin in an amount effective for the control of diabetes and glucagon in an amount effective for the prevention of hypoglycemia in a human or other mammal. The pharmaceutical formulation is configured to be administered subcutaneously and the ratio of insulin to glucagon is typically about 1 unit of insulin to between more than 40 milliunits to 200 milliunits of glucagon. In some embodiments, the amount of glucagon is between about 50 and 100 milliunits. In some embodiments, the glucagon is a longer-acting form of glucagon. In some embodiments, the longer-acting form of glucagon contains iodine. In some embodiments, the longer-acting form of glucagon contains zinc. In some embodiments, the longer-acting form of glucagon further comprises protamine.

In another aspect, methods of treating diabetes in a human or other mammal without inducing hypoglycemia are provided. The methods comprise administering insulin in an amount therapeutically effective for the control of diabetes. The insulin can be in an amount between 0.5 and 20 Units of insulin. The methods further comprise administering glucagon in a time and an amount therapeutically effective for the prevention of hypoglycemia. The glucagon can be administered subcutaneously and in an amount between more than 5 and less than or equal to 100 ng per kg of patient per minute of desired glucagon effectiveness. In some embodiments, the amount of glucagon administered is between 6 and 18 ng per kg of patient per minute of desired glucagon effectiveness. In some embodiments, the glucagon is a glucagon with a prolonged duration of action. In some embodiments, the glucagon is contained in a liposomal formulation. In some embodiments, the glucagon is contained in a microsphere. In some embodiments, one administers a formulation comprising both insulin and glucagon. In some embodiments, the insulin and glucagon are contained in a pump that controls administration of a drug to a patient. In some embodiments, the glucagon is administered simultaneously with insulin. In some embodiments, the ratio of glucagon to insulin is about more than 40 to 200 milliunits of glucagon to 1 unit of insulin. In some embodiments, 2 units of insulin are administered. In some embodiments, 10 units of insulin are administered and between 30 and 90 ng per kg per minute of glucagon are administered subcutaneously.

In another aspect, kits for the administration of glucagon and insulin in amounts to prevent hypoglycemia is provided. The kits comprise glucagon and insulin. The glucagon and insulin are in a ratio of 1-20 units of insulin to 32-480 milliunits of glucagon. The kits further comprise a means for administering glucagon subcutaneously and instructions for the administration of insulin and glucagon so that the glucagon prevents a hypoglycemic event. In some embodiments, the concentration of glucagon when completely dissolved in a glycerine solution is more than 500 micrograms per milliliter but less than 2000 micrograms per milliliter. In some embodiments, the glucagon and insulin are in a ratio of 1-3 units of insulin to 32-96 milliunits of glucagon. In some embodiments, the means for administering the glucagon subcutaneously is a pump and said pump is configured to deliver between about 6 to 20 ng/kg/minute of glucagon.

In another aspect, the use of glucagon in combination with insulin in the preparation of a medicament for treatment of diabetes is provided. Glucagon is used in an amount sufficient to prevent an onset of hypoglycemia, wherein a ratio of glucagon to insulin is between more than 40 micrograms and less than 500 micrograms of glucagon to 1-20 units of insulin. In some embodiments, the amount is sufficient to prevent an onset of hypoglycemia unawareness. In some embodiments, the amount of insulin is between 1 and 20 units and the amount of glucagon is between 41 and 200 milliunits. In some embodiments, a ratio of insulin to glucagon is about between 1 and 3 units of insulin to between more than 40 and less than or equal to about 96 milliunits glucagon. In some embodiments, the glucagon further comprises protamine.

DETAILED DESCRIPTION OF THE INVENTION

Figure 1:
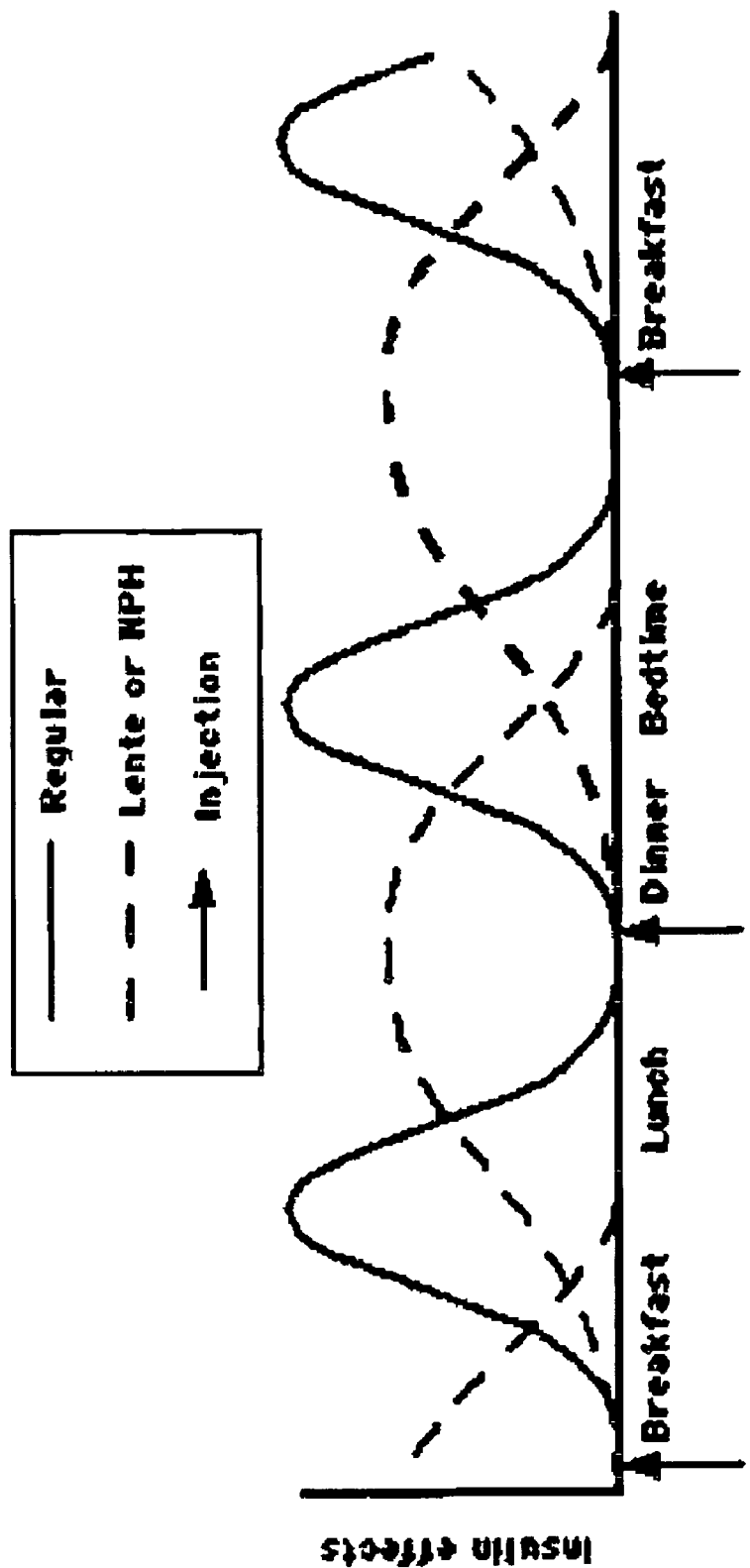
FIG. 1 is a graph illustrating idealized pharmacokinetics for a mixture of regular and intermediate acting (Lente or NPH) insulin.

Methods and compositions are provided that can prevent, or significantly reduce the frequency and severity of, hypoglycemia in insulin-treated diabetic patients (both Type 1 and 2). In one aspect, the methods and compositions are employed to treat diabetes while regulating glucose levels above the levels of hypoglycemia. The methods and compositions can be used to replenish or restore the abnormally low glucagon responses often coincident with insulin administration, thereby preventing hypoglycemia.

One issue that complicates the prevention of hypoglycemia is that repeated hypoglycemic events can lead to a loss of hypoglycemic awareness; thus, even if initially detected by a patient, the patient's ability to identify hypoglycemic symptoms can be compromised or lost over time. Thus, compositions and methods that can prevent or reverse the loss of hypoglycemic awareness are desirable. One method by which this can be achieved is to administer glucagon, or another agent that elevates levels of blood glucose as described herein, in a relatively low dose over the time period in which insulin is to act to prevent the onset of mild hypoglycemia. This can also be used to reverse or prevent a loss of hypoglycemic awareness.

In one embodiment, the invention provides pharmaceutical formulations of two hormones, insulin and glucagon, that are combined in molar ratios that optimize glycemic management and attenuate the incidence of or prevent hypoglycemia. In another embodiment, methods and compositions for the simultaneous but separate administration of insulin and glucagon to achieve this benefit are provided. While the simultaneous administration of two hormones with activities viewed as counteracting would traditionally have appeared to have no beneficial effect, some of the present embodiments arise in part from the realization that such administration achieves the beneficial effect of preventing hypoglycemia by virtue of the buffering or blunting effects of glucagon without diminishing the beneficial effects of glucose regulation provided by insulin. In some embodiments, a low amount of glucagon is continuously administered to a patient that is, has, or is going to receive insulin. Thus, the use of a hyperglycemic agent, such as glucagon, to prevent the onset of hypoglycemia and its associated symptoms due to insulin administration, is contemplated. In some embodiments, a hyperglycemic agent, such as glucagon, is used to prevent the onset of iatrogenic hypoglycemia.

Thus, some of the embodiments provide a method for controlling diabetes with a reduced risk of hypoglycemia by simultaneous administration of insulin and glucagon to a diabetic patient. In one embodiment, a method of preventing hypoglycemia in a diabetic patient who is being treated with insulin and who is not suffering hypoglycemic symptoms is provided, comprising administering glucagon to the patient in an amount therapeutically effective for the prevention of hypoglycemia. In one embodiment, the glucagon is administered simultaneously with the insulin. In another embodiment, the glucagon is administered 10 minutes to hours before additional insulin is administered, and more preferably, 30 minutes to 60 minutes before additional insulin is administered. In other embodiments, the glucagon is administered within about one minute to about four hours after said patient has last been administered insulin. In one embodiment, the prevention of hypoglycemia comprises preventing the symptoms associated with hypoglycemia from becoming evident in a subject. In another embodiment, the prevention of hypoglycemia is achieved through maintaining an average blood glucose level of a subject above about 70 mg/dL, or above about 50-60 mg/dL. Preferably the blood glucose level of the subject is maintained under about 140-200 and at least under about 350 mg/dL. Preferably, the subject's blood glucose level is maintained so that normoglycemia is maintained.

As will be apparent to one of skill in the art upon consideration of the disclosure herein, any of the many different forms of insulin, as well as any of the many different routes of administration of insulin, including those both approved by the FDA and in development, can be used in the presently disclosed methods and formulations. Moreover, any of the currently available formulations of glucagon can similarly be used in the methods and formulations. However, because glucagon has been, prior to the present disclosure, administered only parenterally to control hypoglycemia, the present disclosure provides new glucagon derivatives, new formulations of glucagon and glucagon derivatives, and methods of administering glucagon and glucagon derivatives that are particularly suited to achieve the benefits provided by some of the present embodiments, including delayed and/or extended action glucagon.

While the precise dosage of insulin and glucagon will vary from patient to patient and depend upon a variety of factors, including but not limited to age and sex of the patient, type and severity of diabetes, past history of the patient, including hypoglycemic and hyperglycemic episodes, type of insulin and glucagon employed, and the like, the dosage for any patient can be determined, in light of the present disclosure, by one of skill in the art. The beneficial effects of some of the embodiments can generally be achieved by administering both insulin and glucagon in the ratio of about 1 unit of Insulin to about 0.02-40 milliunits of glucagon (0.02 to 40 micrograms), when the glucagon is administered I.V. A unit of insulin is defined as the term is typically used for the treatment of diabetes, e.g. approximately 34.2 micrograms to approximately 40 micrograms. The amount of insulin can also be measured in international units (IU). A unit of glucagon corresponds to 1 milligram of glucagon. In one embodiment, the ratio is 1 unit of insulin to 0.2 to 4.0 milliunits of glucagon (0.2 to 4.0 micrograms), when the glucagon is administered I.V. and the insulin is administered s.c. When the glucagon is to be administered subcutaneously, 1 unit of insulin can be administered in the amount of 0.02 to 200 milliunits of glucagon for each unit of insulin administered or more than 40 to 200 milliunits of glucagon, e.g. 40 to 200 milliunits per hour to a 100 kg person for each unit of insulin administered. In another embodiment, for each unit of insulin, 48-150 mU, 50-120 mU, or 80-100 mU of glucagon is administered. In a preferred embodiment the glucagon is administered subcutaneously and the ratio is about 1 unit of insulin to more than 5 to about 20 ng/kg glucagon, which amount of glucagon is administered each minute during the period of effectiveness of the insulin dose. In one embodiment, 1 unit of insulin is administered, and the glucagon is administered at a rate of 8-12 ng/kg/min. A standard dose can be created, for example, for treating a 100 kg person for 1 hour in association with 1 unit of insulin. As will be appreciated by one of skill in the art, this dose can be for basal insulin rates. When postprandial levels of insulin are desired, the amount of glucagon in the dose will be increased accordingly. In some embodiments, the glucagon is administered subcutaneously in an amount between more than 5 ng/kg/min. and less than about 20 ng/kg/min. More preferably, the amount is between about 8 and 16 ng of glucagon/kg/min for subcutaneous administration. Of course, one of skill in the art will appreciate that other dose equivalent amounts (i.e., the same effective amount administered through an alternative method) can also be determined in light of the teachings herein. As will be appreciated by one of skill in the art, and as shown in more detail below, this amount can be adjusted to correspond to the amount of glucagon required to prevent hypoglycemia, without inducing hyperglycemia. Thus, in some embodiments, the amount of glucagon administered, even through s.c. administration, is less than the 5-20 ng/kg/min values described as effective in the prevention of insulin-induced hypoglycemia. As will be appreciated by one of skill in the art, while the present disclosure focuses on Type 1 diabetes, similar methods and compositions can be used for Type 2 diabetes. In general, the amount of glucagon can be increased several fold over what is disclosed herein for Type 1 diabetes. For example, Type 2 diabetes can require 1.5 to 5 fold more glucagon, and preferably involves two to three fold more glucagon than Type 1 diabetes.

Any of the currently available forms of insulin, including but not limited to recombinant human soluble (regular) insulin, human insulin analogs, animal insulins, derived, for example, from beef, pork and other species, as well as delayed release forms, including intermediate and long acting insulin may be used for the herein disclosed compositions and methods. Moreover, any of the currently used routes of administration, as well as newer routes in development, can be employed, including but not limited to subcutaneous, intramuscular, and intravenous injection, as well as oral, buccal, nasal, transdermal, sublingual, and pulmonary airway administration. Typical doses and dose ranges for the administration of insulin to control diabetes known in the art are suitable for use in the methods and compositions of some of the embodiments.

For example, prandial short-acting insulins, such as regular insulin and the LISPRO, ASPART, and GLULISINE derivatives thereof, are well known in the art and commonly used to treat diabetes. Such insulins can be used to illustrate the embodiments in a manner applicable to other forms, including but not limited to NPH, LENTE, SEMI-LENTE, DETEMIR, ULTRA-LENTE, and GLARGINE (LANTUS), and pre-mixed formulations of regular and long-acting insulins. In this illustration, the molecular weights ascribed to all three of these prandial short-acting insulins are similar, with LISPRO at 5808. ASPART at 5825.8. GLULISINE at 5823 and regular insulin at 5807. The molecular weight ascribed to glucagon is 3483.

The usual range of prandial insulin injections in Type 1 diabetes can be approximated as two standard deviations from the mean, resulting in an insulin dose range of 2-20 units. More than 95% of Type 1 diabetics will be administered a prandial insulin dose within this range. The three prandial insulins noted above all achieve peak serum concentrations within 1-2 hours after subcutaneous administration and have a duration of effectiveness of about 5 hours.

Currently, hypoglycemia is treated by a single parenteral injection of glucagon in a dose of about 1 mg (1 unit); it has been determined that this dose is a gross excess of the dose actually required to control hypoglycemia. When glucagon is given subcutaneously or intramuscularly, serum glucagon peaks within an hour, and its effects can persist for several hours. However, it appears that currently marketed forms of glucagon are not stable in liquid form, either isolated or in vivo for prolonged periods of time, and in one embodiment, the present invention provides new pharmaceutical formulations of glucagon that are more stable, and new methods for using the stabler forms of glucagon that are currently available but not in widespread use.

It has been discovered, based in part on the respective times to peak serum level and durations of action of the prandial insulins and subcutaneously administered glucagon, that there is a mismatch between subcutaneous insulin and glucagon pharmacokinetics. One embodiment of the present invention provides longer-acting glucagon formulations and derivatives that can be used to correct this mis-match, where desired or of benefit to the patient. "Longer-acting" glucagon, as used herein, refers to a glucagon that has a half-life greater than that of standard glucagon, including both natural extract and rDNA produced synthetic glucagon.

To provide the dose of glucagon required to achieve a duration of effect that is similar to that of the prandial insulins, one can use a dose that approximates the basal replacement dose. The usual basal glucagon replacement dose by IV infusion is 0.5-0.75 ng/kg/min; one can assume that a wider range of glucagon infusions, from as low as 0.10 to 5.00 ng/kg/min (more often, 0.10 to 3.00 ng/kg/min) can be effective, depending on the patient, the insulin dose, the method of administration (e.g. I.V. vs. s.c.), and other factors. For example, in s.c. administration, the present inventors have discovered that the amount of glucagon administered can be higher, as the bioavailability of glucagon administered by subcutaneous infusion can be as low as 10%, and as low as about 35% for bolus subcutaneous administration. Thus, the dose will be increased or decreased accordingly to obtain the equivalent therapeutic effect of administering glucagon at a rate of 5 to 20 ng/kg/min. To match the PK of the insulins, these glucagon infusion rates would be continued for a period of time ranging from 150 minutes to 300 minutes. In some embodiments, the period of time of infusion can last longer than 6 hours, for example 6-7, 7-10, 10-15, 15-20, 20-24 hours, or longer. One can then multiply the replacement rates by the minimum and maximum times to give the total dose/ kg. If one assumes that the typical Type 1 diabetic has a weight within the range of 50 to 100 kg, and that the high and low range dose of subcutaneous prandial insulin injection is between 2 and 20 units, then the insulin/glucagon ratios can be calculated as shown in Table 1 below (showing the ratios for s.c. administration). Of course, this dosage replacement can happen through IV infusion of a dose equivalent amount. In one embodiment, the same calculations described above are used to determine the amount of delayed or extended release forms of glucagon to administer to a patient, taking into account that there will be a lower level of glucagon available initially and a higher amount of glucagon available later. While the amount of glucagon released at any point in time may not be precisely known, enough glucagon is released per unit of time from the administered formulation so that, on average, about 0.1 to 5.0 ng/kg/min. is released into the patient for embodiments in which the glucagon is administered through an I.V. In one embodiment, 0.5, 2, 3. or 4 times as much glucagon may be released on any given unit of time, depending on the patient, the type of diabetes being treated, and the mode of administration.

In some embodiments, and as illustrated in table 1. the glucagon is administered subcutaneously and is administered in an amount between 0.1 to about 30 ng/kg/min., about 4.0 to about 20 ng/kg/min., about more than 5.0 to about 30 ng/kg/min, about 6 to 25 ng/kg/min, about 6 to 20 ng/kg/min, or about 8.0 to about 12.0 ng/kg/min.

glucagon can induce elevated blood glucose levels that approach hyperglycemia, as such, it is likely that lower dose ranges can be sufficient to prevent hypoglycemia, without risking hyperglycemia. Lower ranges or doses can be from 0.09% to 188% of the weight of insulin, for example. As will be appreciated by one of skill in the art, the weight of the patient can vary, from infants, e.g. 2 kg to full adults, e.g. 150 kg to 200 kg, or more.

In other embodiments, the amount of glucagon administered can be described as an amount of glucagon by weight or activity independent of the amount of insulin administered; for example, in one embodiment, the amount of glucagon administered is 200-300 or 360-900 micrograms over a nine hour period. In one embodiment, the amount of glucagon administered is between about 22 to 33 micrograms in one hour. In one embodiment, the glucagon administered ranges from more than 5 ng/kg/min to about 30 ng/kg/min s.c. In some embodiments, the amount is about 0.1 ng/kg/min to about 30 ng/kg/min. In one embodiment, the amount is about 8 to about 16 ng/kg/min, or about 12 ng/kg/min. s.c. In some embodiments, substantially lower values can be sufficient as well, depending upon the circumstances and mode of administration.

In one embodiment, hypoglycemia is a blood glucose level of less than about 50-60. and generally less than about 70 mg/dL, and hyperglycemia is a blood glucose level more than about 140 to 200 mg/dL. In one embodiment, excessive hyperglycemia is defined as a blood glucose level above 350

TABLE 1

Insulin (sc)/Glucagon (sc) Weight Ratios (ng/ng) and Inverse Ratio [% terms]

| | Patient Weight | | | |
|---|---|---|---|---|
| | 50 kg | 50 kg | 100 kg | 100 kg |
| | | Duration of Gluc. Admin. | | |
| | 150 min | 300 min | 150 min | 300 min |
| 2 U Ins/6 ng/kg/min Gluc | 1.8 [56.3%] | 0.9 [112.5%] | 0.9 [112.5%] | 0.4 [225%] |
| 20 U Ins/12 ng/kg/min Gluc | 8.9 [11.3%] | 4.4 [22.5%] | 4.4 [22.5%] | 2.2 [45%] |
| 2 U Ins/18 ng/kg/min Gluc | 0.6 [168.8%] | 0.3 [337.5%] | 0.3 [337.5%] | 0.1 [675%] |
| 20 U Ins/6 ng/kg/min Gluc | 17.8 [5.6%] | 8.9 [11.3%] | 8.9 [11.3%] | 4.4 [22.5%] |
| 2 U Ins/12 ng/kg/min Gluc | 0.9 [112.5%] | 0.4 [225%] | 0.4 [225%] | 0.2 [450%] |
| 20 U/18 ng/kg/min Gluc | 5.9 [16.9%] | 3.0 [33.8%] | 3.0 [33.8%] | 1.5 [67.5%] |

Explanation of Table Entries:
For 2 U Ins/6 ng/kg/min Gluc: Means that a TOTAL of 2 Units of Insulin are administered over the given infusion period, and that Glucagon is administered over the period of infusion at a rate of 6 ng/kg/min. The two number in the Table given for a 50 kg person over 150 minutes are the weight ratios of Insulin and Glucagon (absolute terms) and the weight ratios of Glucagon to Insulin in percentage terms, (e.g., 1.8 = 80000 ng (2 units of Insulin)/750 ng (50 × 150*6 Glucagon); 56.3% = 1/1.8 in percentage terms = inverse ratio).

In Table 1. the amount of glucagon administered ranges from 5.6 to 675% of the amount (in weight) of insulin administered; for many patients, however, the glucagon is administered at, or is present in a composition at <225% of the weight of insulin. As will be appreciated by one of skill in the art, the amount of glucagon administered can vary depending upon many factors. Thus, ranges of the percent of glucagon to insulin can vary between 5.6 to 675%, e.g. more than 188% to less than 675%. In one embodiment, the amount of glucagon administered is expressed as a ratio to the amount of insulin administered; for example, the ratio of glucagon administered can be from 5.6 to 11.3 percent of the amount of insulin administered. In some embodiments, the amount of glucagon administered is 112 to 225% of the amount of insulin administered. As shown in Example 7 below, these amounts of mg/dL. The ratio of glucagon to insulin and amounts of each is set, in accordance with the methods of the invention, to keep the blood sugar level effectively between the hypoglycemic level and the hyperglycemia level. In another embodiment, the blood sugar level is maintained between the hypoglycemic level and the excessive hyperglycemia level. In another embodiment, the blood sugar level is maintained between the hyperglycemia level and the excessive hyperglycemia level. As will be appreciated by one of skill in the art, the level need not be observed precisely, and minor dips below or peaks above these ranges are permissible. In one embodiment, the dose to be administered to a patient is therapeutically equivalent to a dose of 0.5 to 0.75 ng/kg/min of glucagon administered I.V. or is therapeutically equivalent to a dose of above 5 to about 20 ng/kg/min. s.c., i.e., 8-16 ng/kg/min of glucagon via s.c. administration. In some embodiments, 0.1 to 5 ng/kg/min. is all that is needed for the subcutaneous administration, for the prevention of the onset of hypoglycemia. In some embodiments, the same amount of glucagon (or effective ratio of glucagon to insulin) is used, even if an agent other than insulin is used to lower or control blood sugar levels. Thus, in some embodiments, the method of the invention may be practiced with an agent other than insulin, as the co-administration of glucagon, in light of the present disclosure, with a hypoglycemic agent is contemplated. Similarly, in some embodiments, a hyperglycemic agent other than glucagon is used to prevent the onset of hypoglycemia in insulin treated diabetics. In some embodiments, neither insulin nor glucagon is used, and a diabetic patient is simultaneously administered both a hyperglycemic agent (an agent that causes blood sugar levels to rise) and a hypoglycemic agent (an agent that causes blood sugar levels to decline).

As will be appreciated by one of skill in the art in view of the instant disclosure, the amount of glucagon or insulin administered to a patient can vary depending upon the mode of administration For example, the amount of glucagon (or ratio of insulin to glucagon) to be added can be described in terms of the amount to be administered via an I.V. (as in PCT Pub. No: WO 2004/060387. incorporated herein by reference). This amount can differ greatly depending upon how the glucagon is to be administered, e.g. subcutaneously or via inhalation. For simplicity, the amount of glucagon required to achieve an equivalent result can be described as a "dose equivalent." For example, a "10 ng/kg/min. s.c. dose equivalent" is the amount required to achieve the same result as would be achieved by administering 10 ng/kg/min. to a patient subcutaneously. A "s.c. dose equivalent for I.V. administration" is the amount of glucagon administered intravenously that is required to obtain the same amount of glucose or glucagon in the blood achieved by subcutaneous administration of the amount of glucagon. Thus, in the latter phraseology, the first method of administration describes what the dose administered is going to be an equivalent to using another mode of administration, and the second mode of administration recited is the mode of administration actually employed. An I.V. dose equivalent of glucagon administered subcutaneously will typically be more than the amount recited for I.V. administration, as can be seen by comparing the table above to Table 1 in PCT Pub. No. WO 2004/060387. For example, a unit to be delivered I.V. is in some patients 0.1 ng/kg/min., while the amount for the same effect to be delivered subcutaneously can be 8 ng/kg/min. in those patients. In addition, in a clinical trial described in the Examples below, the amounts of glucagon required to be administered to induce hyperglycemia in an insulin-treated diabetic were for some patients in the 8-16 ng/kg/min. range (although lower doses were seen to be effective as well), so the amounts of glucagon required merely to prevent hypoglycemia will be below that range in some patients. Given the present disclosure, one of skill in the art will be able to determine the appropriate amount in each circumstance.

As will be appreciated by one of skill in the art, the "amount of glucagon administered" is not necessarily the amount of glucagon that actually enters the bloodstream of a patient. Rather, for example, administering 9 ng/kg/min. s.c. of glucagon to a patient means that an initial solution of an initial known amount was created, and based on that amount, 9 ng/kg/min. of glucagon is administered to a patient. If there is a loss or degradation of the glucagon prior to administration, then less glucagon enters the patient, and if there is a loss or degradation of glucagon as it progresses to the patient's bloodstream and tissues, the effective therapeutic dose is lower still. As will be appreciated by one of skill in the art, the actual amount of glucagon that is active and enters the patient's circulation will in such instances be less than, in this example, 9 ng/kg/min.

One of skill in the art, given the present disclosure, can determine the dose equivalent for various methods or modes of administration. This dose equivalent can also vary depending on inter- and intrapatient variability and the bioavailability of the drug. For example, if one assumes glucagon administered through an I.V. is 100% bioavailable, then certain glucagon formulations administered through a s.c. bolus can have about 35% bioavailability, while the same glucagon formulation administered by continuous subcutaneous infusion can have a bioavailability of 10%, as shown with patient data in the Examples below. Additionally, differences between the method of administration of insulin and of glucagon can also be taken into account and determined through the methods and examples provided herein. One way this can be determined is through various assays of insulin, glucose and glucagon in a patient following various routes of administration of the glucagon, e.g., as illustrated in Example 7.

The pharmaceutical compositions for use in many embodiments of the invention can comprise those compositions useful in conventional methods for the control of diabetes and treatment of hypoglycemia. Such conventional methods, as that phrase is used herein, include those approved by the FDA, those in development, and those described in Diagnosis and Management of Type II Diabetes, by S. V. Edelman and R. R. Henry (5$^{th}$ Ed. PCI Publishers), the entire text of which is incorporated herein by reference, and Chapters 7 and 8 of which are especially pertinent. As used herein, a pharmaceutical formulation or pharmaceutical composition may contain a pharmaceutically acceptable excipient, diluent or carrier. The phrase "pharmaceutically acceptable" means that the carrier, diluent or excipient is compatible with the other ingredients of the formulation and administration equipment and not deleterious to the recipient thereof Pharmaceutically acceptable excipients are well known in the art. See, e.g., *Remington: The Science and Practice of Pharmacy* (19th edition, 1995. Gennavo, ed.).

In one embodiment, the glucagon or similar substance is administered in a buffer. Appropriate buffers are those that maintain the mixture at a pH range from about 6.0 to about 9.0. but which do not interfere with the function of glucagon. Examples of buffers include, but are not limited to, Goode's buffers, HEPES, Tris, ammonium acetate, sodium acetate, Bis-Tris, phosphate, citrate, arginine, histidine, and Tris acetate. The selection of one or more appropriate buffers is within the skill of one of ordinary skill in the art.

The control of diabetes by insulin therapy, as well as the control of hypoglycemia by glucagon therapy, can involve parenteral administration of the insulin or glucagon. Parenteral administration may be performed by subcutaneous or intramuscular injection by means of a syringe, optionally a pen-like syringe. Some of the embodiments of the methods can be practiced using such methodology, although, as noted above, it may be preferable in some instances to provide glucagon in a manner that ensures that its duration of action more closely matches that of the insulin employed such that the glucagon is present when the risk of hypoglycemia is greatest—typically a relatively long time after eating but still within the period in which the insulin administered continues to exert its effect.

Where subcutaneous administration of insulin and glucagon are desired, a variety of methods may be employed to achieve the benefits of diabetes control and prevention of hypoglycemia. In one such method, a glucagon with a shorter duration of action than the insulin is administered within about one to four hours after the insulin is administered. This method provides benefit in that most hypoglycemic episodes begin several hours after the patient has last eaten, and many patients administer insulin shortly before a meal. Thus, by delivering the glucagon a few hours after the insulin, but prior to the onset of hypoglycemic symptoms, one can achieve the benefits of the methods of the invention. Certain embodiments provide methods for controlling diabetes with reduced risk of inducing hypoglycemia by administering insulin in continuation with a long acting glucagon and formulations thereof Thus, in one embodiment, compositions having a long acting form of glucagon are provided.

In general, long acting forms are also known as extended release, prolonged release or controlled release (or similar term) forms. In one embodiment, delayed or slow acting glucagon is a particular form of an extended or long release form of glucagon. Delayed acting glucagon is within the general class of long acting glucagon, as delayed or slow acting glucagon will allow for glucagon activity to occur after a period of time following the administration of glucagon; however, delayed acting glucagon is effective in lower amounts at the initial administration and increases in effectiveness over time. The glucagon itself may be long acting in nature, or it may be combined with other components that allow its release over an extended amount of time.

In another embodiment, the insulin and glucagon can be administered simultaneously, with the insulin and optionally the glucagon delivered parenterally, typically by subcutaneous injection. In this method, a glucagon with a longer duration of action is preferably employed, or the glucagon is administered by a route that provides a longer duration of action, e.g., as by continuous infusion, as illustrated in the Examples below.

Such glucagon includes, but is not limited to, the glucagon, glucagon formulations, and routes of administration described in U.S. patent application publication No. 2002114829 and U.S. Pat. Nos. 6,197,333 and 6,348,214. which describe liposome formulations of glucagon that provide for reduced dosage effect and are long acting; PCT patent publication No. WO0243566. which describes the delivery of glucagon via trans-dermal patch; U.S. Pat. No. 5,445,832. which describes a long-acting glucagon formulation in polymeric microspheres; PCT patent publication No. WO0222154. which describes a slow-release glucagon that can have a duration of action measured in weeks; and U.S. Pat. No. 3,897,551 and Great Britain Patent No. 1,363,954. which describes the prolongation of glucagon duration by iodination (each of these publications are incorporated herein by reference in their entireties.) In an embodiment, the glucagon is administered as a slow-release or depot formulation (e.g., comprising polyethylene glycol).

There are many techniques known to those skilled in the art for modifying the release and/or pharmacokinetic characteristics of proteins, include the modification of the amino acid sequence at the site corresponding to the metabolic deactivation point associated with the protein. These techniques and compositions include, "pegylation" or PEG-modification of the protein (see, for example, PCT Patent publication Nos. WO0232957, WO9831383. and WO9724440. EP patent publication Nos. EP0816381 and EP0442724. and U.S. Patent Publication Nos. 2002/0115592; U.S. Pat. Nos. 5,234,903; and 6,284,727); other polymer encapsulations (see EP patent publication No. EP0684044); lipophilic modification (see U.S. Pat. Nos. 5,359,030; 6,239,107; 5,869,602; and 2001/0016643; EP patent publication No. EP1264837; and PCT Patent publication Nos. WO9808871 and WO9943708; formulating into liposomes (see U.S. Pat. Nos. 6,348,214 and 6,197,333); serum albumin modification (discussed in more detail below and in PCT Patent publication Nos. WO02066511 and WO0246227 and U.S. Pat. No. 4,492,684); formulating in the form of emulsions, microspheres, microemulsions, nanoencapsulation and microbeads (see U.S. Pat. Nos. 4,492,684; 5,445,832; 6,191,105; 6,217,893; 5,643,604; 5,643,607; and 5,637,568); formulations involving ligands (see PCT Patent publication No. WO0222154); and iodination (see U.S. Pat. No. 3,897,551).

In one embodiment, an iodination method of increasing half life (as described in U.S. Pat. No. 3,897,551; see form I3G) is employed. Iodinated glucagon has extended activity (measured in terms of elevated glucose levels) of between 1 and 3 hours, depending on the extent of iodination. In one embodiment LISPRO insulin and I3Glucagon are admixed so that the modified glucagon is present at approximately 1.5% by weight of the insulin in the mixture (keeping the concentration of insulin per ml in the LISPRO formulation constant). Because of the longer lasting effect of the modified glucagon, a smaller proportion of glucagon to insulin by weight will be required to prevent hypoglycemia in some patients.

Another form of a long acting glucagon is a zinc-protamine-glucagon formulation. Examples of such Zinc protamine-glucagon formulations are known in the art (See, for example, Kaindl et al., Verh Dtsch Ges Inn Med. 1972;78: 1099-101; Kaindl and Kuhn, Z Gesamte Inn Med. Dec. 15, 1972;27(24):1097-8; Christiansen and Tonnensen, Med Scand. 1974 December;196(6):495-6; Gamba et al., Minerva Med. Nov. 3, 1977;68(53):3613-26; Kollee et al., Arch Dis Child. 1978 May;53(5):422-4; Kalima and Lempinen, Ann Chir Gynaecol. 1980;69(6):293-5; Aynsley-Green et al., Arch Dis Child. 1981 July;56(7):496-508; Schmid and Wietholter, Dtsch Med Wochenschr. Nov. 26, 1982;107(47):1809-11; Day and Mastaglia, Aust N Z J Med. 1985 December;15(6): 748-50; Cederblad et al., Horm Res. 1998;50(2):94-8; all herein incorporated in their entirities by reference.

Additionally, Pichler et al. (Wien Klin Wochenschr 19:91 (2):49-51 (1979)) demonstrated that a zinc protamine form of glucagon had a maximal effects up to 3 hours after the actual administration of the drug, and only displayed a decrease in activity after the fourth hour. Thus, the effective half-life of zinc protamine glucagon is in the range of hours.

In one embodiment, glucagon is combined with zinc without protamine, as described in Tarding et al., (European Journal of Pharmacology, 7:206-210 (1969), hereby incorporated in its entirety by reference). This also results in a long acting form of glucagon. In one embodiment, the mixture involves a 1 to 2 ratio of zinc to glucagon.

In one embodiment, the zinc protamine glucagon is made in a manner similar to how zinc protamine insulin is made, apart from the replacement of insulin with glucagon. In one embodiment, zinc glucagon and zinc protamine glucagon is made as described in Tarding et al. (European Journal of Pharmacology 7:206-210 (1969)). For example, zinc glucagon can be made by suspending freeze-dried zinc glucagon crystals in a zinc acetate buffer, for a final concentration of 1 mg glucagon/ml, 0.05 mg zinc/ml. Alternatively, the zinc protamine glucagon can be prepared by suspending freeze-dried zinc glucagon crystals in a zinc acetate buffer containing protamine to a final concentration of 2 mg glucagon/ml, 0.15 mg zinc/ml, and 0.5 mg protamine/ml.

Another example of an agent that can be included with glucagon in compositions useful in the present methods includes a protamine sulfate, as described in combination with GLP-1 in U.S. Pat. No. 6,703,365. (issued Mar. 4, 2004.

to Galloway et al.). The GLP-1 combination therein disclosed displays an increased half-life and an increased shelf life as well. Any glucagon which displays an increased half-life can be useful in the present methods and compositions.

Another means by which the half-life of the protein may be extended is through the use of "serum binders", such as can be achieved through the conjugation of albumin to glucagon by a connector. In one embodiment, the glucagon contains a moiety which allows it to attach itself to albumin in vivo. Alternatively, the glucagon may be modified such that it is able to connect to a connector, which will then allow the glucagon molecule to be associated with a protein such as albumin in vivo. Thus, the modified glucagon can be directly added to a patient, where it will subsequently bind to albumin in the host, which will in turn result in the extension of the useful life of glucagon in the system. This approach has been described for other purposes for GLP-1 in U.S. Patent Publication 20030108568. published Jun. 12, 2003 to Bridon et al., as well as for various other proteins (See, for example, U.S. Pat. No. 6,277,863. issued Aug. 21, 2001 to Krantz et al., U.S. Pat. No. 6,500,918. issued Dec. 31, 2002. to Ezrin et al., U.S. Pat. No. 6,107,489. issued Aug. 22, 2000. to Krantz et al., U.S. Pat. No. 6,329,336. issued Dec. 11, 2001. to Bridon et al., and U.S. Pat. No. 6,103,233 issued Aug. 15, 2000. to Pouletty et al., all of which are incorporated by reference in their entireties). In one embodiment, the binding between glucagon and albumin occurs with the aid of biotin and avidin or streptavidin. In another embodiment, glucagon can be attached to other proteins through the use of maleimide groups and sulfur groups. The glucagon can be attached to any suitable protein, not only albumin.

In one embodiment, a prolonged release form of glucagon is a gel or fibril based form of glucagon. These may be prepared as described in Gratzer and Davies (European J. Biochem., 11:37-42 (1969), hereby incorporated in its entirety by reference.)

Other forms of prolonged release glucagon are also contemplated for use in the present methods. Long release preparations may be made using polymers to complex or absorb the glucagon. The controlled delivery may be exercised by selecting appropriate macromolecules and the concentration of macromolecules as well as the methods of incorporation to control release. For example, diffusion controlled systems may be used. Examples of such materials include particles of a polymeric material such as polyesters, polyamino acids, polyvinylpyrrolidone, methylcellulose, carboxymethylcellulose, hydrogels, poly (lactic acid), or ethylene vinylacetate copolymers. Alternatively, instead of incorporating a compound with these polymeric particles, it is possible to entrap a compound of some of the embodiments in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in Remington's Pharmaceutical Sciences (1980). In one embodiment, the rate of dissolution of the drug is primarily controlled by the dissolution of a shell, which encapsulates the drug.

In one embodiment, an osmotic pump system is used to provide a prolonged release of glucagon, allowing the rate of release of the drug to be controlled by the inflow of water across a semipermeable membrane into a reservoir that has an osmotic agent. In another embodiment, ion exchange resins are used to control the release of glucagon.

In one embodiment the extended release form of glucagon is a preproglucagon [Lund, et al., Proc. Natl. Acad. Sci. U.S.A. 79:345-349 (1982)]. This polypeptide is subsequently processed to form proglucagon, which is subsequently cleaved into glucagon and a second polypeptide (Patzelt, C., et al., Nature, 282:260-266 (1979)). Thus, by administering this form of prepro- or proglucagon, one is able to delay the onset of the activity of the glucagon.

In one embodiment, glucagon is administered in a form that allows substantially no release of active glucagon initially, and then allows for a small amount of release of glucagon over time. Such a form of glucagon is useful when prolonged periods between drug intake will occur and the desired result is an effect towards the end of the prolonged period, for example, during nocturnal periods. The form may be inherent in the glucagon protein itself, i.e., a semi-synthetic glucagon variant, due to compositions associated with the protein, due to the formulations in which the glucagon is administered, due to the route and method by which the glucagon is administered, as well as other reasons as described herein.

Glucagon with a low activity level is desirable in some circumstances. As the delivery of precise amounts of small volumes can be difficult, especially over prolonged periods of time, compositions of glucagon comprising components that lower the activity of glucagon may be desirable in some situations to allow the administration of larger volumes of sample. Alternatively, variants or mutants of glucagon with a lower activity level can be used to achieve this result. The term "glucagon" can encompass both wild-type glucagon and variants or derivatives of glucagon.

In some embodiments, a combination of an insulin component and a slow release form of a glucagon provided by the invention is employed in the methods of the invention. As will be appreciated by one of skill in the art, the combination may be achieved through a single or multiple formulations and single or multiple means of administering the insulin component or the glucagon component.

In one embodiment, parenteral administration is performed by means of an infusion pump. A variety of insulin pumps are available and in common use that are suitable for delivery of the insulin and glucagon compositions (as well as suitable for the delivery of insulin, with glucagon being delivered by another route, such as transdermal). Such pumps include, for example and without limitation, the pumps marketed by Medtronic (such as the MiniMed), Animas Corporation, Disetronic, and Dana. The glucagon can optionally be administered with the insulin, and a glucagon with a short duration of action can be employed, as the glucagon can be administered as necessary. In one embodiment, the glucagon can be administered intravenously at a rate of 0.5-0.75 ng/kg/min or within the wider range of about 0.10-5 ng/kg/min, alternatively, within the range about 0.10-3 ng/kg/min. or in an amount that is an intravenous dose equivalent. In a preferred embodiment, the glucagon is administered subcutaneously and is administered in an amount between about 4 and 30 ng/kg/min, about more than 5.0 up to 25 ng/kg/min, about 8.0 to 20 ng/kg/min, or about 8.0 to 12.0 ng/kg/min. Lower amounts of glucagon can be administered (0.1-5 or 2-5 ng/kg/min.) subcutaneously to prevent hypoglycemia in some patients. In one embodiment a dose will prevent hypoglycemia without causing excessive hyperglycemia. Hyperglycemia is a blood glucose above the normal range. Glucagon can elevate blood glucose above where it would be without the administration of exogenous glucagon, and in a preferred embodiment, the dose administered is one that is still protective against hypoglycemia but only minimally elevates blood glucose above the levels maintained in the patient when not suffering from hypoglycemia.

Thus, in one embodiment, the present invention provides a new drug delivery device, a pump suitable for the delivery of insulin for the control of diabetes, and for the delivery of glucagon for the control of hypoglycemia in a human, i.e., the pump contains both insulin and glucagon. The pump may include a reservoir containing both insulin and glucagon. In other embodiments, the pump includes insulin and glucagon in two separately controlled reservoirs. A method of controlling diabetes in a human patient to reduce the risk of hypoglycemia is provided, said method comprising administering both insulin and glucagon to the diabetic patient using a pump of one of the embodiments described above.

In another method, either the insulin or the glucagon or both is provided in a formulation that is a powder or a liquid suitable for administration as a nasal or pulmonary spray or for ocular administration. A variety of such formulations are known for insulin and glucagon, and the present disclosure provides methods for using these known formulations for administering either one independently, as well as for administering the corresponding formulations of the embodiments that comprise both insulin and glucagon to control diabetes with a reduced risk of inducing hypoglycemia.

Methods and formulations for nasal, pulmonary, or ocular administration include those in PCT patent publication Nos. WO0182874 and WO0182981. which describe aerosolized insulin and glucagon; European patent publication EP1224929 and U.S. Pat. No. 6,004,574. which describe an inhaled glucagon with melezitose diluent; U.S. Pat. No. 5,942,242. which describes formulations of insulin and formulations of glucagon suitable for nasal administration; U.S. Pat. No. 5,661,130. which describes formulations suitable for ocular, nasal and nasolacrimal or inhalation routes of administration; U.S. Pat. No. 5,693,608. which describes methods and formulations for the nasal administration of insulin and for glucagon; U.S. Pat. No. 5,428,006. which describes methods and formulations for the nasal and other mucosal administration of insulin and for glucagon; U.S. Pat. No. 5,397,771. which describes methods and formulations for the mucosal administration of insulin and of glucagon; U.S. Pat. No. 5,283,236. which describes methods and formulations for the ocular administration of insulin and of glucagon; and European patent publication EP0272097. which describes a formulation of glucagon for nasal administration. In addition to these formulations, the methods of delivering these formulations as described are also contemplated.

In one embodiment, compositions and methods are provided for controlling diabetes with a reduced risk of inducing hypoglycemia by administering insulin and glucagon, in which one or both of the insulin and glucagon is administered transdermally, e.g. from a patch, optionally a iontophoretic patch, or transmucosally, e.g. bucally. Manufacture and use of transdermal delivery devices are well known in the art (see, e.g., U.S. Pat. Nos. 4,943,435 and 4,839,174; and patent publication no. US 2001033858). The transdermal delivery of glucagon, and a patent publication describing transdermal formulations of glucagon, has been cited above, and U.S. Pat. No. 5,707,641 describes methods and formulations for the transdermal delivery of insulin.

Moreover, some embodiments of the methods can be practiced by oral administration of both insulin and/or glucagon in the therapeutically effective amounts and their dose equivalents described herein. Methods and formulations for the oral administration of insulin and of glucagon include those described in PCT patent publication No. WO9703688.

The insulin and/or glucagon employed in the methods and formulations can be supplemented with or replaced by compounds and compositions that have similar activities or effects. For example, glucagon may be replaced with glucagon mimetics or variants of glucagon.

Insulin can be replaced or supplemented with hypoglycemic agents, including but not limited to Insulin Sensitizers, DPP IV inhibitors, and GLP1 analogs, insulin secretagogues including, but not limited to, sulfonylureas such as Acetohexamide (DYMELOR), Chlorpropamide (DIABINESE), Tolazamide (TOLINASE), Tolbutamide (ORINASE), Glimepiride (AMARYL), Glipizide (GLUCOTROL), Glipizide Extended Release (GLUCOTROL XL), Glyburide (DIABETA, MICRONASE), Glyburide Micronized (GLYNASE, PRESTAB); Meglitinides such as Nateglinide (STARLIX) and Repaglinide (PRANDIN); Gastric Inhibitory Polypeptide (GIP); Glucagon-like peptide (GLP)-1; Morphilinoguanide BTS 67582; Phosphodiesterase inhibitors; and succinate ester derivatives; insulin receptor activators; insulin sensitizing Biguanides such as Metformin (GLUCOPHAGE), Thiazolidinediones (TZD) such as Troglitazone (REZULIN), Pioglitazone (ACTOS), and Rozigltazone (AVANDIA); Non-TZD peroxisome proliferator activated receptor γ (PPARγ) agonist GL262570; Alpha-glucosidase inhibitors such as Acarbose (PRECOSE) and Miglitol (GLYSET); Combination agents such as Glucovance (GLUCOPHAGE with GLYBURIDE); Tyrosine Phosphatase Inhibitors such as Vanadium, PTP-1B inhibitors, and AMPK activators, including 5-aminoimidazole-4-carboxamide ribonucleoside (AICAR); and other agents such as Exendin (EXENATIDE (synthetic exendin-4)) and Amylin (SYMLIN® (pramlintide acetate)), D-Chiro-Inositol, altered peptide ligands (NBI-6024), Anergix DB complex, GABA inhibit melanocortin, Glucose lowering agent (ALT-4037), Aerodose (Aerogen), insulin mimics, Insulin-like growth factor-I alone or in a complex with BP3 (SOMATOKLINE), metoclopramide HCL (Emitasol/SPD 425), motillde/Erythromycin analogs, and GAG mimetics.

In one embodiment, variants of glucagon are contemplated. Such variants may comprise a single or many amino acid changes, for example, from one to all of the amino acids may be changed, relative to the native human glucagon sequence, so long as the resulting variant functions as required herein. In one embodiment, the HELIX content is adjusted at the C-terminus, as well as partial agonists are combined to provide more of a "basal" input. In one embodiment, transient PEG-modifications at the N-terminus, to control activation can be complemented with mutations introduced at the C-terminus, for controlling affinity. Examples of such variant glucagon molecules, and their resulting characteristics and activities, are available in the art. For example, Sturm et al., (J. Med. Chem. 41:2693-2700 (1998)) teaches a general structural function relationship for some of the salt bridges in glucagon. In one embodiment, the variant glucagon has a Lys substitution at positions 17 and 18. and a Glu substitution at position 21. resulting in a variant with a 500 percent binding affinity and a 700 percent relative potency. In one embodiment, the variant glucagon amide has only a Lys substitution at position 17. resulting in a variant with a 220 percent binding affinity and a 230 percent potency. In another embodiment, the variant glucagon amide has a Nle substitution at position 17. a Lys substitution at position 18. and a Glu substitution at position 21. resulting in a variant with 150 percent binding affinity and a 300 percent potency. In another embodiment, the variant glucagon molecules display low binding ability or low activity. Thus, for example, a glucagon amide variant with a lysine at position 18 may be used, as it only has 36 percent of the normal binding affinity and only 12 percent of the normal potency. Another example would be a glucagon variant with a Phe at position 18, which has only 4.7 percent of the normal binding affinity and 0.9 percent of the relative potency.

In one embodiment the only pharmaceutically active components of the formulation are insulin and glucagon. In one embodiment, the pharmaceutical composition (e.g., containing both insulin and glucagon) is not formulated as an aerosol and/or does not contain troglitazone hydrochloride (and may not contain any thiazolidinedione). In an embodiment, the formulation is not administered orally and/or is not administered nasally. In one embodiment, the pharmaceutically active components of the formulation are administered transdermally, but not through a patch. For example, the active components can be administered through the use of a cream.

As discussed above, the simultaneous effective administration of low doses of glucagon together with insulin can help prevent insulin-induced hypoglycemic events. The prevention of these events will have various beneficial results.

Repeated mild to moderate hypoglycemic events can result in a loss of hypoglycemic awareness by the subject. Thus, the subject may no longer be able to detect that he or she is actually experiencing a hypoglycemic event, increasing the risk that more hypoglycemic events can occur. Thus, the above compositions and methods can be optimized so as to reduce the risk of this occurring. The above ratios of insulin and glucagon and amounts of glucagon recited for the prevention of hypoglycemia can be sufficient to treat this condition, and the methods of the invention include methods for adjusting the amount administered to achieve the desired therapeutic effect for a particular patient, mode of delivery, or formulation. In some embodiments, the combination of glucagon and insulin is administered to a patient to prevent the loss of hypoglycemic awareness by the subject. In other embodiments, the glucagon and insulin are administered so as to restore hypoglycemic awareness to the subject. This can be achieved by administering an amount of glucagon so that additional episodes of hypoglycemia are reduced or prevented. The amount can vary, e.g. 8-16 ng/kg/min. administered subcutaneously or 0.1-5 ng/kg/min intravenously.

As will be appreciated by one of skill in the art, these therapies and compositions can be useful not only for people with diabetes but with anyone taking insulin or other hypoglycemia inducing agent.

As will be appreciated by one of skill in the art, not every episode of mild or moderate hypoglycemia needs to be prevented. The amount or percent of events inhibited can vary by the particular situation and subject and can include inhibiting 2-5, 5-10, 10-20, 20-30, 30-40, 40-50, 50-60, 60-70, 70-80, 80-90, 90-99. or 99 percent to all of the mild/moderate hypoglycemic events. Additionally, hypoglycemia need not be prevented in every case and can be delayed in some embodiments. Any amount of delay can be useful, for example, a delay of 1-10, 10-30, 30-60, 60-120, 120-300, 300-600 or more minutes. Alternatively, a delay of an additional 1-20, 20-60, 60-100, 100-200. or 200% to 10 fold Additionally, not all of a patient's sensitivity to hypoglycemia needs to be restored or preserved, e.g. 1-10, 10-20, 20-30, 30-40, 40-50, 50-60, 60-70, 70-80, 80-90, 90-99, 99-100% can be restored or prevented from loss. "Hypoglycemic sensitivity" or "hypoglycemia unawareness" can be based on the individual's ability to detect the occurrence of a hypoglycemic event. For example, hypoglycemia unawareness can be an inability to detect 1-20, 20-40, 40-50, 50-70. or more percent of the hypoglycemic events (e.g., glucose levels fall below 50 mg/dL in the blood). Alternatively, the inability to detect a particular symptom of hypoglycemia can also be used to determine hypoglycemia unawareness and how successfully it is being treated. Signs and symptoms include, for example, shakiness, dizziness, sweating, hunger, headache, irritability, pale skin color, sudden moodiness or behaviour changes, clumsy or jerky movements, difficulty paying attention, confusion, and a tingling sensation around the mouth. A description of various possible categories of hypoglycemia can be found in "Defining and Reporting Hypoglycemia in Diabetes" *Diabetes Care,* 28:1245-1249 (2005), hereby incorporated by reference in its entirety. In particular, symptomatic, asymptomatic, and probably symptomatic hypoglycemia involve plasma glucose levels below or equal to 70 mg/dl. As noted herein, in some situations, lower levels of blood glucose can also be used as a threshold.

Kits

In some embodiments, the compositions described herein are provided in kit form. In one embodiment, the kit comprises a vial of glucagon, a vial of insulin, a means for administration, such as a syringe or pump, and instructions for the administration of the glucagon and insulin. In some embodiments, the glucagon and insulin are premixed in a single vial. In other embodiments, the insulin and glucagon are premixed in a syringe. The particular instructions will vary depending upon the desired use of the kit, e.g. for nocturnal control of hypoglycemia or otherwise. The instructions can be determined by one of skill in the art, given the present disclosure and the particular use intended for the kit. In one embodiment, the instructions will describe the methods disclosed herein.

Exemplary kits contain glucagon and one or more of the following packaged together: (1) insulin; (2) a solution (e.g., excipient) for resuspending or diluting glucagon (3) a device for administering glucagon and/or insulin; and (4) instructions. In one embodiment, the device (3) contains the glucagon and/or contains insulin.

A kit may comprise glucagon in a powder form within a sterile vial with a standard septum seal. In one embodiment, the vial contains a mixture of 1 mg of lyophilized glucagon, 49 mg lactose, and hydrochloric acid to adjust the pH (glucagon is soluble below pH 3 or above pH 9.5). The kit also has a pre-filled glycerine syringe, which contains 12 mg/ml of glycerine in a mixture of water, and hydrochloric acid. A second container holds a 1 mg/mL solution of insulin, which may be stored in liquid form in a syringe. The kit further has instructions, instructing the user to inject 1 mL of diluent from the pre-filled glycerine syringe into the vial. The instructions then direct the user to collect an amount of the glucagon/glycerine solution into the syringe containing the insulin. This amount will vary depending upon intended use and the particular user and may be determined by a physician.

In one embodiment, the volume of glucagon collected in the syringe is between 0-5% of the volume of insulin to be injected. The kit may comprise tables and/or charts allowing for ease of use and customization to determine what amount or ratios should be used for each user and situation.

The entire dose in the insulin syringe can then be injected (children are typically administered 50% of a standard dose, and the kit can be modified accordingly). In one embodiment, the insulin syringe and the glycerine syringe are one and the same, in which case the starting amount of glucagon is lower to maintain the appropriate ratio of glucagon to insulin that is injected. In another embodiment, the insulin, glucagon and glycerine are premixed in the kit. Instructions are adjusted accordingly for the particular embodiment used. In one embodiment, the kit comprises a glucagon kit, an insulin kit, and instructions for how to combine the two kits. As will be appreciated by one of skill in the art, any of the above discussed compositions or methods may be included in the kit as components or instructions. Thus, for example, various methods of administration, various compositions of insulin or glucagon, and various buffers or solvents may be used in the kits. In one embodiment, a means of administering insulin rapidly is combined with a means of administering glucagon more slowly. In one embodiment, the kit comprises only a form of glucagon with a set of instructions.

In one embodiment, the instructions can direct the user to administer more than 5 to 20. e.g. 6 to 16. ng/kg/min. of glucagon subcutaneously. In one embodiment, the instructions will direct the user to administer 30-45 ng/kg/hour of glucagon. In one embodiment, the units of glucagon are in 1500 ng and 2250 ng size doses for a 50 kg person, one dose to be taken each hour. In another embodiment, the units of glucagon are in 3000 to 4500 ng size doses, for a 100 kg person, one to be taken each hour. The kit can include a device for subcutaneous administration. In one embodiment, the units of glucagon are in a 36 microgram size dose for a 50 kg person, one dose to be taken each hour. In another embodiment, the units of glucagon are in 24 to 96 or 36 to 96 microgram size doses, for a 100 kg person, one to be taken each hour. These subcutaneous values can be sufficient to create hyperglycemia in some diabetic patients; thus, in some embodiments, less glucagon is required, e.g. an amount similar to that to be administered intravenously, 0.1-5 ng/kg/min. or higher. In some embodiments, the kits include instructions regarding doses for the age, weight, and sex of the individual. In one embodiment the instructions include information concerning doses to take in view of future activities, such as sleeping, eating (e.g., how much and what type of food), sitting, or exercising. As will be appreciated by one of skill in the art, an I.V. or s.c. dose equivalent can also be used if glucagon is to be administered in another manner. In some embodiments, the kits contain unit doses of glucagon to be added with the insulin. For example, a unit dose can be about 50 or 100 micrograms (or milliunits), which can be sufficient to protect a 100 kg subject for a one hour period from hypoglycemia. Unit doses can be prepared for 1, 2, 3, 4, 5, 6, 7, 8, 9, 10, 11, 12, 14, 16, 18, 20, 22, 24 or more hours or days. Smaller doses for smaller people or fractional hours are also contemplated.

Unit Doses of Glucagon

In one embodiment, rather than providing a mixture of glucagon and insulin, unit doses of glucagon alone are provided so as to be readily administrable to a subject as required, to prevent insulin-induced hypoglycemia. As the ratio of glucagon to insulin can be low, the amount of glucagon in the unit dose can also be low. As will be appreciated by one of skill in the art, the actual amount of glucagon in each dose will depend upon the characteristics of the individual, possible activities that the individual is going to do or has done, how the dose is to be administered and the form of the glucagon. Thus, the doses described below are only representative of some of the possible doses. The dosage can be determined by the skilled practitioner in view of the present disclosure.

A unit dosage form of glucagon contains a discrete quantity of glucagon for administration, and may be in the format of tablets, capsules, or powders in a container such as a vial or ampoule, cartridge, syringe, inhaler, transdermal patch, or other container or package. The quantity of glucagon in a single unit dose form preparation is typically from 0.002 mg to 0.1 mg. However, as will be appreciated by one of skill in the art, the amount in each dose can vary based on the manner that the material is to be administered. The previous units are for I.V. administration. For s.c. administration, the amount of glucagon in a unit dose can be, for example, from 0.002 mg to 0.2 mg or 0.036 mg to 0.4 mg for a 100 kg person, which dose should be effective for at least 1 hour. Preferably, the unit dose is between about 40 micrograms and 300 micrograms, and more preferably, between about 50 and 100 micrograms. Of course, these numbers can be adjusted based on the size of the average person to be treated and the duration of hypoglycemia prevention desired per unit dose. For example, with slow release formulations, it can be particularly advantageous to include sufficient glucagon for release over 2-3, 3-5, 5-8. or more hours. Thus, larger doses are possible, in certain circumstances. Lower amounts, even through s.c. administration, can also be used to ensure that hyperglycemia does not even transiently occur.

A single unit dosage form contains sufficient glucagon for a single administration of glucagon as described herein. Unit dosages can be designed for particular events. For example, they can be designed for use before or after the administration of insulin. Alternatively, they can be designed for administration in view of activities such as eating or exercising or going to sleep. As the amount of glucagon to be administered will depend upon various factors of a patient, such as lifestyle and weight, the unit dose can be expressed in universal units for ease of adjusting the dose. Additionally, how the unit is to be administered can also alter the amount of glucagon one places in each unit dose. These universal unit dosages are actually unit doses that are divided into smaller individual parts. Thus, a 50 kg individual can take 5 parts of these universal unit doses, while a 100 kg individual might take 10 parts. This allows greater customization of the glucagon intake. Of course, lower amounts of glucagon, e.g. similar to I.V. administration, can also be used if lower levels of elevated blood sugar are satisfactory. Thus, even for subcutaneous administration, a unit dose can be between 0.036 mg and 0.2 mg or 0.002 mg and 0.2 mg, for example.

In a related aspect, a pharmaceutical preparation of glucagon in daily unit dosage form is provided. The daily dosage form contains sufficient glucagon for one day, including the case in which glucagon is administered multiple times during a single day as described herein. For example, there may be multiple (e.g., 2 or 3 or more) glucagon administrations after a meal or meals during the day (see, e.g., Example 1 and/or administrations for prevention of nocturnal hypoglycemia; or continuous administration via, for example, transdermal patch or pump). In one embodiment, for example, via I.V. administration, 0.02 mg to 1 mg glucagon is provided in a container accompanied by instructions (e.g., a label) that the glucagon should be administered as separate doses over the course of a day. Usually the amount of glucagon is not more than about 0.04 U, and is often not more than about 0.02 U, not more than about 0.01 U, not more than about 0.005 U and sometimes not more than about 0.002 U. In one embodiment, the amount of glucagon given over one day is about 0.84 mg via I.V. or a dose equivalent for s.c. injection. For subcutaneous administration, 960 to 4800 micrograms of glucagon can be provided for administration over a day. In one embodiment, the glucagon is in a slow release form that is given all at once. In another embodiment it is in the form of, for example, 6 pills, one to be taken every four hours.

In a related aspect, a pharmaceutical preparation of glucagon in multiple dosage form is provided. A multiple dosage form of glucagon can contain a sufficient dose for administration for one, two, three, four, five, or six days, one week, or even more than one week. In one embodiment, for example, 0.02 to 0.036 mg to 1 mg of glucagon is provided in a container accompanied by instructions (e.g., a label) that the glucagon should be administered as separate doses over the course of a day or more than one day.

In one embodiment, a daily dose or multiple dose of glucagon is prepared by resuspending a powder in a liquid excipient, and a portion of the resulting solution can be administered at each administration during the day (or several days in the case of some multiple dose forms).

In addition to glucagon, the unit dosage form, daily dosage form or multiple dosage form can include other components, such as excipients, buffers, stabilizers, carriers and the like, as well as other pharmaceutically active agents. In one embodiment, as discussed above, the unit dose includes insulin or an insulin secretagogue.

Multiple doses of glucagon (e.g., multiple daily doses) can be packaged together in a box, bubble-wrap, or in other well known formats.

In general, the dosage forms will be labeled or will be accompanied by instructions for proper dosing. For example, the daily dosage form may be labeled to indicate the number and/or weight or volume of unit doses in the container. The dosage forms may also be labeled or otherwise indicate the age of the patient for whom the preparation is intended. For example, the dosage form may be indicated as suitable for adults, children over 15 years of age, children over 10 years of age, children over 5 years of age, and the like.

In one embodiment, any of the above glucagon dosages may comprise a extended release glucagon. In such embodiments, the dosage is appropriately adjusted, as disclosed herein, to maintain a blood glucose level within the desired ranges.

Glucagon Solutions

Administration of low doses of glucagon (e.g., less than 0.01 U) can be inconvenient using formulations prepared according to conventional methods (e.g., resulting in an approximately 1 mg/ml solution). Accordingly, in some embodiments, a lower concentration glucagon solution is made and/or administered. Administration, as used in this context, includes self-administration (whether by injection, by infusion using a pump, or other methods) and administration by another. In various embodiments, glucagon is administered as a solution having a concentration of less than about 0.25 mg/ml, for example, less than about 0.2 mg/ml, less than about 0.1 mg/ml, less than about 0.05 mg/ml, less than about 0.01 mg/ml, or even less than about 0.005 mg/ml of glucagon. In an embodiment, the concentration of glucagon is preferably at least about 0.001 mg/ml. In another embodiment, the concentration of glucagon is at least about 0.01 mg/ml. Such amounts can be appropriate for I.V. administration and dose equivalent amounts can be created for other methods of administration. For example, if the method of administration is s.c. injection, then the concentration of glucagon can be higher, at least about 0.01 mg/ml, or 0.05 mg/ml, or, 0.2 mg/ml, 0.5 mg/ml, or between about 0.5 mg/ml and 2 mg/ml of glucagon. In some embodiments, these doses are combined with a device that can administer the doses in low amounts over a prolonged period of time, such as a pump.

Glucagon can be resuspended in any pharmaceutically acceptable carrier, diluent or excipient.

In one embodiment, a pharmaceutically acceptable formulation of glucagon contains a concentration of less than about 0.25 mg/ml, less than about 0.2 mg/ml, less than about 0.1 mg/ml, less than about 0.05 mg/ml, less than about 0.01 mg/ml, or even less than about 0.005 mg/ml when it is to be administered I.V., or a dose equivalent amount for other methods of administration. For example, for compositions that are to be administered subcutaneously, a pharmaceutically acceptable formulation of glucagon contains between 0.5 and 2 mg/ml of glucagon.

In a related embodiment, a method of preparing a glucagon formulation for therapeutic use is provided and involves adding an aqueous solution to a composition comprising glucagon (such as, but not limited to, a single unit dose, daily dose or multiple doses of glucagon as described above) in a quantity that results in a solution containing glucagon at a concentration of less than about 0.25 mg/ml, less than about 0.2 mg/ml, less than about 0.1 mg/ml, less than about 0.05 mg/ml, less than about 0.1 mg/ml, or even less than about 0.05 mg/ml for I.V. administration. Concentrations 2 to 10 fold higher (or more) can be used for other methods of administration, such as subcutaneous administration. The solution can contain other agents, both pharmaceutically active and/or inactive.

In one embodiment, the glucagon solution is loaded into, or is contained in, a device for delivery to a patient. In some embodiments, the device contains at least about 0.1 ml, at least about 0.2 ml, at least about 0.3 ml, at least about 0.4 ml, at least about 0.5 ml or more than 0.5 ml of a glucagon solution.

In a related aspect, the further step of administration or self-administration to a human subject with diabetes is provided. In one embodiment, the subject does not exhibit symptoms of hypoglycemia. In one embodiment the human is an adult. In one embodiment the human is older than 10 years old, and optionally older than 15 years old or older. In one embodiment, the subject is not suffering from a stomach ailment.

In one embodiment, any of the above glucagon solutions may comprise an extended release glucagon. In such embodiments, the dosage is appropriately adjusted, as disclosed herein, to maintain a blood glucose level within the desired ranges described herein.

The methods and compositions disclosed herein may be used to treat human patients as well as other mammals (e.g. rats, mice, pigs, non-human primates, and others). In some embodiments the human patient is a child or juvenile; in one embodiment the human patient is an adult. In some embodiments the patient is a Type I diabetic. In one embodiment the patient is a Type II diabetic. In one embodiment the patient is a brittle Type I or Type II diabetic. In one embodiment, the non-human mammal is an animal model for the study of diabetes, e.g. Zucker diabetic-fatty (ZDF) rats, and db/db mice.

While many of the examples and much of the description provided herein is explicitly directed to subcutaneous administration of low doses of glucagon, other aspects are also disclosed. For example, while the subcutaneous doses described herein are generally greater than 5 and less than 20 ng/kg/min., other doses are also contemplated for the various embodiments described herein. For example, doses from 0.1 to 5 ng/kg/min. for I.V. or s.c. administration, especially in combination with long acting forms of glucagon (such as zinc protamine), various kits, and unit doses are contemplated along with the more than 5 to 20 or 30 ng/kg/min. doses. Additionally, as pointed out below, doses at 4 ng/kg/min., and lower, of s.c. glucagon can also be effective in preventing or delaying hypoglycemia. Thus, in some embodiments, the dose administered subcutaneously to prevent or delay hypoglycemia is about 0.1-5, 1, 1-2, 2-3, 3-4, 4-5. more than 5, 5-6, 6-8, 8-12, 12-16, 16-20. or 20-30 ng/kg/min. Corresponding amounts for unit doses, other doses for administration, or kits are also contemplated. For example, a 1 hour unit doses of glucagon for a 100 kg person at 4 ng/kg/min. would contain 24 micrograms of glucagon, and a 1 hour pharmaceutical composition would contain 24 micrograms of glucagon and 1-3 units of insulin. As will be appreciated by one of skill in the art, any of the disclosed doses can be turned into one hour unit doses or other aspects described herein given the present disclosure. This can depend upon dose amount (e.g., 0.1 to 30 ng/kg/min. or 6 to 16 ng/kg/min.), presence and amount of insulin (e.g. 0 or 2-20 Units), the size of the patient (e.g. 3-200 kg), and the number of hours of desired effectiveness (e.g., 0.5-24 or more).

The following examples describe illustrative embodiments of the invention and are not intended to be limiting in any manner.

EXAMPLE 1

Co-Administration of Glucagon Parenterally and Insulin for the Control of Diabetes and Prevention of Hypoglycemia The glucagon currently available in the North American market is human glucagon of rDNA origin produced either by Eli Lilly & Co or Bedford Labs (Novo). Four brand names are known: Glucagon Diagnostic Kit (Lilly); Glucagon Emergency Kit (Lilly); Glucagon Emergency Kit for Low Blood Sugar (Lilly); and GLUCAGEN (Bedford Labs).

Novo produces glucagon under its own name outside of North America. Novo produces its glucagon in yeast, and Lilly produces its glucagon in *E. coli*. The following examples illustrate practice of some of the methods using such commercially available glucagons and insulins administered via a variety of routes.

The Lilly glucagon is typically provided in kit form. The glucagon within the kit is in the form of a powder within a sterile vial with a standard rubber-sealed neck. The vial contains a mixture of 1 mg of lyophilized glucagon, 49 mg lactose, and hydrochloric acid to adjust the pH (glucagon is soluble below pH 3 or above pH 9.5). The patient injects 1 ml of diluent from a pre-filled syringe (which contains 12 mg/ml of glycerine in a mixture of water, and hydrochloric acid) into the vial. The vial is shaken until the solution is clear. The liquid is returned to the syringe, and the entire dose is injected (children are typically administered 50% of the standard dose).

Glucagon is administered parenterally by subcutaneous, intramuscular, and intravenous routes, with the pharmacokinetic properties differing accordingly as understood by those of skill in the art. Maximum plasma concentration is achieved approximately 20 minutes after subcutaneous administration. The half life in vivo ranges from 8 to 18 minutes. Peak plasma concentration of approximately 8 ng/ml are achieved after approximately 20 minutes, and elevated glucose levels persist for approximately 1½ hours after administration and begin rising almost immediately following administration. Patients with insulin-induced coma will typically recover consciousness within 15 minutes of glucagon administration. Parenteral glucagon, when given to treat hypoglycemia, does so primarily by increasing serum glucose availability through increased output of glucose by the liver (the conversion of glycogen to glucose and formation of new glucose by gluconeogenesis).

There are a wide variety of insulin dosage regimes in use. The regime used depends on whether Type 1 or Type 2 diabetes is being treated and on a large number of factors specific to the individual being treated. It is normal medical practice to replace insulin using a combination of parenterally administered insulins (usually subcutaneously) of rapid onset/short acting duration (LISPRO (HUMALOG) or ASPART (NOVOLOG)), slower onset/short acting duration (regular human insulin), intermediate duration (NPH or LENTE), long acting duration (ULTRALENTE), BASULIN (Bristol Myers Squibb) and 24 hour peak-less duration (GLARGINE (LANTUS) and DETEMIR).

The dosage regimes can be quite complex. For example, a typical twice-daily regimen might involve administering short acting and intermediate duration insulin before breakfast and supper. The insulin profile thus obtained has a number of peaks, which roughly correspond to the anticipated post-prandial glucose output, as well as providing a basal insulin level throughout any 24 hour period. This is illustrated in FIG. 1, which shows the idealized pharmacokinetics for a mixture of regular and intermediate acting insulin. The graph shows the effect of a twice-daily insulin regimen: Twice-daily administration of regular (solid lines) and intermediate-acting LENTE or NPH (dashed lines) insulins before breakfast and the evening meal provides peaks of insulin after the injections as well as a relatively constant baseline level of insulin throughout the day after injections of the intermediate-acting insulins.

Insulin levels can vary significantly between individuals and even within the same individual, depending on factors such as site and depth of injection, local blood flow, total volume and type of insulin injection, and other factors appreciated by those of skill in the art. Thus, there can be significant inter and intra-patient variability in subcutaneous absorption of insulin, which increases the likelihood of variations in serum glucose, including the possibility of hypoglycemia.

With the advent of the rapid onset insulins and a long acting insulin with little or no peak appearance GLARGINE (LANTUS); also, DETEMIR is a long acting insulin in development; in addition, ULTRALENTE is a long acting insulin but tends to have some peak effect in most patients), it became possible to manage insulin levels (and hence blood glucose levels) with more accuracy. The basic methodology is to replace basal insulin and prandial insulin through the combined use of insulin preparations having different rates of onset and durations of action. This may involve the use of separately administered insulins of differing onset, (e.g. GLARGINE and LISPRO) or the use of various pre-mixed formulations (e.g. 70/30-70% NPH and 30% regular combined), which are commercially available for this purpose.

The point at which the glucagon is administered is before, during, or immediately prior to the period when insulin action is most unopposed, for example when significant insulin action persists in the absence of sufficient serum glucose availability. Thus, insulin-induced hypoglycemia may occur whenever there is a mismatch between circulating insulin and glucose levels (a relative excess of insulin effect to glucose availability).

Insulin Administered Parenterally (i) GLARGINE/LISPRO/ASPART/GLULISINE Insulins

For this illustrative example, the patient (all patients referred to herein are fictitious, except for any reference to patients in the examples describing actual clinical testing; any resemblance to an actual person is coincidental) is an adult male, 50 years of age, weighing 75 kg, with 5 L of blood, suffering from type-2 diabetes and using insulin therapy (without concomitant oral combination therapy). He has been using insulin for over 10 years and his glucagon response to hypoglycemia is minimal. His insulin regimen involves basal insulin replacement using GLARGINE (LANTUS) subcutaneous injections at a dosage level of 20 units administered at bedtime in addition to prandial insulin injections of LISPRO (HUMALOG), ASPART (NOVOLOG), GLULISINE (APIDRA) of between 5 and 10 units (depending on the amount of carbohydrate consumed) administered at mealtimes.

Figure 2:
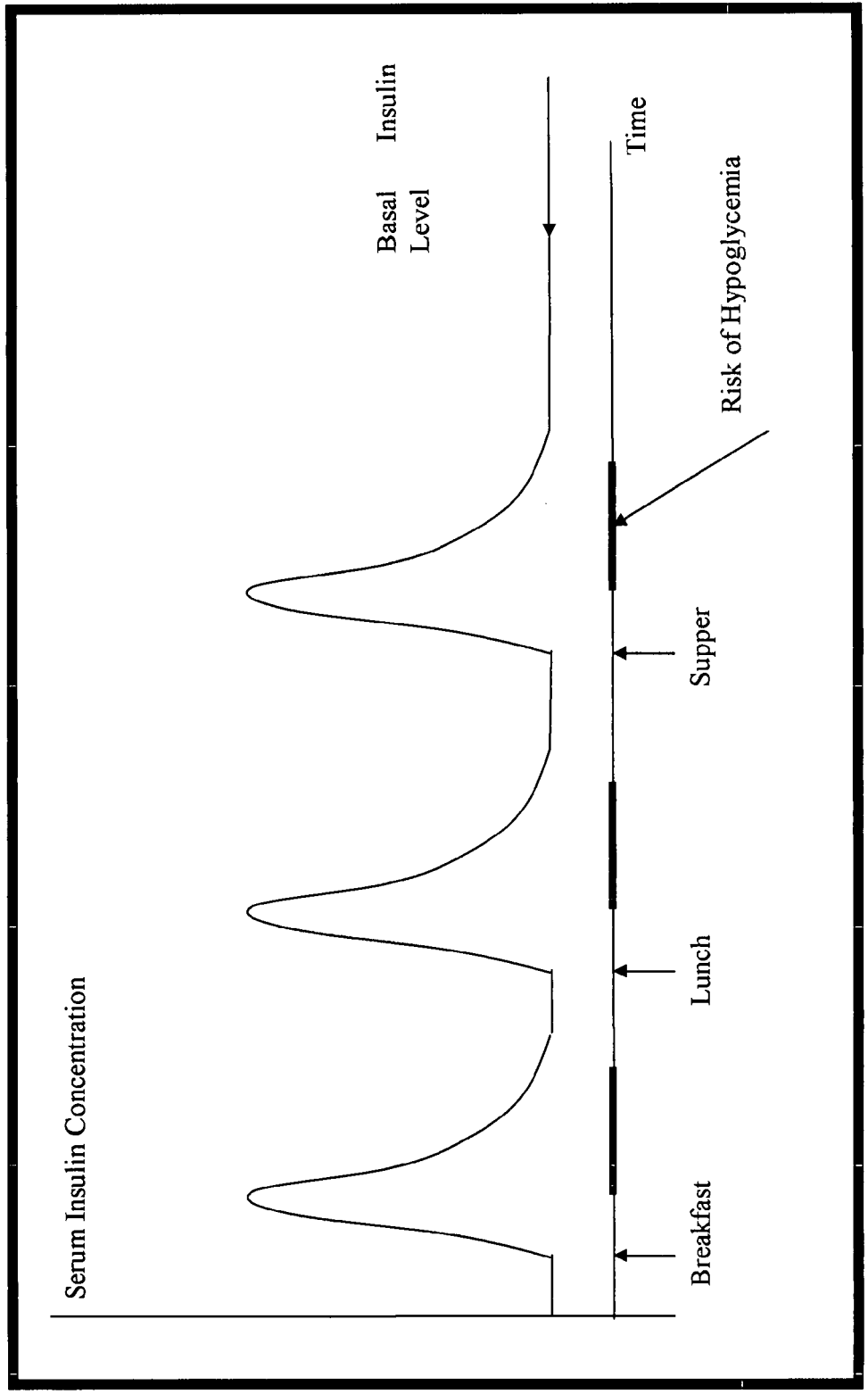
FIG. 2 is a graph illustrating the insulin profile of a hypothetical patient, as described in Example 1. Part A(i), showing a very simple, flat line graph (basal level set by the GLARGINE (LANTUS)) punctuated by peaks corresponding to prandial LISPRO (HUMALOG) insulin injections.

His insulin profile is very simple, being a flat line (basal level set by the GLARGINE (LANTUS)) punctuated by peaks corresponding to the prandial LISPRO (HUMALOG), ASPART (NOVOLOG), GLULISINE (APIDRA) insulin injections. This insulin profile is shown in FIG. 2. In this patient, the risk of hypoglycemia typically arises between 2 and 5 hours after the meal. It is during this period that administering glucagon is most efficacious and effective in preventing the possibility of a hypoglycemic episode. In non-diabetics, glucagon usually falls following a carbohydrate meal (in response to increased glucose levels) and then recovers subsequently as glucose levels return to normal. In type-1 diabetics (and type-2 diabetics of 5 years or more) the glucagon response to low serum glucose is limited. Hence, if insulin causes the serum glucose level to drop well below the basal level, hypoglycemia will ensue.

Hypoglycemic symptoms are typically observed in diabetics at glucose levels less than 50 mg/dl, or sometimes less than 40 mg/dl. In normal individuals, glucagon release would be augmented (by about 40 pg/ml or higher, e.g. augmented by about 60 pg/ml or higher) before glucose levels fell this low and would prevent the onset of hypoglycemic symptoms. However, glucagon production (or regulation) is deficient in many insulin-treated diabetics. Thus, administering glucagon to achieve these levels during the period of susceptibility will prevent or attenuate the severity of hypoglycemic attack.

The s.c. dose of glucagon required to provide prophylaxis is in some embodiments about 6-20 ng/kg/min. for basal insulin levels, and a proportionally higher amount for higher levels of insulin.

Thus, in accordance with the methods, this patient is administered 41 to 90 micrograms of glucagon subcutaneously after the meal. Two similar doses are administered hourly for an additional two hours. This makes three doses at hours 2, 3. and 4. providing protection from hypoglycemia for 3 hours beginning 2 hours after the meal. With formulations comprising both insulin and glucagon, one can use a lower percentage of glucagon (5.6%), as the risk and degree of hypoglycemia is (in part) insulin-dose-dependent. In this example, while the glucagon concentration from the dose administered 2 hours after the meal will have fallen back to approximately basal levels after an hour, the elevation of blood glucose due to this dose will persist for more than one hour, giving time for the second dose to take effect. The same pharmacokinetics applies to the third dose of glucagon. In an alternative embodiment, two doses or even one dose of glucagon can be administered.

Although this example employs a simple basal and prandial insulin model, it will be understood by those skilled in the art to be applicable to all currently practiced dosage regimens. The timing (and frequency) of the glucagon injections may be adjusted to match the period in which the patient is most susceptible to hypoglycemia, i.e. the point at which insulin action and glucose availability are most mismatched.

(ii) NPH/Human Insulins

A typical diabetic patient is an adult male, 63 years of age, weighing 75 kg, suffering from Type 2 diabetes for 18 years and using combination insulin therapy (without concomitant oral anti-diabetic therapy). In the past, he will typically have used oral anti-diabetic medications, including Glyburide and Glipizide, but these will have been stopped and insulin started when his serum glucose levels were consistently above 250 mg/dl. He will have been using insulin of one type or another for over 10 years and will have developed evidence of background retinopathy, mild renal impairment with a serum creatinine of 1.9 mg/dl and creatinine clearance of 60 ml/min, mild proteinuria, bilateral distal symmetrical neuropathy in both feet, and exertional angina. His insulin regimen would typically involve a split-mixed regimen of subcutaneous NPH insulin, 20 units before breakfast and 15 units before dinner, which is intended to provide day-long basal insulin coverage plus modest postprandial coverage for lunch and the evening meal (and bedtime snack). In addition, he injects regular insulin of between 6 and 10 units (depending on the level of pre-meal serum glucose as well as the size and carbohydrate content of the meal) before these meals.

His insulin profile is similar to that shown in FIG. 1, with less rapid peaks and slower decays resulting from the prandial injections of regular insulin and slower onset and delayed decay effects from the twice daily intermediate acting NPH insulin. His fasting glucose levels are typically well controlled in the range of 90-130 mg/dl, but his 1-2 hour postprandial glucose levels are suboptimal and generally range from 180 to 240 mg/dl. Glycosylated hemoglobin is elevated at 7.9% (normal range 4-6%). Efforts to increase his breakfast or evening meal dose of prandial regular insulin to reduce postprandial glucose levels is usually accompanied by frequent intermittent hypoglycemia, of mild to moderate severity, often 1-2 hours before lunch or several hours after dinner. These episodes of hypoglycemia can be quite severe and associated with symptoms of sweating, tremors, nausea, and headaches, particularly when he is late for meals. He has never had insulin-induced hypoglycemic coma but is reluctant to increase his insulin dosage in case this happens. He fears that he could lose his driver's license if this occurs or perhaps his job as a night watchman. Because of this patient's long history of diabetes and presence of significant complications, it is expected that he will exhibit impaired glucose counter-regulation to hypoglycemia, especially manifest as a blunted or absent glucagon response.

In this patient, the risk of hypoglycemia is usually greatest between 3 and 5 hours after a meal (late postprandial hypoglycemia), when circulating insulin levels are still increased above fasting level but glucose availability (from gastrointestinal absorption and liver production) is minimal. It is during this period, prior to the onset of hypoglycemia, that the administration of glucagon would be most efficacious and effective in preventing the possibility of hypoglycemic episodes by increasing circulating glucose availability. In non-diabetic individuals, both insulin and glucagon are tightly regulated following a meal to balance glucose production and utilization so as to maintain normoglycemia. Should insulin effects become pronounced, glucagon levels will rise to offset this hypoglycemic potential.

To prevent the development of hypoglycemia in accordance with one embodiment of a method, this patient is administered 36-96 milliunits of glucagon, administered subcutaneously (optionally using Eli Lilly's Glucagon Emergency Kit, as described above) two to three hours after each meal. In one embodiment, the glucagon is added when glucose measurements indicate glucose levels are approaching hypoglycemic levels. This administration provides the required protection between hours 3 and 5. as described above.

Although this illustrative example employs a simple basal and prandial insulin model, it will be understood by those skilled in the art to be applicable to virtually all currently practiced insulin dosage regimens. The glucagon injections are optimally timed and vary depending on the insulin regimen used but are designed to achieve sustained glucagon levels during the expected periods of relatively unopposed insulin action.

In the current hypothetical example, this situation tends to occur at several times throughout the day. For example, hypoglycemia is prone to occur when the "tail" of injected regular insulin absorption combines with peaking insulin availability from the intermediate acting NPH. This situation occurs several hours after breakfast when serum glucose availability (primarily from gut absorption and liver production) is minimal or decreasing. Similar situations also often occur before dinner, at bedtime, and in the middle of the night. Thus, for all insulin dosage regimens, the timing of glucagon injection can vary depending upon the pharmacologic characteristics and timing of the insulin(s) used.

To offset the glucose-raising potential of the administered glucagon, the dose of insulin acting during that hypoglycemic period can be increased somewhat to maintain euglycemia. However, the increased availability of glucagon provides a buffering action or cushion to the excessive glucose lowering action of insulin in those specific circumstances as described above and blunts or prevents hypoglycemia.

B. Insulin Administered by Pump

In this example, the patient described in Example 1.A.i uses a pump to administer his insulin requirement. Instead of administering basal insulin by GLARGINE (LANTUS) once daily as in Example 1.A.i, the patient's insulin pump is programmed to provide a continuous stream of rapid-onset insulin (e.g. LISPRO or ASPART). In this example, he administers ASPART in doses of between 5 and 10 units at mealtimes according to the pre-meal glucose level and the amount of carbohydrate and calories consumed. The patient will then, in accordance with this method, administer glucagon (using Bedford Lab's GLUCAGEN product, for example) two hours after the meal and repeat the dose hourly for another two hours. This amount can be about 36 to 96 micrograms of glucagon, delivered s.c. The glucagon is administered subcutaneously. This administration provides protection from hypoglycemia between hours 2 and 5. as described in Example 1.A.i. As will be appreciated by one of skill in the art, the glucagon can also be administered via a pump. In an alternative example, the amount of glucagon is scaled up per unit of insulin; thus, 36-96 micrograms are used per unit of insulin.

C. Insulin Administered Transdermally [Including Patch and Topical Cream]

In this example, the patient is a 62 year old, lean Type 2 diabetic of 6 years duration. He was initially treated with Glyburide 20 mg twice daily and subsequently with the addition of Metformin 1 gram twice daily, but fasting and postprandial blood glucoses were consistently in the range of 200-350 mg/dl. He is advised by his physician that insulin is required. The oral anti-diabetic medications are discontinued and GLARGINE (LANTUS) insulin 15 units is administered at bedtime to provide his day-long basal insulin replacement needs. Postprandial insulin is administered by transdermal patch to provide 2-6 units of rapidly acting insulin (patches available in 2 unit increments; although this example refers to use of a patch, those of skill in the art will appreciate that substantially similar methodology can be employed to practice the embodiment with insulin or glucagon delivered transdermally by other means, such as creams or lotions). Alternately, he is offered the 24-hour basal insulin replacement patch instead of once daily GLARGINE. The basal insulin replacement patch contains insulin in a unique formulation designed to provide steady continuous absorption and low constant serum insulin levels throughout the day. Because of persistent elevation of fasting plasma glucose, his physician progressively increases his dose of GLARGINE insulin over 6 months to 24 units and transdermal patches to 4-10 units. With this increase in GLARGINE and transdermal insulin dosage, fasting glucose levels ranged from 70-110 mg/dl and 1-2 hour postprandial glucose levels from 130-180 mg/dl within 3 months.

The patient applies the rapidly-acting insulin patches 30-60 minutes prior to meals. This timing is chosen so that absorption of the meal coincides with insulin patch absorption kinetics and action. This patient has near normal glycemic control as indicated above but begins to suffer from early morning hypoglycemia, typically at 1 or 2 a.m. At these times, this hypothetical patient is frequently confused, irritable, and at times anxious. Several readings of finger-stick glucose taken during these events reveal blood glucose values of 35-40 mg/dl with prompt resolution of symptoms with ingestion of juice. In an effort to control these bouts of hyperglycemia, his physician gradually decreases the evening dose of GLARGINE, but this is associated with deterioration in glycemic control and, primarily, elevation of pre-prandial glucose levels.

To restore near-normal glycemia but prevent early morning hypoglycemic symptoms in accordance with some embodiments of the methods, the physician increases the GLARGINE insulin back to 24 units at bedtime and prescribes administration of subcutaneous glucagon at 18 ng/kg/min. of intended protection (using Bedford Labs Glucagon product) immediately following the injection of GLARGINE at 23:00. The time of administration of glucagon depends primarily on the rate of absorption, which is rapid, reaching peak levels within 15-30 minutes, and a duration of action of approximately 2-3 hours. In one embodiment, plasma glucagon approximating "high normal basal levels" is maintained during this period and prevents an unopposed action of insulin from GLARGINE insulin or a delayed action of the early evening (pre-dinner) patch. For example, glucose levels of more than 120-160 mg/dl are contemplated. In an alternative embodiment, the low end of the normal glycemic levels are set as a goal for the blood glucose level. This therapy provides the required protection from hypoglycemia for approximately 3 hours after the GLARGINE injection, as described above. With the addition of bedtime glucagon to his diabetes regimen, the early morning hypoglycemic episodes should resolve and day-long near-normal glycemia be preserved. As will be appreciated by one of skill in the art, a s.c. or i.v. dose equivalent of glucagon can also be administered in the same manner as the insulin (e.g., transdermally via patch or cream).

D. Insulin by Inhalation [Including Pulmonary, Buccal Nasal and Sublingual]

This example is similar to Example 1.A.i, except the patient administers insulin by inhalation rather than by subcutaneous injection. It will be understood by those skilled in the art that similar methods apply when insulin is administered buccally, nasally, or sublingually in accordance with these methods, although a dose equivalent amount will be applied. The patient will either continue to administer his basal need via GLARGINE (LANTUS) or he will utilize an insulin inhaler to administer basal insulin needs. The patient will administer his prandial insulin need (equivalent to between 5 and 10 units administered by subcutaneous administration) using his insulin inhaler (either pulmonary, nasally, buccally, or sublingually).

In accordance with these methods, the patient will then subcutaneously administer 45 micrograms of glucagon (optionally using Lilly's Glucagon kit) two hours after the meal and another two doses hourly thereafter. He will administer the glucagon subcutaneously. This will provide the required protection from hypoglycemia between hours 2 and 5. as described in Example 1.A.i. As will be appreciated by one of skill in the art, the glucagon can also be administered via inhalation, in a dose equivalent amount. Alternatively, a lesser amount of glucagon is administered, for example, 3-5 micrograms of glucagon for 0.5 to 2.0 units of insulin. As will be appreciated by one of skill in the art, the precise amount of glucagon administered can vary and can be determined for various amounts of insulin, via the method shown in Example 8 below.

EXAMPLE 2

Co-Administration of Glucagon by Pump and Insulin for the Control of Diabetes and Prevention of Hypoglycemia In one method, insulin can be administered by pump. There are a number of pumps commercially available (or soon to be available) in the US market and elsewhere that are suitable for use in the present methods. These include but are not limited to:
ANIMAS (IR-1000 & IR-1200)
DELTEC (Cozmo pump)
DISETRONIC (H-TRONplus and D-TRONplus)
LIFESCAN & DEBIOTECH (MEMS Insulin Pump in development)
MEDTRONIC MINIMED (PARADIGM Insulin Pump and 508 Insulin Pump)
MEDTRONIC MINIMED (2007 Implantable Insulin Pump System (EU only))

When both the insulin and the glucagon are to be administered by pump (from separate reservoirs), a number of configurations can be employed in the practice of the present method. Typical configurations are:
(1) A single device with a single pump and two reservoirs (for dual reservoir pumps, see, for example, U.S. Pat. No. 5,474,552) with each drug delivered through 2 separate lines that are merged prior to cannulization;
(2) A single device with a single pump and two reservoirs with each drug delivered through 2 separate lines, each of which is independently cannulized;
(3) A single device with two independent pumps and two reservoirs with each drug delivered through 2 lines that are merged prior to cannulization;
(4) A single device with two independent pumps and two reservoirs with each drug delivered through 2 separate lines, each of which is independently cannulized;
(5) Two devices, each with a single pump and one reservoir, with each drug delivered through 2 separate lines that are merged prior to cannulization; and
(6) Two devices, each with a single pump and one reservoir, with each drug delivered through 2 separate lines independently cannulized.

It will be understood by those skilled in the art that other configurations are possible and that the practice of the embodiments are not limited to the devices and device configurations listed above. For example, implantable pumps may be used in almost exactly the same way as is achieved using external pumps.

Embodiment (1) above minimizes trauma to the patient on cannulization, reduces cost, simplifies infusions, and minimizes complexity. With this embodiment, the single pump can be programmed to deliver appropriate volumes from each reservoir, each containing different concentrations of one of the two hormones. An example of such a pump is provided herein.

In a typical insulin pump, the internal pump mechanism usually comprises an electromagnetically driven pulsatile pump having a solenoid operated piston mounted for reciprocation within a cylinder to draw medication from an internal storage chamber (reservoir), and to deliver such medication through the delivery line and then via a cannula or microcannula to the patient.

Because delivery lines used with pump insulin are typically one-half to one meter in length with lumen diameters of the order of $\frac{1}{10}$th of a millimeter (dead volume of the order of a $\frac{1}{10}$th of a milliliter or about 10 IU of Insulin), the time delay between a new drug reaching the body and the time at which the pump starts infusing it is likely to be substantial (about half a day).

To reduce this delay, one embodiment provides pumps with lines of much shorter length and/or of very small internal lumen diameter that enable the lag time between a switch in drugs to be much shorter. The present embodiment also provides peristaltic type pumps acting on two delivery lines.

One embodiment provides a system comprising a pump and a set of four valves, two immediately before and two immediately after the pump, which when operated in pairs, control which drug is pumped. The two lines are, in one embodiment, merged at the point of cannulization, thereby eliminating the lag or (dead volume) time. The extra space required for the electronically actuated micro-valves is minimal and adds little bulk or expense and can be assembled using commercially available devices. Additional possibilities involving the use of fewer than 4 valves are described below.

In one embodiment, an economical pump system suitable for use in some of the methods is a micro-pump known as MEMS (Micro-Electro-Mechanical System), being developed for diabetes by Debiotech under the brand name Chronojet. The use of two such micro-pumps in a unitary device adds little bulk and only minimal expense to existing designs. As noted above, the two delivery lines can be merged (in the sense that the two drugs come into direct contact) at the point at which they connect to the cannula or similar micro-needle device used to puncture the skin and deliver the drug.

In one embodiment, a single split-lumen (dual lumen) line is used instead of two physically separate lines. This method has the advantage that the patient has only to route one flexible delivery line rather than two. Alternatively, two standard lines physically adhered along their lengths can be used in accordance with some embodiments of the methods to achieve the same advantage.

Figure 3:
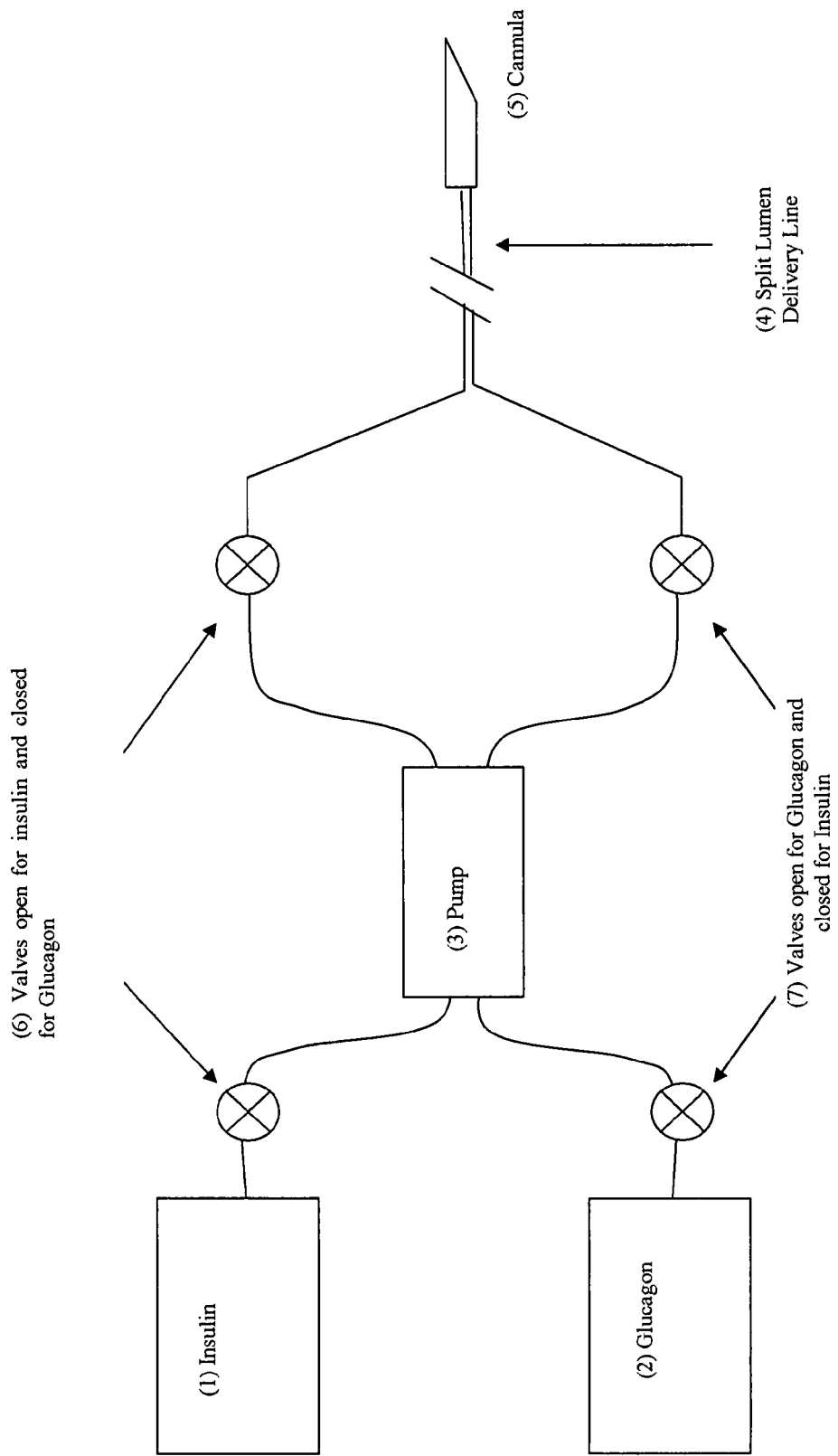
FIG. 3 is a schematic of a drug delivery pump configured for practice of an embodiment described in Example 2.
Figure 4:
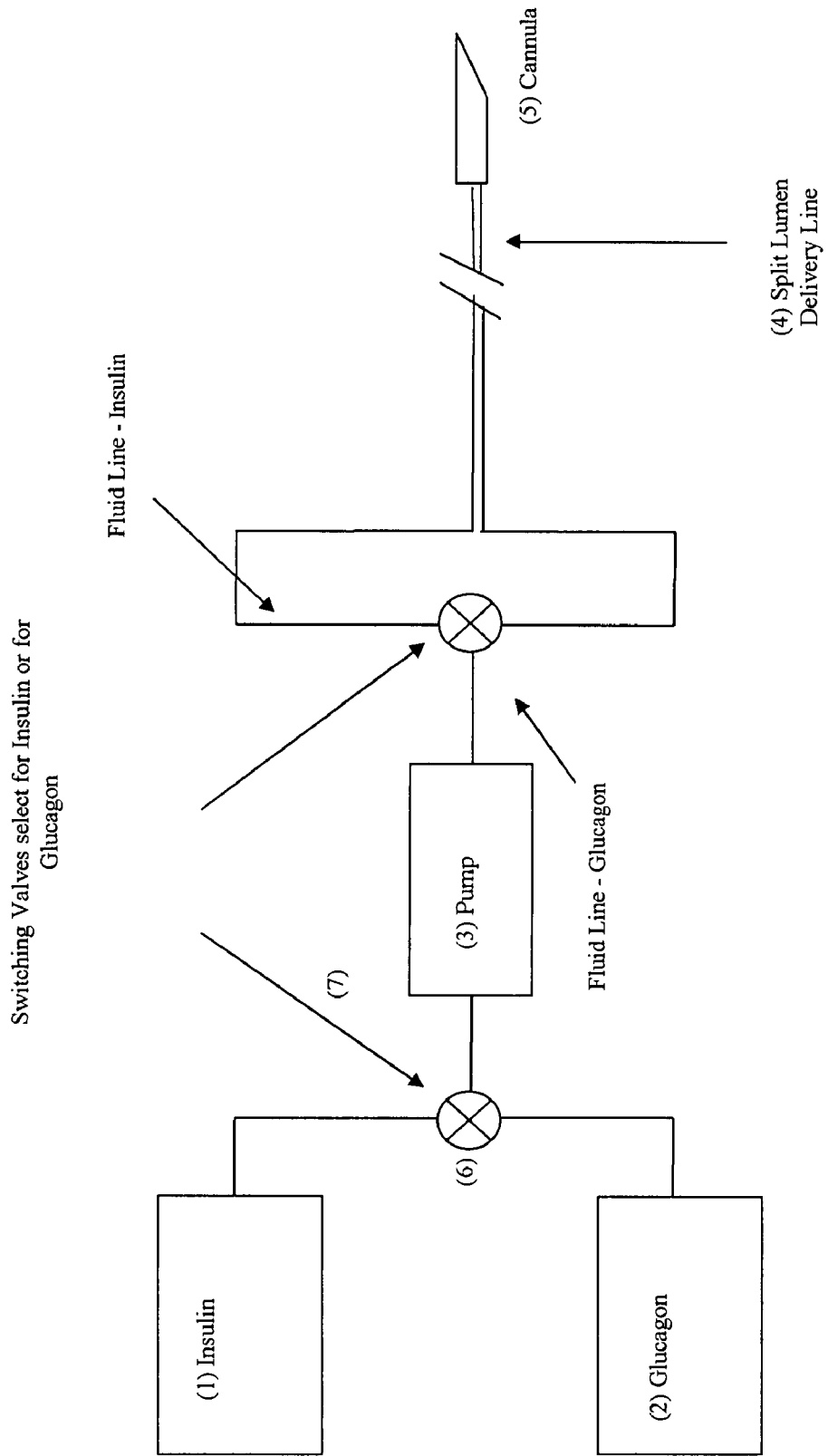
FIG. 4 is a schematic of a drug delivery pump configured for practice of an embodiment described in Example 2.
Figure 5:
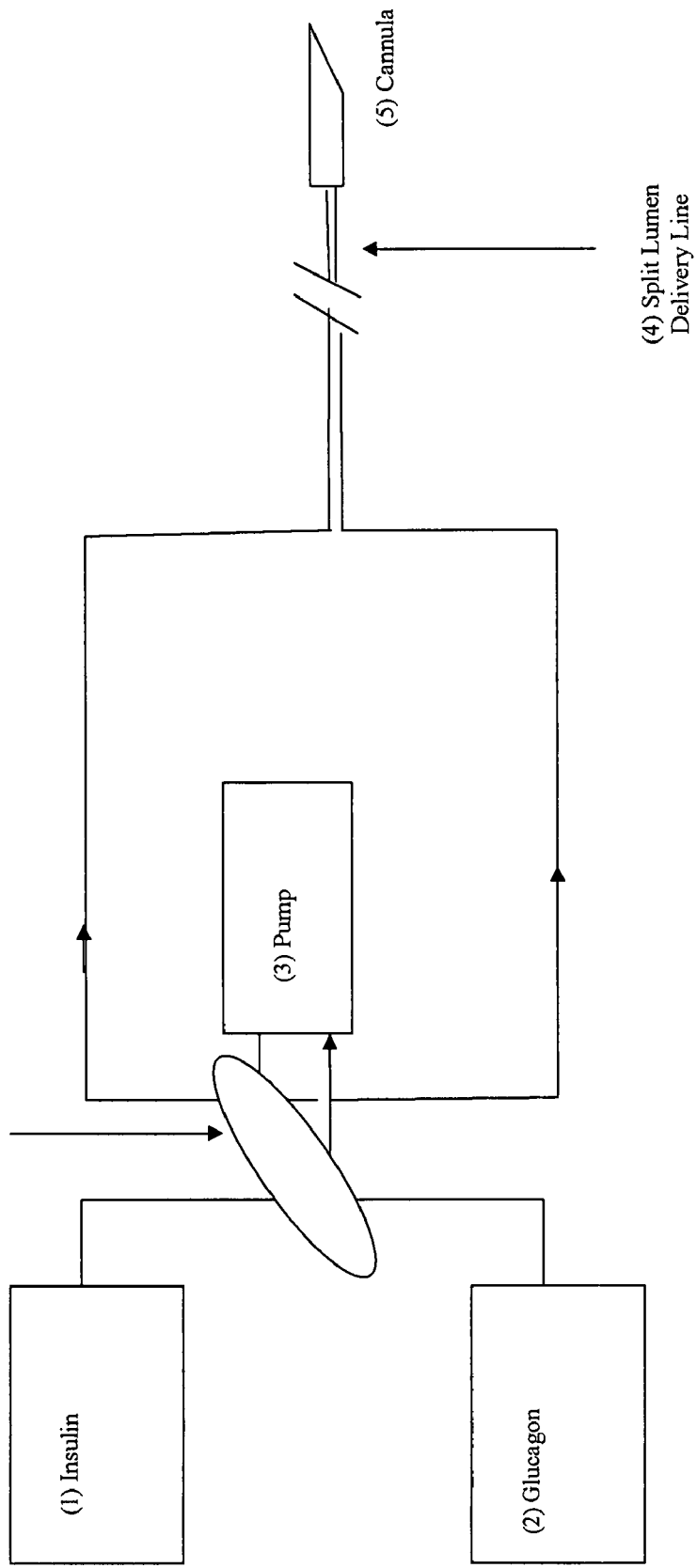
FIG. 5 is a schematic of a drug delivery pump configured for practice of an embodiment described in Example 2.

In one embodiment, therefore, the pump is a currently used insulin pump modified to have two drug reservoirs instead of one, each being independently administered by a single (or dual) pump and a single control system to manage the quantity and relative timing of administration of the two drugs. As noted above, the device can in some embodiments comprise 1, 2 or 4 valves and appropriate connective tubing. Schematics of devices that can be used in accordance with some of the methods are shown in FIGS. 3, 4, and 5. In FIG. 3, the insulin reservoir (1) and the glucagon reservoir (2) have lines in fluid communication with pump (3) and then on to the cannula (5) via split lumen delivery line (4) by way of 4 valves (6) and (7). When valves (6) are open and valves (7) are closed, only insulin is pumped. When valves (6) are closed and valves (7) are open, only glucagon is pumped. In this way, a single pump may be used to deliver insulin or glucagon to the patient, either simultaneously or separately, with minimal mixing of the two substances by virtue of delivery through a split lumen delivery line in which the liquids only mix at the cannula, i.e. the point of deliver. In FIG. 4, the insulin reservoir (1) and the glucagon reservoir (2) have lines in fluid communication with pump (3) and then on to the cannula (5) via split lumen delivery line (4) by way of 2 valves (6) and (7). These are 2-way valves that allow either the insulin path or the glucagon path to be open—but only one at a time. A small amount of mixing of the two fluids will take place in the small stretch of line through the pump, but this will be an insignificant volume when compared to typical pumping volumes. In this way, glucagon and insulin may be delivered to the patient with minimal mixing and dead space in the lines. The advantage of this construction over the construction described disclosed by FIG. 3 is that only two valves are required for operation. In FIG. 5, the configuration here is the same as that disclosed in FIG. 4, but in this case the two valves (6) and (7) are combined into a single device with a unitary actuation mechanism. In this way the mechanism is kept as cheap and simple as possible, with only one valve and one pump required to achieve the desired result.

It is normal practice with pumped insulin for the patient to set the pump to deliver a basal level of insulin and to intervene manually to administer prandial insulin as required.

In one embodiment, the glucagon delivery is automatically administered over the appropriate period (for example continuously between the 3rd and 5th hours following the manual instruction to deliver the prandial insulin). The control logic required to produce such a sequence of events can be programmed into the pump.

A. Insulin Administered by Pump

This example illustrates how some of the methods can be practiced using pump-based administration. A typical hypothetical patient is an adult male, 35 years of age, weighing 75 kg, having type-1 diabetes since the age of 15 and using insulin therapy from the time of diagnosis. He has been on a number of different insulin regimens previously with less than optimal glycemic control. In the last 5 years, he has begun to develop significant background retinopathy, mild renal insufficiency, and hypertension, and is concerned that these complications will continue to progress rapidly unless he is able to improve glycemic control from his current glycosylated hemoglobin level of 7.8%. Most recently, he has been on ULTRALENTE, 22 units, at bedtime and LISPRO insulin, 4-8 units, just prior to each meal and snack. The dose of ULTRALENTE has been adjusted to provide basal replacement of insulin, while the dose of prandial LISPRO varies depending upon the prevailing pre-injection serum glucose and total calories and carbohydrate content of each meal.

Despite self-monitoring of capillary blood glucose by glucometer 4-6 times per day, his glycemic control is often erratic, ranging from high values in the 200 mg/dl range to occasional hypoglycemia. In the previous year, he has had 3 bouts of severe hypoglycemia with coma or near coma, two occurring while at work and the other following a game of handball. All required the assistance of others and in the post-exercise case required the intramuscular injection of glucagon by paramedics.

With using insulin pump therapy, short acting insulin is typically used, because the pump provides a continuous feed to simulate basal insulin over the long term. In this example, the patient uses ASPART (NOVOLOG) as his insulin of choice. The pump, reservoir, and control mechanism (in this illustrative case, the MEDTRONIC MINIMED PARADIGM INSULIN PUMP) can be attached at various sites about the body of the patient (most commonly on the belt, for example), and is linked by a flexible plastic tube to the micro-cannula he has inserted in his abdomen, thigh, or arm (women tend to place the infusion site in the lower abdomen while men usually choose the upper abdomen).

The patient has programmed the device to deliver 1 IU of insulin every 50 minutes (20 units a day). When the patient eats during the day, he programs the device to release an amount of insulin (between 3 and 8 units) appropriate to his meal situation (pre-meal glucose, total calories, and carbohydrate content). He does this by pushing the appropriate buttons on the device (or by use of a remote control device, if available) to select the size of the insulin bolus required.

Following use of the programmable insulin infusion pump, the patient has been able to achieve a marked improvement of glycemic control, with pre-prandial glucose levels ranging from 70-110 mg/dl, postprandial (1-2 hour) levels of 120-160 mg/dl, and glycosylated hemoglobin of 6.4%. However, he continues to be plagued by frequent mild-to-moderate hypoglycemic episodes that he frequently doesn't recognize until he measures his fingerstick glucose. Many of these low glucose values are in the range of 30-40 mg/dl. He has been told by his wife and friends that at times he behaves inappropriately but improves with ingestion of food or juice.

Because of the long duration of type-1 diabetes and frequent and often unrecognized hypoglycemia, this patient has significant impairment of glucose counter-regulation with absent glucagon and markedly blunted epinephrine response to hypoglycemia. That is, he is unable to mount an effective response to abnormally low blood glucose and the attendant dangers that can result. Furthermore, he has hypoglycemic unawareness, which frequently accompanies recurrent hypoglycemia and increases the risk of severe hypoglycemia developing. He is unaware when his blood glucose is dangerously low, because his body's mechanisms to recognize low blood glucose are defective. This is a common scenario in diabetes of long duration and manifests itself most commonly when efforts to achieve normal or near-normal glycemic control are attempted in such individuals. Because of his concern about the increasing frequency and severity of his hypoglycemic episodes and his frequent inability to recognize them, he is seriously considering "loosening up" his glycemic control to reduce the hypoglycemia. He understands that this may have detrimental consequences with increased microvascular complications but feels that the dangers of severe hypoglycemia are greater and more immediate.

This hypothetical patient has been striving to achieve the best glycemic control possible based on the understanding that the risk of developing microvascular complications is minimised so long as his day-long glycemia approaches non-diabetic levels. Despite being on the most advanced and flexible form of insulin delivery system currently available and having achieved significant improvement in glycemic control to recommended goals, he is plagued by frequent and potentially dangerous bouts of hypoglycemia. To alleviate this situation, yet allow him to maintain the same level of glycemic control, the methods provided herein are used, and in one embodiment, a second pump device, which can be identical to the first but has a glucagon cartridge in place of the insulin cartridge, is employed. The device is independently cannulized and independently controlled for continuous subcutaneous infusion of glucagon when desired.

In one embodiment, the patient is instructed to practice as follows. After taking a meal, the patient administers his prandial insulin (3-8 units) and at the same time programs his glucagon pump to administer about 162 µg of glucagon per hour subcutaneously over three hours and timed to begin 2-3 hours after administration of his prandial insulin. In one embodiment, the above instructions are included in a kit with a composition for the control of hypoglycemia. In this example, unlike in Example 1.A.ii, the continuous release of glucagon produces a smoother profile with less of a peaked appearance and decay period than with a single subcutaneous injection of glucagon. The increased availability of glucagon during this patient's period of greatest susceptibility to hypoglycemia substantially decreases both the likelihood and severity of such events. To offset the glucose-raising potential of subcutaneous administered glucagon, the dosage of infused insulin can be increased to maintain euglycemia during the period of glucagon administration. By administering glucagon in this way, the patient is provided with sufficient glucagon to serve as a cushion or buffer to the unopposed action of insulin so as to prevent the risk of a hypoglycemic episode. Thus, the administration of glucagon enables the patient to maintain good glycemic control without the excessive risk of frequent and severe hypoglycemia.

B. Insulin Administered Parenterally

In one embodiment, glucagon can be administered by pump and insulin administered parenterally, including by pump or other subcutaneous administration. In one embodiment, pumps suitable for insulin administration are also suitable for glucagon administration. Insulin can be administered parenterally as described in Example 1.A.i. Instead of injecting glucagon as described in Example 1.A.i, however, the pump is programmed (or actuated) to deliver glucagon continuously between hours 2 and 5 after the meal. The total dose of glucagon released is approximately 121-324 milliunits over those three hours, this being sufficient to provide protection from hypoglycemia. Alternatively, the amount of glucagon released is approximately 72-216 milliunits over those three hours, this being sufficient to provide protection from hypoglycemia.

C. Insulin Administered Transdermally [Including Patch and Topical Cream]

In one embodiment, insulin can be administered transdermally. In accordance with Example 1.C, the patient administers his insulin needs by use of transdermal patch (or cream). Instead of administering the glucagon parenterally as described in that example, however, the patient uses an insulin pump (containing not insulin but glucagon) to administer glucagon to prevent hypoglycemia in the early morning. Before going to bed, the patient programs his pump to deliver 50-120 milliunits of glucagon to be administered subcutaneously between the hours of 01:00 and 02:00. the period during which he is most susceptible to hypoglycemia. By so doing, the patient is able to maintain euglycemia using the methods of the present embodiment, without the risk of hypoglycemia occurring during his sleep.

D. Insulin Administered by Inhalation [Including Pulmonary, Buccal Nasal and Sublingual]

In accordance with Example 1.A.i, the patient administers insulin by inhalation rather than by subcutaneous injection. It will be understood by those skilled in the art that similar methods can be employed when insulin is administered buccally, nasally or sublingually. The patient will either continue to administer his basal need via GLARGINE (LANTUS), or he will utilize an insulin inhaler to administer basal insulin needs. The patient will administer his prandial insulin need (equivalent to between 5 and 10 units administered by subcutaneous administration) using his insulin inhaler (either pulmonary, nasally, buccally or sublingually). Instead of injecting glucagon as described in Example 1.A.i, however, an insulin pump (containing glucagon rather than insulin) is programmed (or actuated) to subcutaneously deliver glucagon continuously between hours 2 and 5 after the meal. The total dose of glucagon released is approximately 121-500 milliunits over those three hours, this being sufficient to provide the patient with protection from hypoglycemia during his period of greatest susceptibility. Alternatively, the amount of glucagon released is approximately 72-216 milliunits over three hours.

EXAMPLE 3

Co-Administration of Glucagon and Insulin, Admixed, by Pump for the Control of Diabetes and Prevention of Hypoglycemia Some embodiments of the methods of the invention can also be practiced using pump-based administration of an admixture of both insulin and glucagon. This method provides protection from hypoglycemia in direct proportion to the amount insulin used and with a built in delay. It also replaces basal levels of glucagon throughout the day and especially after meals, as it will also be administered with the basal insulin administered by the pump. This embodiment can be practiced using standard pumps currently available and described in Example 2. One difference is that the insulin cartridges used will contain a mixture of insulin and glucagon (optionally modified release glucagon), with the glucagon component being between 32-96 or 41-96 mU to be administered each hour of desired protection (prevention of hypoglycemia). In some embodiments, the amount of glucagon administered subcutaneously can be about 0.1 ng/kg/min. of desired protection to about 20 ng/kg/min., 6 ng/kg/min. of desired protection to about 20 ng/kg/min. of desired protection, and is in some embodiments 12 ng/kg/min.

Figure 7:
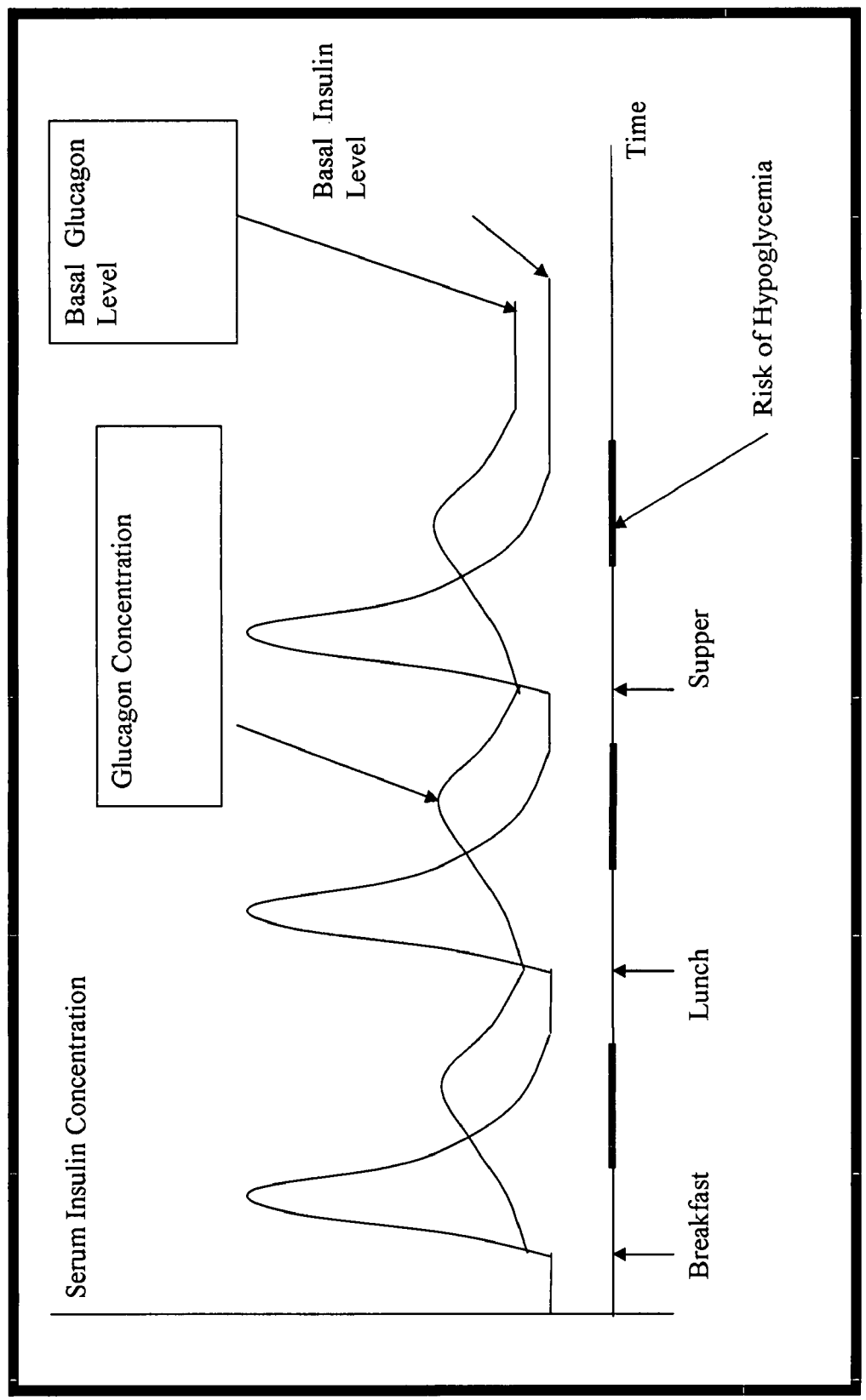
FIG. 7 is a graph illustrating the insulin and glucagon profiles of a hypothetical patient, as described in Example 3. showing for both drugs a very simple, flat line graph (basal insulin and glucagon infusions) punctuated by peaks (corresponding to prandial insulin and glucagon infusions) corresponding to when glucagon and insulin are administered in an admixed formulation.

The insulin/glucagon mixture is then administered by pump (for both basal and prandial insulin). The resulting glucagon (modified glucagon) plasma concentrations will map onto the insulin profile but with the attenuating characteristics of the glucagon variant used. This is illustrated in FIG. 7. This method will provide protection from hypoglycemia over the period of susceptibility as required. In one embodiment, the pump is equipped with a glucose sensor (see U.S. Pat. No. 5,474,552).

EXAMPLE 4

Co-Administration of Glucagon and Insulin, Orally, for the Control of Diabetes and Prevention of Hypoglycemia The delivery of large molecules (e.g. proteins) orally is well known in the art. Typically this involves enteric administration (see U.S. Pat. No. 5,641,515). In one embodiment, similar methods are used to deliver glucagon orally. In a typical scenario involving the oral delivery of a mixture of insulin and glucagon, the patient takes an enteric tablet containing insulin appropriate to his prandial up to an hour before eating. The insulin component is designed for rapid onset once it begins release. The glucagon component is designed to release later than the insulin component, in one embodiment by 2-3 hours. Optionally, modified glucagon with a long half life can be used to ensure that glucagon levels are elevated over an extended period. Administered in this way, the glucagon will be correctly and appropriately timed to prevent hypoglycemia. In another embodiment, the patient administers his insulin using any of the methods described herein and administers a glucagon pill as required, for example, with each of his meals, to prevent hypoglycemia.

EXAMPLE 5

Compositions for Glucagon Suspension and Methods of Characterizing Them

This Example demonstrates one composition of one embodiment of the invention that was found to be useful for the storage of a glucagon and a method of one embodiment of the invention for verifying that the composition for storing glucagon provides the desired degree of stability for the glucagon. GlucaGen® was mixed in 5% mannitol in Water For Injection at 200 μg/mL and 500 μg/mL in infusion pump cartridges. This solution was kept at 30° C. for set durations of time. Following the set durations, the pH and remaining percent glucagon were tested. The percent of remaining glucagon was determined by HPLC analysis. The results are presented below in Table 2 for 200 μg/mL GlucaGen® and Table 3 for 500 μg/mL GlucaGen®. Results are from 3 sets of tests and the data is expressed as mean±s.e.m.

TABLE 2

| Time Point | pH | Remaining Glucagon (%) Relative to Time Zero |
| --- | --- | --- |
| Time Zero | 3.36 ± 0.01 | 100.0 ± 2.3 |
| 3-hr | 3.45 ± 0.04 | 101.1 ± 1.5 |
| 6-hr | 3.53 ± 0.03 | 95.2 ± 4.3 |
| 9-hr | 3.64 ± 0.04 | 99.1 ± 5.3 |
| 24-hr | 3.79 ± 0.04 | 89.3 ± 0.7 |

TABLE 3

| Time Point | pH | Remaining Glucagon (%) Relative to Time Zero |
| --- | --- | --- |
| Time Zero | 2.98 ± 0.00 | 100.0 ± 1.1 |
| 3-hr | 3.10 ± 0.02 | 100.2 ± 1.6 |
| 6-hr | 3.08 ± 0.01 | 99.4 ± 0.9 |
| 9-hr | 3.13 ± 0.03 | 101.2 ± 0.1 |
| 24-hr | 3.21 ± 0.01 | 93.8 ± 2.1 |

All solutions at the time of preparation were clear and colorless. The solutions remained clear and colorless throughout the compatibility study. No visible particles were observed. Substantial amounts of glucagon remain in the mannitol solution, even at high concentrations and for all of the time periods examined, including 24 hours. Additionally, the higher concentration of glucagon resulted in a higher relative percent of glucagon remaining. Thus, it appears that this combination is sufficient for maintaining glucagon in solution for useful periods of time.

EXAMPLE 6

Compositions for Glucagon Suspension and Methods of Characterizing Them

This example demonstrates a composition and one method of one embodiment of the invention by which such a composition can be analyzed to determine the lifetime of a glucagon solution experiencing active, or "wear," use. Samples of Glucagon Infusate at 200 μg/mL and 500 μg/mL in 5% mannitol solution were prepared. An aliquot of approximately 3 mL of each Glucagon Infusate sample was added to an individual cartridge in triplicate. Cartridges were inverted 10 times and a 0.5-mL aliquot was removed from each as "Time Zero" for HPLC analysis. The filled cartridges were placed on a Platform Shaker set at 50 RPM and incubated at 30° C. for 24 hours. At 3, 6, 9, 12 and 24 hours the cartridges were removed from the oven, inverted 10 times and a 0.5-mL aliquot was dispensed from each for HPLC analysis. Appearance and pH were also recorded at each time-point.

All solutions at the time of preparation were clear and colorless. The solutions remained clear and colorless throughout the stability study. No visible particles were observed. Additional results are presented in Tables 4 and 5.

TABLE 4

| Time Point | pH | Remaining Glucagon (%) Relative to Time Zero |
| --- | --- | --- |
| Time Zero | 3.47 ± 0.05 | 100.0 ± 2.7 |
| 3-hr | 3.45 ± 0.03 | 85.7 ± 4.2 |
| 6-hr | 3.47 ± 0.03 | 83.6 ± 2.6 |
| 9-hr | 3.50 ± 0.00 | 82.7 ± 2.9 |
| 12-hr | 3.50 ± 0.03 | 75.5 ± 6.0 |
| 24-hr | 3.53 ± 0.01 | 48.9 ± 1.0 |

TABLE 5

| Time Point | pH | Remaining Glucagon (%) Relative to Time Zero |
| --- | --- | --- |
| Time Zero | 3.05 ± 0.02 | 100.0 ± 0.5 |
| 3-hr | 3.01 ± 0.01 | 98.5 ± 1.2 |
| 6-hr | 3.02 ± 0.00 | 97.6 ± 0.7 |
| 9-hr | 3.05 ± 0.00 | 95.1 ± 2.0 |
| 12-hr | 3.03 ± 0.00 | 95.0 ± 3.6 |
| 24-hr | 3.00 ± 0.00 | 93.1 ± 1.1 |

With continuous shaking at 50 RPM, GlucaGen® in 5% mannitol at 200 μg/mL showed 25% glucagon loss after being stored at 30° C. for 12 hours, and about 50% glucagon loss after being stored at 30° C. for 24 hour. GlucaGen® in 5% mannitol at 500 μg/mL exhibited 7% loss over 24 hours. Thus, even with lower concentrations of glucagon, e.g. 200 μg/mL, a substantial amount of glucagon remains in solution after extended periods of time. Furthermore, it appears that the greater concentration of glucagon results in a more stable formulation, even through active shaking of the formulation for 24 hours.

In one embodiment, the glucagon or variant thereof, is stored at high concentrations. High concentrations may be, for example, greater than 100 micrograms/mL. In one embodiment, high concentrations are more than 200, 200-300, 300-400, 400-500, 500, 500-600, 600-800, 800 or more μg/mL glucagon, up to the saturation (or super-saturation) limit,. In one embodiment, less active forms of glucagon are stored at higher concentrations. This allows for greater stability of the glucagon solution and for one to administer a larger volume of glucagon solution to a recipient.

EXAMPLE 7

Very Low Dose (VLD) Glucagon can be Used to Elevate Blood Glucose in Insulin-Treated Diabetic Patients This example demonstrates the effectiveness of applying a low dose of glucagon to a patient via a particular route of administration to elevate the blood glucose level of the patient. This example describes clinical testing in which the level of glucagon required to increase glucagon and glucose blood levels was examined. As explained in more detail below, the results show that the methods of some embodiments of the invention can be used to avert insulin induced hypoglycemia.

A. 0.8 to 4 ng/kg/min. of Glucagon

Six patients with Type 1 diabetes were stabilized overnight at blood glucose levels of 90 to 120 mg/dl in a nocturnal titration period. Stabilization of blood glucose levels in this range of 90 to 120 mg/dL was accomplished using insulin doses that generally varied between 0.65 to 1.4 units/hour.

The following morning, these patients were administered glucagon subcutaneously by continuous infusion pump over a range of 0.8 to 4.0 ng/kg/min. (specific doses were 0.8, 1.6, 2.4, 3.2 and 4.0 ng/kg/min) of glucagon along with their usual doses of insulin. Each dose level within this range was infused for 2 to 3 hours. Under this lower range of doses, 0.8-4.0 ng/kg/min. of glucagon, there were no explicit consistent trends in the glucagon or glucose levels of the patients.

B. 8 to 16 ng/kg/min. of Glucagon

After undergoing a nocturnal titration period in which their blood glucose levels were maintained between 90 and 120 mg/dl, six patients were dosed with glucagon in a range of 8 to 16 ng/kg/min. Glucagon was administered subcutaneously by continuous infusion pump. The specific doses administered were 8, 12 and 16 ng/kg/min; each dose level was infused for 3 hours. Patients were maintained on their standard basal levels of insulin by continuous subcutaneous pump administration prior to the administration of the glucagon.

The 8 ng/kg/min. dose of glucagon did result in a significant rise in both glucose and glucagon, approximately doubling the blood glucagon levels and resulting in an increase of approximately 40% for blood glucose levels. Thus, a dose of 8 ng/kg/min. can elevate blood glucose levels in these patients. Moreover, even those lower ranges tested, while not sufficient for elevating blood glucose levels under these test conditions, could be sufficient for preventing hypoglycemia induced through insulin administration in some patients.

Figure 8:
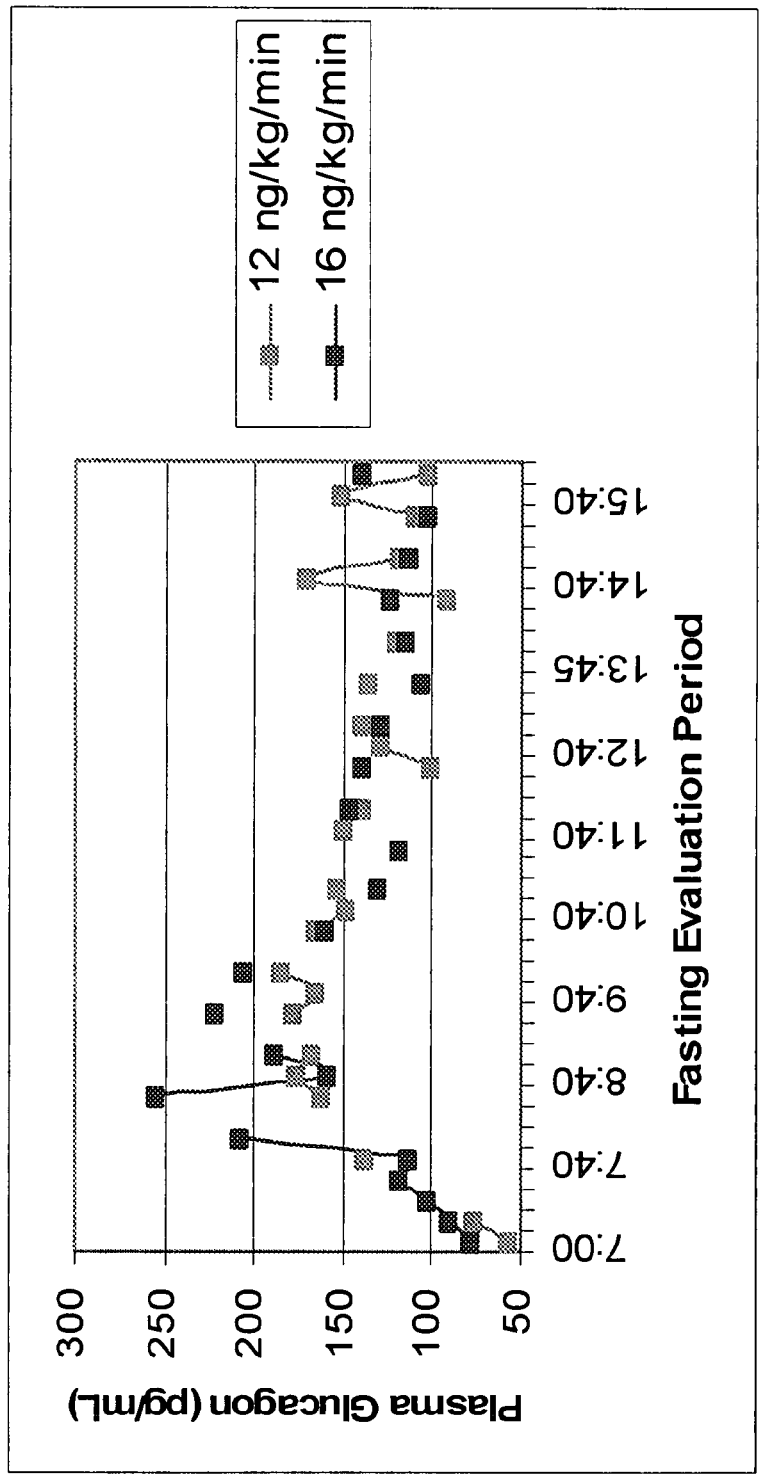
FIG. 8 is a graph illustrating the effect of continuous glucagon infusion on mean glucagon levels, as described in Example 7.
Figure 9:
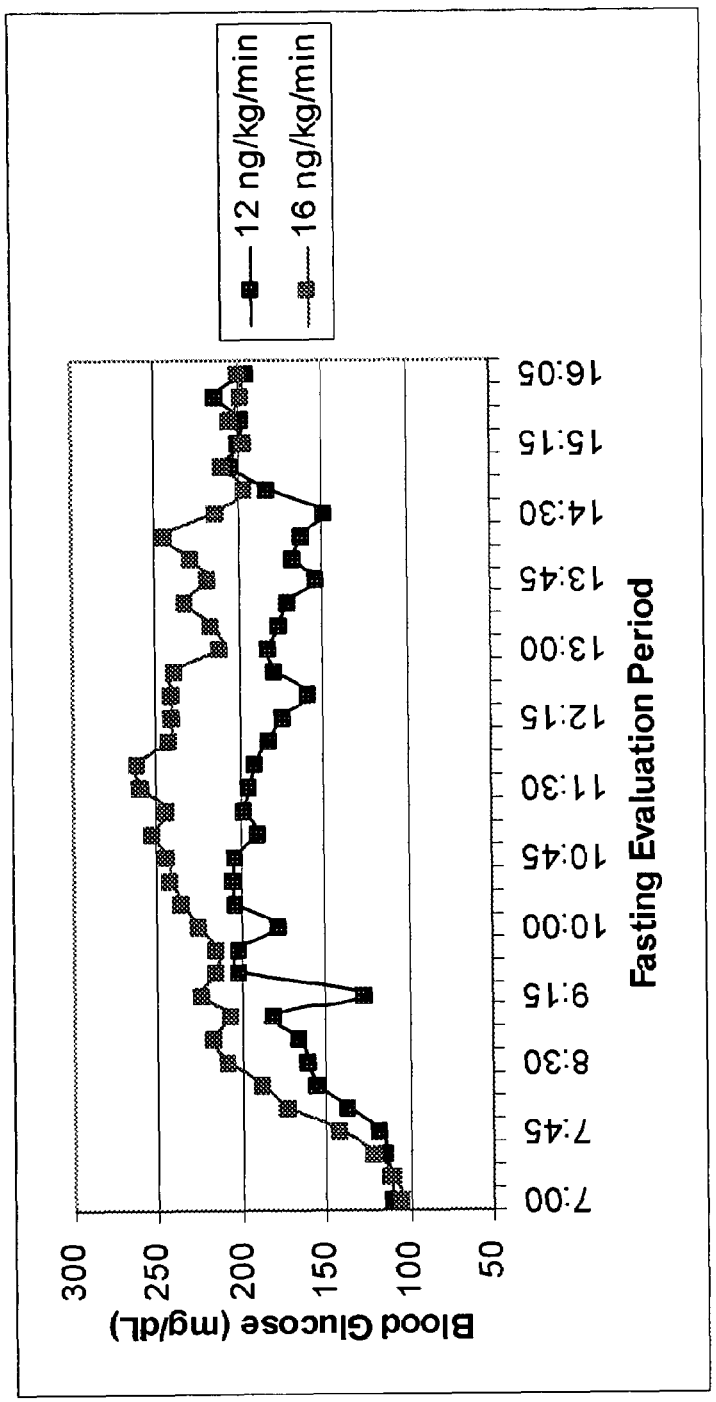
FIG. 9 is a graph illustrating the effect of continuous glucagon infusion on mean glucose levels, as described in Example 7.
Figure 10:
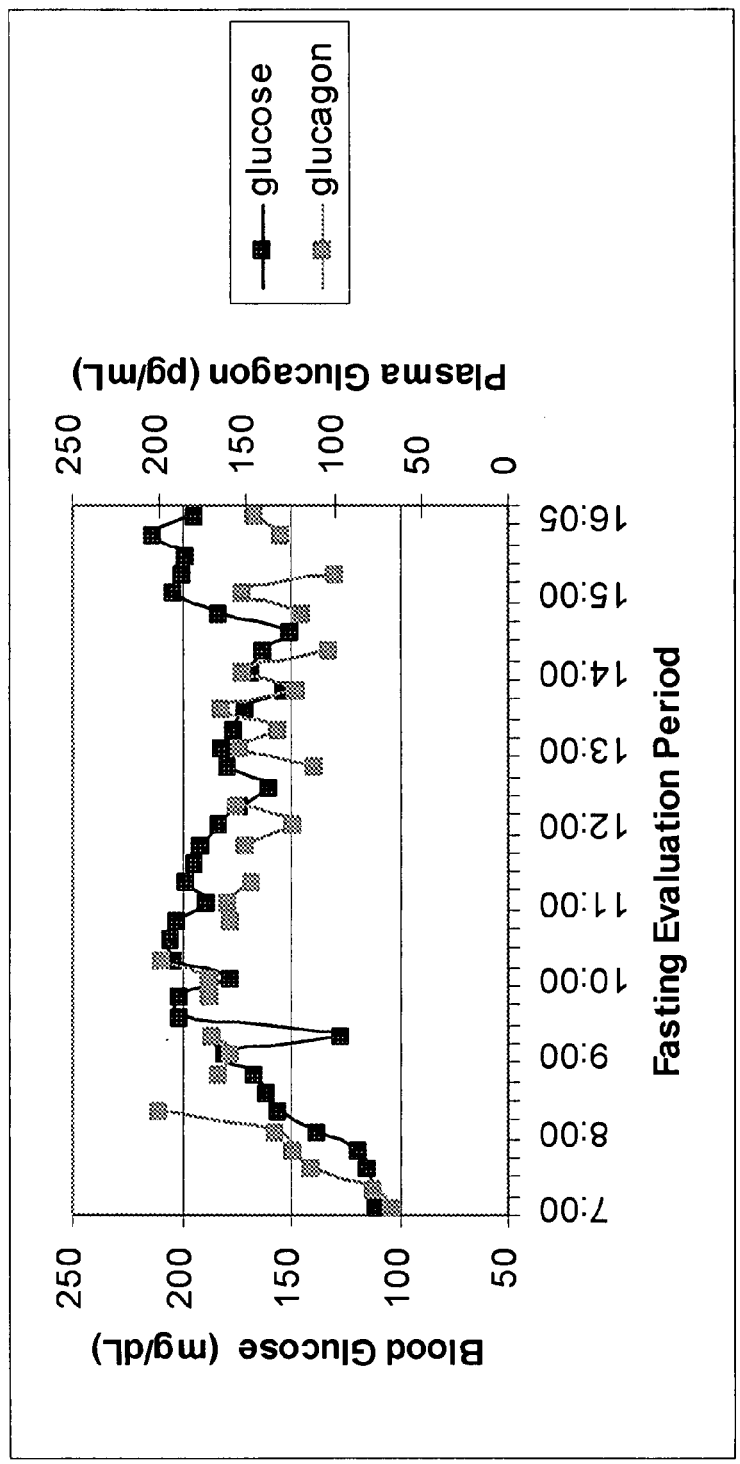
FIG. 10 is a graph comparing the effect of continuous glucagon infusion at 12 ng/kg/min. on mean glucose and glucagon levels, as described in Example 7.
Figure 11:
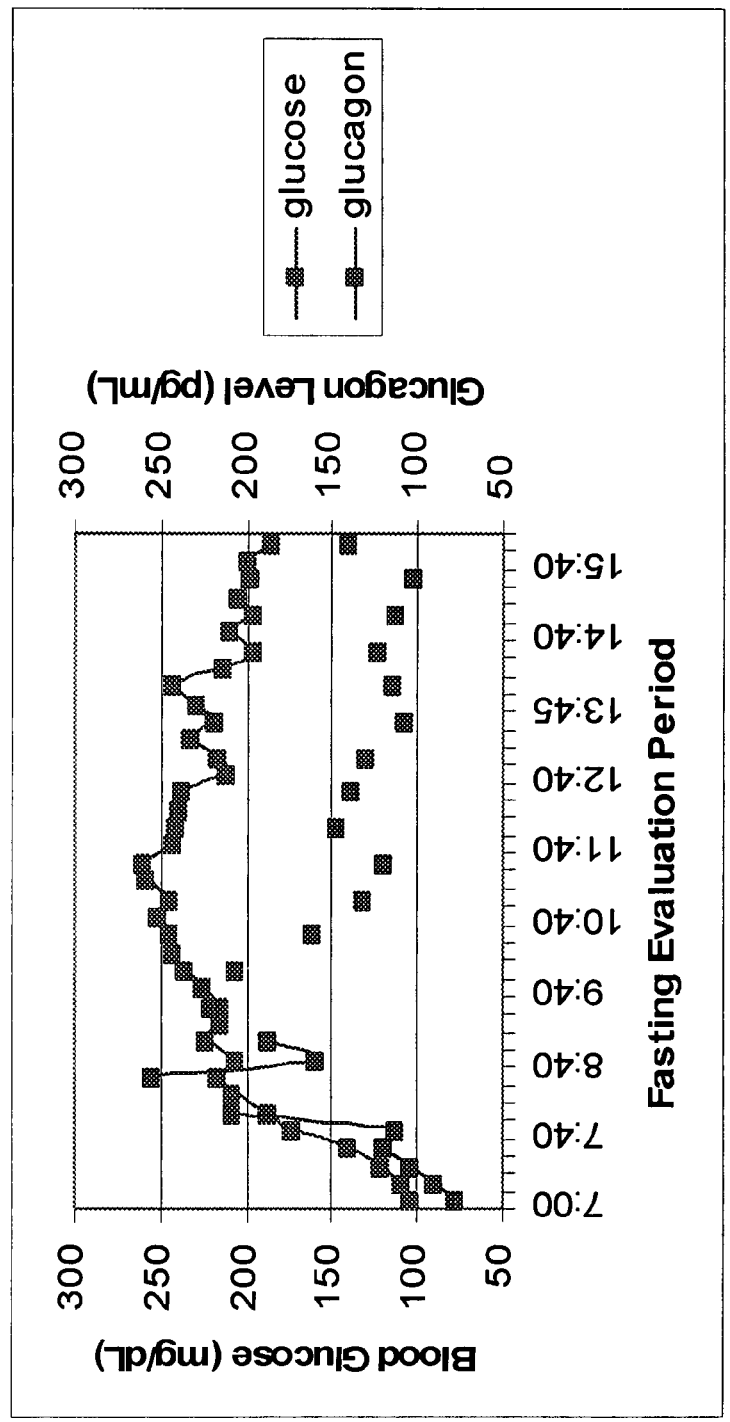
FIG. 11 is a graph comparing the effect of continuous glucagon infusion at 16 ng/kg/min. on mean glucose and glucagon levels, as described in Example 7.

In 3 patients, an infusion of 12 ng/kg/min. of glucagon subcutaneously for 9 hours resulted in elevated plasma glucagon levels that were sustained for 6 to 8 hours in the range of 100 to 200 pg/ml (see FIG. 8). The peak mean plasma level at the 12 ng/kg/min. dose was 185 pg/ml. The blood glucose level of the patients was also substantially elevated (see FIG. 9). This clearly demonstrates that sustained, very low, doses of glucagon can be administered to patients, effectively, over a prolonged period of time with the desired result of controllably elevating blood glucose levels.

Two patients were treated with 16 ng/kg/min. of glucagon subcutaneously for 9 hours. In both subjects, dosing with 16 ng/kg/min. resulted in higher peak plasma glucagon levels than were achieved on the 12 ng/kg/min. dose (see FIG. 8). In both subjects, the peak level was achieved during the first 3 hours of the infusion and then tended to decrease to levels seen at with the 12 ng/kg/min. dose. At the 16 ng/kg/min. dose level the peak mean plasma level was about 254 pg/mL. Despite the decline in glucagon levels during the latter part of the infusion, glucose levels remained elevated throughout the course of the infusion (see FIGS. 8-11). Glucose levels achieved at the 16 ng/kg/min. dose were generally higher than those achieved at the lower dose of 12 ng/kg/min. (see FIG. 9).

Subjects described above were generally maintained on their basal rate of insulin throughout the fasting evaluation period. The insulin administered varied between patients and over time from 0.5 to 1.8 units of insulin per hour. Glucose levels began to rise as early as 30 minutes after the glucagon infusion was started. On average, this rise was sustained throughout the glucagon infusion.

These results demonstrate that very low doses of continuously administered glucagon can be used to increase blood glucose levels in insulin treated patients not experiencing hypoglycemia.

These data confirmed that the administration of a dose of glucagon in the range of 8 to 16 ng/kg/min. yields an increase in the plasma glucagon levels in the range of about 100 to 200+ pg/mL and that these levels can be maintained over a substantial period of time. The normal reference range for glucagon is 50 to 150 pg/mL. As will be appreciated by one of skill in the art, these results demonstrate that low, continuous dosing of glucagon can elevate blood glucose levels in diabetic patients and so provides a means to prevent hypoglycemia in those patients. These results demonstrate the amount of glucagon required to induce elevated blood glucose levels. One of skill in the art will appreciate that lower glucagon doses may be used to prevent hypoglycemia in other patients, but the doses of 8 ng/kg/min. and higher exemplified here are effective in preventing hypoglycemia. The actual minimal amount can vary between patients, and given the present disclosure, one of skill in the art can readily determine what the minimal amount can be for a particular patient.

Interestingly, the levels achieved in the present example with VLD glucagon in amounts of 12 to 16 ng/kg/min are similar to the levels seen in non-diabetics in response to conditions of experimentally-induced hypoglycemia.

The following Example demonstrates how these doses of glucagon can prevent hypoglycemia even when there is an insulin challenge, i.e., a dose of insulin that would otherwise induce hypoglycemia in the patient.

EXAMPLE 8

Prevention of Insulin Induced Hypoglycemia with Glucagon

This example demonstrates that insulin induced hypoglycemia (a blood glucose less than 50 mg/dl for this example) can be prevented with low doses of continuously administered glucagon. The study was arranged in three visits. The first visit involved increasing the amount of insulin administered to the subjects without supplying any glucagon; the subjects' blood glucose levels were monitored. This first study defined the insulin challenge needed to induce hypoglycemia in these patients. In the following two visits, two different doses of glucagon were administered to the patients and the patients' blood glucose levels monitored to determine whether the glucagon prevented or delayed any hypoglycemia that would have otherwise been induced by the insulin challenge. Thus, by comparing the glucose levels measured in the first visit with those in the later two visits, one is able to determine whether the glucagon prevented hypoglycemia.

Figure 12:
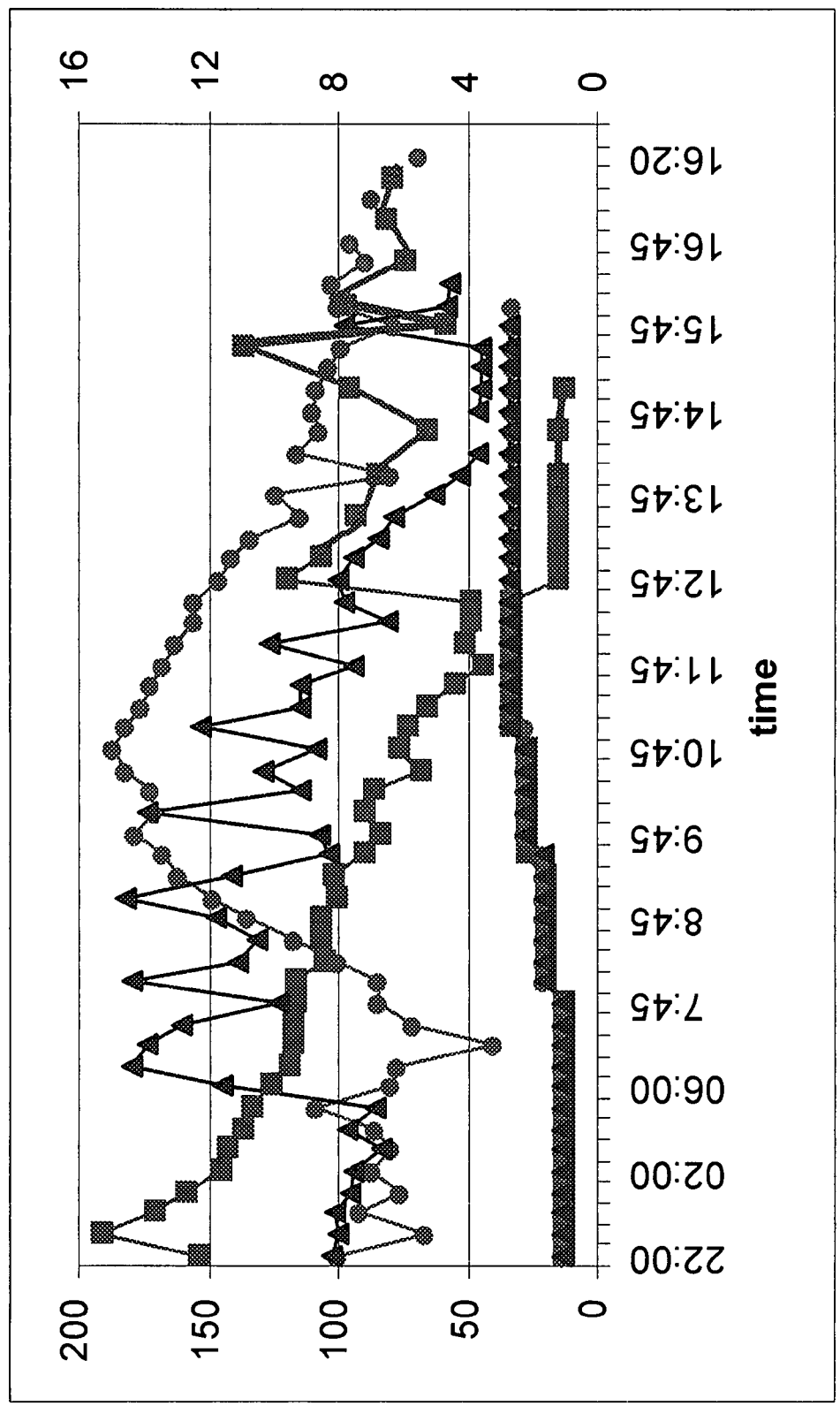
FIG. 12 is a graph comparing the effect of various doses of glucagon (0, 8. and 16 ng/kg/min. of glucagon) on increasing insulin levels (from about 1 to about 2.7 units). The graph demonstrates that low doses of glucagon are capable of preventing insulin induced hypoglycemia, as described in Example 8.

During the first visit, each subject's basal insulin rate was titrated upward (in 50% increments every 90 minutes (for example, from a basal rate of 1.0 unit/hour, to 1.5 units per hour for 90 minutes, to 2.0 for 90 minutes, to 2.5)) to induce hypoglycemia (blood glucose less than 50 gm/dl). The results for one patient are shown in FIG. 12, with visit 1 represented by squares. The lower set of lines trace the increases or decrease of insulin administered to the subject. The insulin administered was returned to basal rate of infusion (and glucose administered) after 12:30; thus, the spike after 12:30 is to be expected. Blood sugar levels were allowed to vary between 50 mg/dL and 350 mg/dL. Glucose levels lower than 50 mg/dL were considered indicative of hypoglycemia.

During visits 2. and 3. subjects received a continuous infusion of various doses of glucagon (starting at 7:00 a.m. and ending around 4:00 p.m.) to determine whether that dose would avert the insulin-induced hypoglycemia or delay the time to onset of hypoglycemia that was observed in the first visit. Because the onset of action on glucose levels is around 60 to 90 minutes, the glucagon infusion was started one hour before the insulin infusion rate was stepped up.

Two different doses of glucagon were examined, a dose at 8 ng/kg/min. (triangles) and a dose at 16 ng/kg/min. (circles). The results of these low doses of continuous glucagon on blood glucose levels are shown in FIG. 12. As shown in FIG. 12, the 8 ng/kg/min. dose of glucagon (triangles) maintained a higher level of blood glucose in the patient compared to the test in which no glucagon was administered. Again, the control line, (no glucagon, only increasing insulin, squares) effectively ended at 12:30; past this point on the graph, no insulin was administered, and thus the comparison should be made between 7:00 and 12:30. Hypoglycemia was delayed for approximately two hours.

As shown in FIG. 12, the 16 ng/kg/min. dose (circles) maintained blood glucose levels substantially above the control level and even above the 8 ng/kg/min. (triangles) glucagon dose for a substantial period of time. Additionally, while the 8 ng/kg/min. dose was able to prevent hypoglycemia and kept blood glucose levels above 50 mg/dL, the 16 ng/kg/min. dose maintained blood glucose levels closer to 100 mg/dL. This indicates the effectiveness of both of these ranges, as well as dose dependency.

The lines in the lower section of the graph (i.e., triangle, square, and circle marked lines beneath the 50 mg/dl line in FIG. 12) represent the steps in insulin infusion over the time of the test. Thus, the lower square marked line is indicative of insulin levels during visit 1. and the lower circle and triangle marked lines are indicative of insulin levels during visits 3 and 2 respectively.

In another patient, the effect of the 8 ng/kg/min. dose was not as pronounced as that shown in FIG. 12. Thus, this patient would require a higher dose or infusion rate to prevent hypoglycemia. This is demonstrated by the 16 ng/kg/min. dose data, which demonstrated an effect similar to that shown in FIG. 12 for the first patient, i.e., elevated blood glucose levels above 200 mg/dl.

Figure 13:
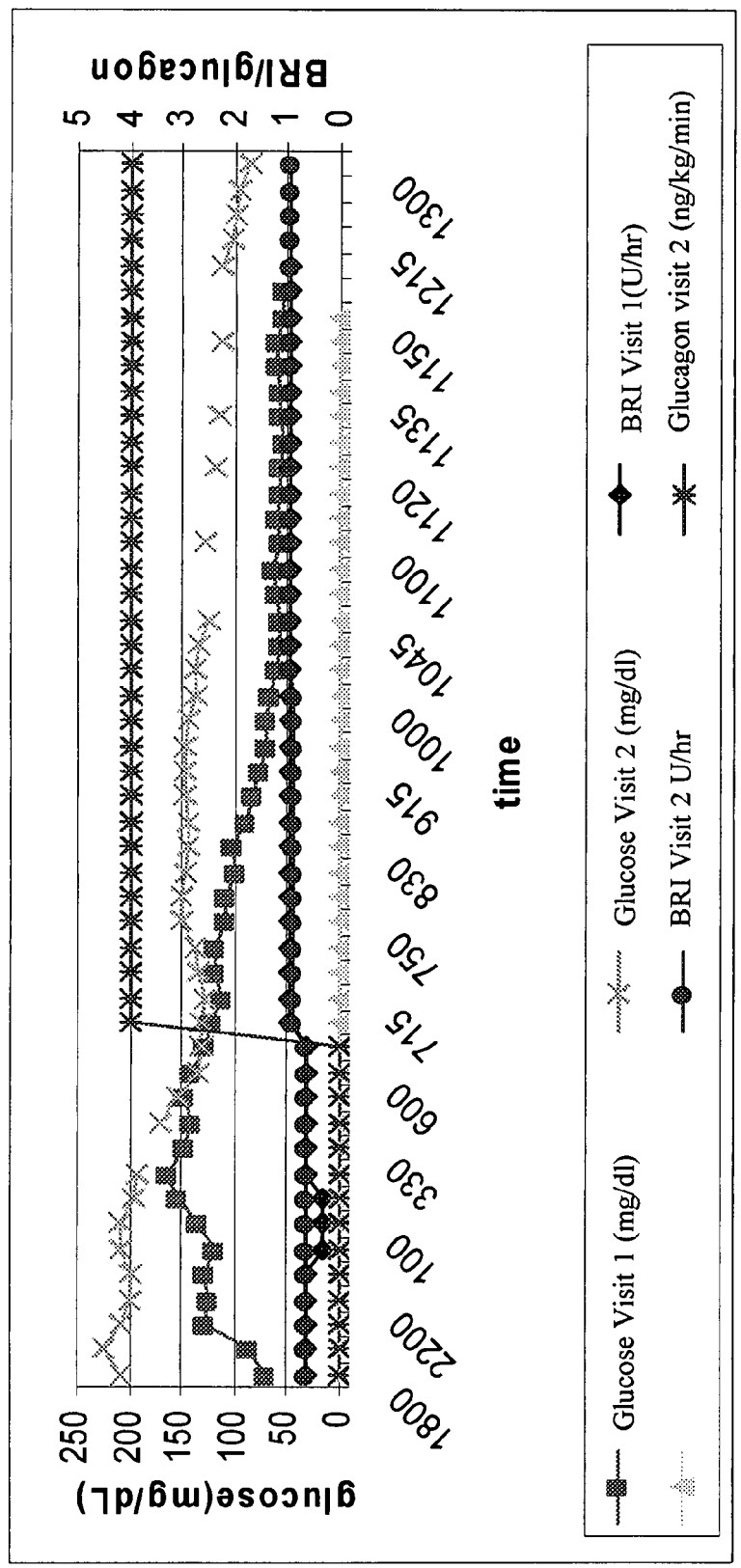
FIG. 13 is a graph displaying the effect of a low dose of glucagon on blood glucose levels and how it can prevent hypoglycemia, as described in Example 8.

In addition to the above glucagon levels tested, the effectiveness of a lower level of glucagon was also tested, using a similar protocol. In another patient examined, the above experiment was repeated with a lower dose of glucagon, 4.0 ng/kg/min., and a slightly lower upper limit of insulin (1.5 fold the basal rate of insulin). The results are displayed in FIG. 13. As can be seen in the graph, while an increase in the BRI during a first visit (diamonds) resulted in lower blood glucose levels (squares), the administration of 4 ng/kg/min. of glucagon in a second visit (asterisk) helped to maintain elevated blood glucose levels ("X") as well as delay the decrease in blood glucose levels, even when insulin levels were increased (circles). In this patient, while the raised level of insulin would have otherwise induced hypoglycemia, the presence of 4.0 ng/kg/min. of glucagon was sufficient to prevent hypoglycemia from occurring.

In addition to the above identified benefits of administering low doses of glucagon to prevent hypoglycemia, there appears to be a prolonged benefit to this dosing schedule for subcutaneously administered glucagon. Blood glucose levels remained elevated even after the glucagon had ceased to be administered (see the section of FIG. 12 following 4:00 p.m.).

Thus, continuous administration of glucagon is not required to maintain an extended period of elevated blood glucose levels.

The above methodology can be used to determine the appropriate amount of glucagon to administer to a particular patient. For example, testing patients who take greater amounts of insulin, for example 2-10, 10-20, 20-30. or more units of insulin per hour in this fashion can be used to determine the appropriate dosing regimen for glucagon to prevent hypoglycemia. In the above example, insulin amounts were increased by 1.5 to about 2.5 fold. In one embodiment, one increases the amount of glucagon proportionally as one increases the amount of insulin and then determines (via the above methodology) if the new glucagon dose is correct to prevent hypoglycemia. In this fashion, one can determine the appropriate dosage of glucagon for a particular patient. One of skill in the art will recognize that this relationship need not be 100% proportional and that some degree of routine experimentation can be useful in optimizing the final values. Additionally, one can use the above example to determine a dosing schedule to see how frequently glucagon actually needs to be administered. In some embodiments, rather than constant administration, glucagon is administered only 99-90, 90-80, 80-60, 60-40, 40-20, 20-10, 10-1 percent, or less of the time.

As will be appreciated by one of skill in the art, variations in the method of administration (e.g. patch, inhalation, topical creams, I.V., etc.) can also be examined using this methodology. Additionally, as will be appreciated by one of skill in the art, this methodology can be modified to determine the appropriate timing of the administration of glucagon to the patient. For example, the glucagon can be administered 1 hour before the insulin level is adjusted, and can be increased to 90 minutes or more or decreased to 45 minutes or less, for example, to determine if better control of glucose blood levels is maintained. As will be appreciated by one of skill in the art, the time of administration and method of administration can influence the dose requirements. Additionally, the importance of various additives can also be examined through the above methodology.

EXAMPLE 9

Determining an Amount of VLD Glucagon for the Prevention of Hypoglycemia

This example describes a clinical trial for demonstrating that glucagon administered in accordance with the present methods will function as desired in maintaining a desired blood glucose level. The method also provides means to determine the optimal ratio of insulin to glucagon for administration to a particular patient to prevent insulin-induced hypoglycemia.

Subjects report in the evening and are fed a standard meal at approximately 1700 to 1800 hr. They are instructed to bolus their usual dose of insulin through their pump based on carbohydrate counting. At 2000 hr, another pump (Pump 2) is initiated on the contra-lateral side of the abdomen with saline infused at the same rate as the insulin infusion. From approximately 2200 hr, subjects fast and are on their usual basal dose of insulin through CSII. Plasma glucose is checked with a YSI throughout the night every hour (or more frequently if necessary). The plasma glucose is maintained between approximately 100 and 125 mg/dl through adjusting the basal insulin rate and, if necessary, with the use of IV 5% Dextrose (if the plasma glucose decreases below 90 mg/dl) and IV Insulin (if their plasma glucose increases above 160 mg/dl).

From 0700 to 0800 hr, baseline blood samples are drawn and tested for plasma glucose, free fatty acids, ketone bodies, glucagon and insulin levels. At 0800 hr, subjects receive two times their usual basal dose of insulin through their Insulin Pump 1 to induce controlled hypoglycemia. Through Animas Pump 2. they receive VLD glucagon on the opposite side of the abdomen. The dose of glucagon administered is individualized based on previous studies. The selected dose is the highest dose that does not cause hyperglycemia (>180 mg/dl) in each individual study subject.

From 0800 to 1200 hr, blood is drawn every 5 to 10 minutes and YSI plasma glucose is determined. Blood is also drawn to measure free fatty acids, ketone bodies, glucagon and insulin levels every 15-30 minutes from 0800 to 1200 hr. Despite receiving a much higher than basal dose of insulin through CSII (continuous subcutaneous insulin infusion), the plasma glucose levels of the study subjects does not decrease to hypoglycemic levels (<60 mg/dl), due to the simultaneous continuous subcutaneous infusion of glucagon, which counteracts the glucose lowering effects of the high basal dose of insulin. If during the study, it is found that the subject's plasma glucose begins to decrease and consistently falls below 90 mg/dl on 2 consecutive occasions, the dose of the continuous glucagon infusion is titrated upwards by 25% to counter the fall in plasma glucose. On the other hand, if the subject's plasma glucose begins to increase and rises more than 25% in 1 hour, the dose of the glucagon infusion is titrated downwards by 25% to counter the increase in blood glucose. Thus, this trial demonstrates that the combination of a small amount of glucagon with insulin can prevent insulin-induced hypoglycemia. Both the insulin and the glucagon can be administered subcutaneously.

By the above methodology, one can also test various forms of glucagon formulations and methods of administration. Thus, one can determine the optimal timing and mode of delivery for glucagon or a glucagon mimetic or variant, or formulations of them. One can also use these methods to test the suitability of other hypoglycemic and hyperglycemic substances for the methods and compositions herein disclosed.

EXAMPLE 10

Preventing Nocturnal Hypoglycemia

This example demonstrates one method for demonstrating that a composition, for example, of glucagon, glucagon variants, or formulations thereof, is effective in preventing blunt insulin induced nocturnal hypoglycemia in humans. Additionally, it provides a method for testing the effectiveness of a glucagon or variant or formulation of either for preventing nocturnal hypoglycemia.

Two hours (~1800 h) after a standardized dinner meal, subjects receive twice their normal dose of insulin to induce the development of nocturnal hypoglycemia via a first pump. At 2200 h, they receive an infusion of the glucagon via a second pump (CSI). The blood glucose level is then monitored throughout the night. An adequate dose of glucagon prevents the blood glucose levels from decreasing to hypoglycemic levels. Both the glucagon and insulin can be administered subcutaneously.

EXAMPLE 11

Administering Low Doses of Glucagon to Prevent Loss of Hypoglycemic Awareness

To prevent loss of hypoglycemic awareness in a subject taking insulin, one administers to that subject more than 5 to about 16 ng/kg/min of glucagon subcutaneously to the subject to prevent the blood glucose level from entering an undesirable, hypoglycemic level (e.g. less than 50 mg/dL). To determine that the dose administered is sufficient, blood glucose levels can be measured throughout various time points in a test period to ensure that the subject's glucose level does not drop below a certain point (e.g., less than 50 mg/dL). Such testing can also be used to optimize the dose of glucagon administered to the patient. The administration of glucagon is chronic, i.e., through the preventive administration of a low dose of glucagon, a patient will avoid hypoglycemia and so not develop hypoglycemic unawareness due to repeated hypoglycemic episodes through prolonged insulin use. Alternatively, one can administer between 0.1 to about 20 ng/kg/min or 4.0 to about 16 ng/kg/min. of glucagon to the patient.

EXAMPLE 12

Administering Low Doses of Glucagon to Recover Hypoglycemic Awareness

A patient suffering from a loss of hypoglycemic awareness can be identified by screening to determine if the patient can identify when his or her blood glucose levels have dropped below 70 mg/dl of blood glucose. Once identified, one then administers an appropriate dose, in one embodiment that dose is 8-16 ng/kg/min., of glucagon subcutaneously to the subject to prevent the blood glucose level from declining to a level (e.g. less than 50 mg/dL).

Blood glucose levels can be taken throughout various time points to determine that the subject's glucose level has not dropped to a hypoglycemic point. These measurements can also be used to optimize the amount of glucagon administered to the patient. Through the administration of glucagon, a patient will experience fewer hypoglycemic episodes, and his or her awareness of hypoglycemia will improve. The subject's awareness of hypoglycemia can be tested, as described above, by determining if the subject can identify when his or her blood glucose level is below a certain point (e.g., 70 mg/dl).

Various doses, various forms of formulations, and various methods of application (administration) can all be tested using the above methodology to determine the optimal dosage, or if a formulation or method of administration is optimal for the prevention of hypoglycemia.

EXAMPLE 13

Co-Administration of Glucagon Transdermally and Insulin for the Control of Diabetes and Prevention of Hypoglycemia [Including Patch and Topical Cream]

The use of transdermal patches for the delivery of therapeutic drugs is increasingly more common. Patches provide a non-invasive and easy method of delivering some drugs to the bloodstream. Nicotine and hormone replacement therapies are perhaps the best known uses of this technology. One of the characteristics of drug delivery by transdermal patch is that the rate of delivery is typically constant and persists for a long period of time (as long as the patch is worn). This characteristic has proven beneficial in the area of pain management (FENTANYL) and nicotine replacement therapy, in which long duration flat profiles are ideal. This characteristic makes the transdermal patch suitable for basal replacement of insulin or glucagon. See PCT patent publication No. WO0243566, incorporated herein by reference.

Fast-acting patches are also known. The delivery of proteins (insulin in particular) transdermally into the bloodstream in well under an hour is reported in U.S. Pat. No. 5,707,641. incorporated herein by reference. The ability to deliver other proteins in the same way and using similar formulations is also recited. Glucagon can accordingly be administered in such a manner.

Figure 6:
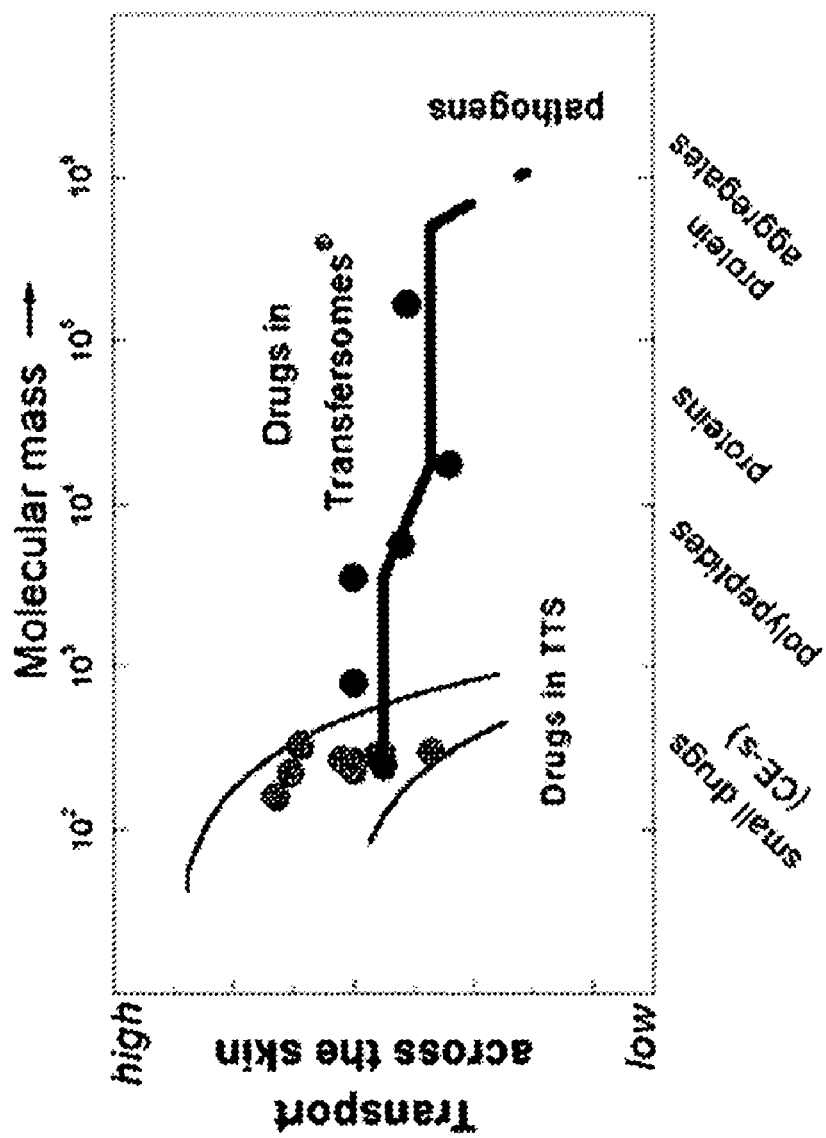
FIG. 6 illustrates the effect of molecular weight and lipophilicity on the rate of transdermal transport in case of permeation (upper and lower gray curve for the more or less lipophilic substances, respectively) or of the TRANSFEROME® mediated penetration (black line and bullets). Dotted black bullets represent the commercial drugs in transdermal patches.

Development of insulin patches is currently being pursued by Helix BioPharma, from Canada, and IDEA in Germany, where phase II trials are currently in progress. The IDEA technology (TRANSFEROMEs®) is directed to the transport of large molecules, such as peptides, across the dermal barrier. FIG. 6 illustrates the effect of molecular weight and lipophilicity on the rate of transdermal transport in case of permeation (upper and lower gray curve for the more or less lipophilic substances, respectively) or of the TRANSFEROME® mediated penetration (black line and bullets). Gray bullets represent the commercial drugs in transdermal patches. Regardless of the technology, the ability to efficiently transport peptides transdermally is proven and imminent. In particular, both insulin and glucagon can be delivered transdermally, thus providing some embodiments of the present invention that are practiced using transdermal patches and similar devices.

A variety of possible patch structures and matrices can be employed, with the specific type selected according to the specific mode of use intended. For example, one can employ two basic types of insulin matrix, one for basal insulin replacement and one for prandial insulin replacement. Glucagon patches can be formulated to provide post-prandial glucagon for protection from hypoglycemia or basal glucagon replacement. In one embodiment, the invention can be practiced using patch matrices comprising combinations of these basic types, either together in the same matrix or separately in sub-matrices.

Thus, the following patch matrices can be useful in the practice of some embodiments:

a matrix containing insulin for basal insulin replacement;
a matrix containing insulin for prandial insulin replacement;
a matrix containing glucagon for basal glucagon replacement;
a matrix containing glucagon for post-prandial protection from hypoglycemia;
a matrix containing insulin for prandial insulin replacement and glucagon for post-prandial protection from hypoglycemia;
a matrix containing insulin and glucagon for basal replacement of both insulin and glucagon; and
matrices which are composed of 2 or more sub-matrices, each sub matrix being one of the matrices described above.

Topical creams can be used as an alternative to a patch.

For prandial insulin matrices, short acting insulins such as LISPRO (HUMALOG), ASPART (NOVOLOG), or GLULISINE (APIDRA) can be used. The prandial insulin matrix is typically applied at or at some time before mealtimes, according to its rapidity of onset. A prandial insulin patch which minimizes the time to onset can be used so that the patch is applied near to mealtimes. The time to onset depends on the insulin concentration and the nature of the formulation. For example, a simple wet-matrix of insulin has slower onset than an insulin patch formulated according to U.S. Pat. No. 5,707,641. Monomeric insulin will act faster and be more easily absorbed than larger clusters of insulin molecules, because molecular size impacts bioavailability from transdermal patches.

A number of different methods of managing the delivery of prandial insulin can be utilized. For example, patches of different concentrations can be used for fixed periods of time, and the concentration selected by the patient would depend on the amount of carbohydrate eaten. The duration for which the patch is worn could be fixed. The patch would not necessarily be exhausted on removal, i.e. it could deliver a fixed concentration throughout its use. As another example, single concentration prandial patches could be employed as follows. The time the patch is worn is varied according to the amount of carbohydrate eaten. The patch would not necessarily be exhausted on removal, i.e. it could deliver a fixed concentration throughout its use.

As another example, prandial patches containing fixed doses of insulin could be used. The advantage of a self-exhausting patch is that failure to remove them does not of itself carry the risk of hypoglycemia. Such a patch would be substantially exhausted on removal and the rate of infusion would be front loaded. In one embodiment, the prandial insulin patch used has a variable insulin concentration (appropriate to the amount of carbohydrate consumed), has a very rapid onset (preferably immediate but not more than one hour), is removed or deactivated after a fixed length of time (preferably from between 3 and 5 hours) and activated at (or no longer than one hour before) mealtimes. Prandial glucagon patches are applied at mealtimes or at some predetermined time after the meal according to the rapidity of onset associated with the patch. The rate of onset is determined both by the concentration of the glucagon used and the nature of the formulation used. For example, a simple wet-matrix of glucagon would be expected to have a slower onset than a glucagon patch formulated according to the techniques described in U.S. Pat. No. 5,707,641.

In one embodiment, the glucagon patch is constructed so that peak output of glucagon is reached at some time between 2 and 5 hours after application. This patch is applied at mealtimes. The amount of glucagon in the patch will be an amount sufficient to deliver to the patient an amount equivalent to more than 5-30 ng/kg/min., and even more preferably, 8-16 ng/kg/min. of glucagon administered subcutaneously. In some embodiments, the amount of glucagon administered is between 0.1-30 ng/kg/min.

A number of different patch constructions can be used. These include:

a patch containing a single matrix or set of sub-matrices in a single compartment;
a patch containing 2 or more separate compartments each containing its own matrix or set of sub-matrices, the patch being activated or deactivated as a single unit; and
a patch containing 2 more separate and independent compartments, each containing its own matrix or set of sub-matrices, in which each compartment is independently activated and deactivated.

Other patch configurations can be employed, and practice of the invention is not limited to the configurations described above.

A. Insulin Administered Transdermally [Including Patch and Topical Cream]

(i) Insulin Administered Transdermally [Including Patch and Topical Cream] and by Subcutaneous Injection In this example only prandial insulin and prandial glucagon are administered by transdermal patch. This can be achieved in a variety of ways, including: (i) use of a single matrix of glucagon and insulin admixed; (ii) use of a single compartment with two sub matrices, one containing insulin and the other containing glucagon; (iii) use of a single patch containing two compartments, one containing insulin and the other containing glucagon, both compartments being activated and deactivated simultaneously; and (iv) use of two separate patches (or two compartments in a unitary patch), one containing insulin and the other containing glucagon, each patch or compartment being independently activated and deactivated. Basal insulin is delivered parenterally as described in Example 1.A.i by subcutaneous injection of a long-acting insulin such as GLARGINE or ULTRALENTE. In one embodiment, method (i) is used. If different matrices are used to achieve the desired pharmacokinetics, then method (ii) or (iii) can be used. If the timing of insulin onset and glucagon onset is not matched, then method (iv) can be used.

In this illustrative example, method (ii) above is used. The user activates the prandial patch at mealtimes (or preferably within one hour before mealtimes), thereby activating both sub-matrices at the same time. If a fixed concentration patch is used, the user removes the patch after a period of time proportionate to the amount of carbohydrate ingested. If a variable concentration patch is used, then the user removes the patch after a fixed period of time, typically between 1 and 3 hours after eating. In one embodiment, fixed concentrations are used. In such an embodiment, the amount of glucagon administered can be increased with the amount of insulin administered.

(ii) Insulin Administered Transdermally [Including Patch and Topical Cream]

In this example, both the insulin and glucagon are administered transdermally. Two different types of patch (or independently actuated compartments) can be employed. One patch (or compartment) contains a matrix designed to replace basal insulin over a 24 hour period. A single patch (or compartment) containing both the prandial insulin and glucagon in separate sub-matrices with onset times appropriate to applying the prandial patch (or activating the prandial compartment) at (or near) mealtimes can be used.

In one embodiment a unitary device containing four independently actuable compartments is used, one containing basal insulin, which is activated on application and left active for 24 hours, and the other 3 compartments containing the prandial insulin and glucagon in separate sub-matrices within the same compartment, each compartment being separately activated at mealtimes and deactivated at some time after the meal, the time of activation being proportional to the amount of carbohydrate consumed.

On beginning a meal (or at some time up to an hour before the meal), the patient activates one of these prandial compartments [e.g. by pulling away a hermetic plastic seal between the patch and the skin], a process which initiates the transdermal infusion of the insulin and glucagon. At some later time, a period in direct proportion to the amount of carbohydrate taken, the prandial compartment is deactivated [e.g. by replacing the barrier used to activate the compartment or the total removal of that compartment from the end of the patch]. The insulin formulation in the insulin sub-matrix is short acting insulin, and the patch is designed for rapid onset. The glucagon formulation in glucagon sub-matrix is designed to reach efficacious concentrations in the bloodstream between 1 and 3 hours after activation of the compartment, hence providing protection from hypoglycemia at the appropriate part of the cycle as described in Example 13.A.i.

In an alternative embodiment, a unitary device which allows for more than 3 meals a day may easily be devised by allowing for more than 3 prandial compartments. In an alternative embodiment, as described above, the prandial drugs may be contained in totally separate (and independently actuated) prandial patches. In an alternative embodiment, the prandial patch may consist of separate insulin and glucagon compartments so that each may be independently activated and deactivated.

A unitary device containing separate and independently controlled compartments for insulin and glucagon could have 7 separate compartments, one for basal insulin, 3 for prandial insulin, and 3 for prandial glucagon. The basal patch is designed to replace basal insulin (worn for 24 hours before being replaced). The insulin used may be any insulin suitable for transdermal delivery. The basal insulin compartment may also optionally contain an amount of glucagon (admixed or in a sub-matrix) sufficient to supply basal glucagon over each 24 hour period. This would have the beneficial effect of providing protection from hypoglycemia throughout the day and in particular during sleep.

The amount of glucagon in the patch can be an amount sufficient to deliver to the patient an amount equivalent to more than 5-30 ng/kg/min. of subcutaneously administered glucagon, for example, more than 6-20 ng/kg/min., and for another example, 8-16 ng/kg/min. of glucagon. In other embodiments, the amount administered is an amount equivalent to 0.1 to 30 ng/kg/min or 4.0 to 20 ng/kg/min. administered subcutaneously. Greater amounts of glucagon can be present when more than 0-3 Units of insulin are to be administered. For example, a greater amount of glucagon can be present when 3-20 Units of insulin are to be applied in one hour. Alternatively, the same amount of glucagon is present regardless of the amount of insulin.

B. Insulin Administered by Inhalation [Including Pulmonary, Buccal Nasal and Sublingual]

In this example, insulin is delivered by inhalation, as described above. Inhalation can be the mode for delivery of only the prandial insulin delivery (basal being delivered parenterally), or all insulins used can be delivered by inhalation. The patient administers an amount of insulin appropriate to his or her meal by inhalation (in one or more actuations). The patient can optionally increase the insulin after a meal as appropriate.

The glucagon is administered by patch as described in Example 13.A.i. The patch (or set of glucagon compartments in a unitary patch) is attached to the skin, and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, as described herein, the glucagon in the patch is a long acting glucagon (e.g. iodinated glucagon). The patch may then, in some embodiments, be worn for a shorter time while still ensuring that the protection afforded by the modified glucagon is provided over a period of 2-5 hours.

In another embodiment, the user can apply the glucagon by means of a transdermal cream, which acts similarly to a transdermal patch (an amount equivalent to at least about 8-16 ng/kg/min. of glucagon administered subcutaneously can be administered through the cream). The formulation of such a cream can differ from the formulation used in a patch but perform essentially the same function. When glucagon is administered in this way, it may be advantageous to encapsulate the glucagon in liposomes or TRANSFEROMEs® to prevent the supply of glucagon drying on the skin and reducing bioavailability.

C. Insulin Administered Parenterally

In accordance with Example 1.A.i, the patient's insulin needs are met by parenteral administration. The glucagon is administered by patch as described in Example 13.A.i. The patch (or set of glucagon compartments in a unitary patch) is attached to the skin and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, as described herein, the glucagon in the patch is a long acting glucagon (e.g. iodinated glucagon). The patch may then be worn for a shorter time while still ensuring that the protection afforded by the modified glucagon is provided over the required period of 2-5 hours.

In an alternative embodiment, the user may apply the glucagon by means of a transdermal cream, which acts similarly to a transdermal patch. The formulation of such a cream can differ from the formulation used in a patch but performs essentially the same function. When glucagon is administered in this way, it may be advantageous to encapsulate the glucagon in liposomes or TRANSFEROMEs® to prevent the glucagon from drying on the skin and reducing bioavailability.

D. Insulin Administered by Pump

In this example, the patient's insulin needs are administered by pump as described in Example 2. The glucagon is administered by patch as described in Example 13.A.i. The patch (or set of glucagon compartments in a unitary patch) is attached to the skin and the patch or (sub compartment) is activated at mealtimes. The patch is designed to have slow onset, so that the glucagon is only present in the body in efficacious quantity after 2 hours. The patch is worn for 4 hours before being removed, the residual glucagon in the body being sufficient to provide protection from hypoglycemia over the required period of 2-5 hours.

In one embodiment, the glucagon in the patch is a long acting glucagon (e.g. iodinated glucagon). The patch may then be worn for a shorter time while still ensuring that the protection afforded by the modified glucagon is provided over the required period of 2-5 hours.

In an alternative embodiment, the user may apply the glucagon by means of a transdermal cream, which acts similarly to a transdermal patch. The formulation of such a cream may differ from the formulation used in a patch but performs essentially the same function. When glucagon is administered in this way, it may be advantageous to encapsulate the glucagon in liposomes or TRANSFEROMEs® to prevent the glucagon from drying on the skin and reducing bioavailability.

EXAMPLE 14

Co-Administration of Glucagon by Inhalation and Insulin for the Control of Diabetes and Prevention of Hypoglycemia [Including Pulmonary, Buccal, Nasal and Sublingual]

A number of dry powder inhalation technologies are currently in development, including: Aradigm's AERx®, Inhale Therapeutics' Exubera®, Alkermes' and Eli Lilly's AIR, Insulin Technospheres (Mannkind/PDC), and Aerogen's and Disetronic's Aerodose. Methods and devices for delivering insulin to the pulmonary alveoli, where it may be absorbed into the blood stream, are described in U.S. Pat. Nos. 5,997,848; 6,131,567; 6,024,090; 5,970,973; 5,672,581; 5,660,166; 5,404,871; and 5,450,336. The main difficulties that had to be overcome to enable aerosol macromolecular delivery were: low system efficiency (bioavailability); low drug mass per inhalation (c.f asthma); and poor dosing reproducibility.

One relevant factor is efficiency (bio-availability). Bioavailability depends primarily on the aerosol particle size (most existing systems only deliver 10%-20% of the drug administered to the alveoli) rather than on the nature of the drug being administered. When the drug being delivered actually reaches the alveoli, its bioavailability is then very high almost regardless of the drug in question. Because the technical problems (and solutions) associated with delivering insulin are similar to those for delivering glucagon, the solutions enabling delivery of insulin are directly applicable to similarly sized macromolecules like glucagon. One embodiment provides dry powdered formulations prepared by admixing insulin and glucagon. The use of inhalers for delivering insulin is primarily aimed at supplying rapid insulins for prandial purposes. Long acting insulins can be delivered by inhalation if desired.

Some embodiments can be practiced using inhalers in a number of ways, including with insulin and glucagon in separate inhalers; with insulin and glucagon admixed in a fixed ratio in an inhaler; with a dual chamber inhaler in which insulin and glucagon are administered separately; and with dual chamber inhalers in which insulin and glucagon are administered simultaneously. Because prandial inhalers typically contain rapid acting insulins, they are unsuitable (in the way that insulin pumps are) for the delivery of basal insulin. A separate pump or chamber can be provided if both prandial and basal insulins are to be delivered by inhalation.

A. Insulin Administered by Inhalation [Including Pulmonary, Buccal Nasal and Sublingual]

The hypothetical patient administers basal insulin using ULTRALENTE by subcutaneous injections at a dosage level of 20 units administered at bedtime. Alternatively, he may choose to administer the same drug (in a dose that would provide a daily bioavailability of 20 units) by inhalation. It may also be beneficial or desirable for him to administer the basal dose by inhaler at a number of times during the day, for example, at mealtimes in addition to bedtime. Because there is a slight delay (approximately 20 minutes) before insulin attains significant serum concentration when compared to subcutaneous delivery, the user will administer his prandial insulin requirement approximately 20 minutes before eating. He does this by administering between 25 and 50 units (assuming a bioavailability of approximately 20%) of insulin by means of a metered dose inhaler.

The inhaler may be dose alterable (see U.S. Pat. Nos. 5,970,973; 5,672,581; 5,660,166; 5,404,871; and 5,450,336) or similar to currently used asthmatic devices, which deliver fixed and preset doses on each actuation. Whichever type is used, it may be desirable to administer the insulin in multiple actuations. By so doing, the patient can tailor his intake according to the amount of carbohydrate he actually consumes, rather than the amount he expects to eat, by "topping up" his dose at some time after beginning the meal. Furthermore, the more actuations used to administer the insulin, the better the corresponding dose reliability (reproducibility), because inhalation administration tends to vary from actuation to actuation, and multiple actuation delivery has an averaging or smoothing effect.

To prevent hypoglycemia associated with using inhaled insulin from occurring between 2 and 5 hours after eating, a glucagon inhaler is used to administer a s.c. dose equivalent of more than 5 to 16 ng/kg/min. of glucagon administered through inhalation between hours 2 and 5 following the meal. In one embodiment, different inhalers for each type of insulin and for glucagon are used. In one embodiment, a unitary inhaler with at least 2 drug chambers (for prandial insulin, glucagon and/or optionally basal insulin) and capable of independent actuation is used.

B. Insulin Administered Parenterally

In accordance with Example 1.A.i, the patient administers his basal and prandial insulin parenterally. Because the risk of hypoglycemia associated with using LISPRO insulin typically occurs between 2 and 5 hours after eating, the glucagon inhaler is used to administer a s.c. dose equivalent of 6 to 16 ng/kg/min. (i.e., an amount through inhalation to get the same effect on blood glucose as though 6-16 ng/kg/min. of glucagon administered subcutaneously) between hours 2 and 5 following the meal. Alternatively, a modified glucagon of long-acting duration (e.g. iodinated glucagon) with delayed onset is used in the glucagon inhaler and administered at mealtimes with the prandial insulin.

C. Insulin Administered by Pump

In accordance with Example 2.A, basal and prandial insulin are delivered by pump. The risk of hypoglycemia arises after 2 to 3 hours, and so the patient administers glucagon by inhaler 2 hours after eating. He administers one puff from a metered dose inhaler at hours 2, 3 and 4. thus providing protection during the period of susceptibility. The dose per actuation corresponds to a s.c. dose equivalent amount of more than 5 to 16 ng/kg/min. of glucagon. Alternatively, a modified glucagon of long-acting duration (e.g. iodinated glucagon) with delayed onset is used in the glucagon inhaler and administered at mealtimes with the prandial insulin.

D. Insulin Administered Transdermally [Including Patch and Topical Cream]

In accordance with Example 3.A.ii, the patient administers his insulin (both basal and prandial) by transdermal patch or by topical cream. The risk of hypoglycemia arises after 2 to 3 hours, and so the patient administers glucagon by inhaler 2 hours after eating. He administers one puff from a metered dose inhaler at hours 2, 3. and 4. thus providing protection during the period of susceptibility. The dose per actuation corresponds to a s.c. dose equivalent amount of more than 5 to 16 ng/kg/min. glucagon. Alternatively, a modified glucagon of long-acting duration (e.g. iodinated glucagon) with delayed onset is used in the glucagon inhaler and administered at mealtimes with the prandial insulin.

EXAMPLE 15

Co-Administration of Glucagon and Insulin, Admixed and Parenterally for the Control of Diabetes and Prevention of Hypoglycemia In Example 1. the insulin and glucagon were administered parenterally and separately. In one embodiment, the two drugs are administered simultaneously in admixed form. Insulin and glucagon may be admixed with little if any interaction or degradation of either product. In non-diabetics, it is typically found that following the increased insulin output after a meal of carbohydrate there is an associated increase in glucagon output (actually a restoration of output following the initial depression of glucagon output due to the initial gut-induced rise in blood glucose after the ingestion of carbohydrate). This pattern of insulin production followed by glucagon production assumes a relatively fixed relationship.

To ensure that the glucagon provides protection over the period required, one can increase the amount of the glucagon component in the admixture so that it is present in the required concentrations when desired (to prevent hypoglycemia between 2 and 5 hours after the meal, in a s.c. dose equivalent of more than 5 to 30 ng/kg/min., and preferably 8-16 ng/kg/min., or one can use a glucagon formulation with delayed onset. In one embodiment, the formulation of glucagon has both a delayed release and an extended release (e.g., delayed by 2 to 3 hours and releasing over approximately 3 hours). For example, any of the formulations discussed herein may be used.

In this example, an iodination method of increasing half life (as described in U.S. Pat. No. 3,897,551; see form I3G) is employed. The LISPRO insulin and I3Glucagon are admixed so that the modified glucagon is present at approximately 1.5% by weight of the insulin in the mixture (keeping the concentration of insulin per ml in our LISPRO formulation constant). Because of the longer lasting effect of the modified glucagon, a smaller proportion of glucagon to insulin by weight will be required.

The hypothetical patient then administers between 5 and 10 units (measured in terms of the insulin contained therein) of the insulin-glucagon formulation at mealtimes in the standard way. In so doing, he administers a s.c. dose equivalent of more than 5 to up to 16 ng/kg/min. of modified glucagon. Given the longer action of the modified glucagon, this provides (assuming the modified glucagon has, for example, twice the effect on glucose levels compared to standard glucagon) the same protection as described in Example 1.A. The glucagon so administered will be efficacious continuously between hours 2 and 5 as required.

EXAMPLE 16

Co-Administration of Glucagon and Insulin, Admixed, Transdermally for the Control of Diabetes and Prevention of Hypoglycemia [Including Patch and Topical Cream]

In this example, both the insulin and glucagon are administered by transdermal delivery. The prandial insulin and glucagon are admixed in the same matrix or cream. Two different types of patch (or independently actuated compartments) can be employed. One patch (or compartment) will contain a matrix designed to replace basal insulin over a 24 hour period. This patch can contain an amount of glucagon so that a s.c. dose equivalent of more than 5 to up to 20 ng/kg/min. of glucagon is delivered to the patient. The other patch (or independently controlled compartment) provides prandial glucagon and insulin in a single matrix. The onset times of the glucagon and insulin are matched so that when the patch is actuated, insulin reaches efficacious plasma levels very quickly whereas the glucagon only reaches efficacious levels after 2-3 hours. The patch is applied at mealtimes and preferably no more than one hour before the meal.

In one embodiment, a unitary device containing four independently actuable compartments is used, one containing basal insulin, which is activated on application and left active for 24 hours, and the other 3 compartments containing the prandial insulin and glucagon in the same matrix, each compartment being separately activated at (or near) mealtimes and deactivated at some time after the meal, the time of activation being proportional to the amount of carbohydrate consumed. On beginning a meal (or up to an hour before the meal), the patient activates one of these prandial compartments (e.g., by pulling away a hermetic plastic seal between the patch and the skin), a process which initiates the transdermal infusion of the admixed insulin and glucagon. At some later time, a period in direct proportion to the amount of carbohydrate taken, the prandial compartment is deactivated (e.g by replacing the barrier used to activate the compartment or the total removal of that compartment from the end of the patch).

The combined insulin and glucagon formulation in the prandial compartment contains short acting insulin, and the patch is designed for rapid onset of the insulin. The glucagon component is designed to reach efficacious concentrations in the bloodstream between 1 and 3 hours after activation of the compartment, hence providing protection from hypoglycemia at the appropriate part of the cycle.

In an alternative embodiment, a unitary device which allows for more than 3 meals a day can be used and contains more than 3 prandial compartments. The basal patch is designed to replace basal insulin (worn for 24 hours before being replaced). The insulin used may be any insulin suitable for transdermal delivery. It may be advantageous to use intermediate duration insulin in preference to short-acting insulin so that any variation in insulin absorption over the lifetime of the patch would be minimized by the relatively long lifetimes of the insulin involved. The basal insulin compartment may also optionally contain an amount of glucagon (admixed) sufficient to supply basal glucagon over each 24 hour period. This would have the beneficial effect of providing protection from hypoglycemia throughout the day and in particular during sleep.

EXAMPLE 17

Co-Administration of Glucagon and Insulin, Admixed, by Inhalation for the Control of Diabetes and Prevention of Hypoglycemia [Including Pulmonary, Buccal, Nasal and Sublingual Delivery]

The present embodiment provides methods and pharmaceutical formulations for delivery of glucagon admixed with insulin by inhalation. In this example, a long acting glucagon (such as, for example, iodinated glucagon as described in U.S. Pat. No. 3,897,551. e.g. I2G, or a zinc protamine glucagon) is admixed with LISPRO insulin and delivered by a typical insulin inhaler (e.g. as disclosed in patent U.S. Pat. No. 5,970,973). Basal insulin may be delivered in the standard way by subcutaneous injection, as described in Example 1A, or it may be delivered by inhaler. Glucagon may optionally be included in this formulation in an extended release formulation if desired to provide basal glucagon replacement.

The insulin powder used is admixed with the modified glucagon so that the modified glucagon content is a s.c. dose equivalent of more than 5 to 20 ng/kg/min., and more preferably between 8 and 16 ng/kg/min. for 1-3 units of insulin used. Proportionally larger amounts of glucagon can be used when larger amounts of insulin are used (although the amount of glucagon can stay constant regardless of the amount of insulin used). The amount can be adjusted as need, in light of the results from the previous examples for this particular embodiment. The patient will administer the combined insulin and glucagon at mealtimes to provide systemic insulin equivalent to between 5 and 10 units.

Although the present invention has been described in detail with reference to specific embodiments, those of skill in the art will recognize that modifications and improvements are within the scope and spirit of the invention, as set forth in the claims that follow. All publications and patent documents cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. Definitions provided herein control over definitions found in the cited references or elsewhere. The invention having now been described by way of written description and example, those of skill in the art will recognize that the invention can be practiced in a variety of embodiments and that the foregoing description and examples are for purposes of illustration and not limitation of the following claims.

We claim:

1. A method for reducing a risk of an onset of hypoglycemia in a subject who is not experiencing hypoglycemia, said method comprising administering glucagon to said subject in an amount equivalent to a subcutaneous administration of glucagon at a rate of 2 to 16 ng of glucagon per kg of subject weight per minute.

2. The method of claim 1, wherein the rate is 4 to 16 ng of glucagon per kg of subject weight per minute.

3. The method of claim 1, wherein the subject has a blood glucose level of at least 70 mg/dl during the administering.

4. The method of claim 3, wherein the subject's blood glucose is at least 200 mg/dl.

5. The method of claim 1, wherein the glucagon is administered for at least six hours.

6. The method of claim 5, wherein said glucagon is a slow release formulation of glucagon.

7. The method of claim 1, wherein the glucagon is administered in a slow release formulation of glucagon and provides glucagon at a rate of 1 to 20 ng of glucagon per kilogram of subject weight per minute for 5 hours once administered to the subject.

8. The method of claim 1, consisting of subcutaneously administering glucagon to said subject in a dosage that provides glucagon to the subject at a rate of 2 to 20 ng of glucagon per kg of subject weight per minute.

9. The method of claim 1, wherein the glucagon is administered on a daily basis.

10. A method of reducing a risk of an onset of hypoglycemia in a non-hypoglycemic subject without inducing hyperglycemia, said method comprising administering glucagon in a dose equivalent to a subcutaneous administration of 2 to 16 ng of glucagon per kg of subject weight per minute of desired effectiveness.

11. The method of claim 10, wherein the glucagon is administered subcutaneously.

12. The method of claim 10, wherein the glucagon is administered intravenously.

13. The method of claim 10, wherein the glucagon is administered via a pump.

14. The method of claim 10, wherein said glucagon comprises a depot formulation of glucagon.

15. The method of claim 10, wherein the subject has a blood glucose level of at least 70 mg/dl during the administering.

16. A method of reducing a risk of hypoglycemia without inducing hyperglycemia, which method comprises:
   administering glucagon subcutaneously;
   wherein administration of glucagon occurs daily;
   wherein when said glucagon is administered the subject has a blood glucose level of at least 70 mg/dL and is not exhibiting hypoglycemic symptoms
   wherein said glucagon is administered subcutaneously in a dosage that provides 2 to 16 ng of glucagon per kilogram of subject weight per minute; and wherein said subcutaneous administration provides plasma glucagon levels that are sustained for 6 to 8 hours in the range of 100 to 200 pg/ml.

17. The method of claim 16, wherein the glucagon is administered subcutaneously at a rate of 4 to 16 ng of glucagon per kilogram of subject per minute.

18. The method of claim 16, wherein the subject is at risk for hypoglycemia because the subject is receiving a hypoglycemic agent.

19. The method of claim 18, wherein the hypoglycemic agent is selected from the group consisting of: an insulin sensitizer, a DPP IV inhibitor, a GLP 1 analog, an insulin secretagogue, sulfonylurea, acetohexamide, chlorpropamide, tolazamide, tolbutamide, glimepiride, glipizide, extended release glipizide, glyburide, micronized glyburide, meglitinide, nateglinide, repaglinide, a gastric inhibitory polypeptide, glucagon-like peptide-1; morphilinoguanide BTS 67582, a phosphodiesterase inhibitor, a succinate ester derivative, an insulin receptor activator, an insulin sensitizing biguanide, metformin, thiazolidinedione, troglitazone, pioglitazone, roziglitazone, a non-TZD peroxisome proliferator activated receptor -gamma agonist GL262570, an aipha-glucosidase inhibitor, acarbose, miglitoim, glucovance, a tyrosine phosphatase inhibitor, vanadium, a PTP-1B inhibitor, an AMPK activator, a 5-aminoimidazole-4-carboxamide ribonucleoside, exendin, pramlintide acetate, D-Chiro-Inositol, an altered peptide ligand (NBI-6024), an anergix DB complex, a GABA inhibit, a melanocortin, a Glucose lowering agent (ALT-4037), an insulin mimic, an insulin-like growth factor-1, metoclopramide HCL, a motilide, and a GAG mimetic.

20. The method of claim 19, wherein the hypoglycemic agent comprises an insulin sensitizer.

* * * * *